US010308921B2

(12) United States Patent
Tang et al.

(10) Patent No.: US 10,308,921 B2
(45) Date of Patent: Jun. 4, 2019

(54) POLYPEPTIDES HAVING CELLULOLYTIC ENHANCING ACTIVITY AND POLYNUCLEOTIDES ENCODING SAME

(71) Applicants: Novozymes, Inc., Davis, CA (US); Novozymes A/S, Bagsvaerd (DK)

(72) Inventors: Lan Tang, Beijing (CN); Ye Liu, Beijing (CN); Yu Zhang, Beijing (CN); Junxin Duan, Beijing (CN); Tarana Shaghasi, Dixon, CA (US)

(73) Assignee: Novozymes, Inc., Davis, CA (US)

( * ) Notice: Subject to any disclaimer, the term of this patent is extended or adjusted under 35 U.S.C. 154(b) by 488 days.

(21) Appl. No.: 14/352,875

(22) PCT Filed: Oct. 31, 2012

(86) PCT No.: PCT/CN2012/083853
§ 371 (c)(1),
(2) Date: Apr. 18, 2014

(87) PCT Pub. No.: WO2013/064075
PCT Pub. Date: May 10, 2013

(65) Prior Publication Data
US 2014/0256000 A1    Sep. 11, 2014

Related U.S. Application Data

(60) Provisional application No. 61/565,776, filed on Dec. 1, 2011.

(30) Foreign Application Priority Data

Oct. 31, 2011    (WO) ................ PCT/CN2011/081564

(51) Int. Cl.
| C07H 21/04 | (2006.01) |
| C12N 15/00 | (2006.01) |
| C12N 9/24 | (2006.01) |
| C07K 14/37 | (2006.01) |
| C12P 19/14 | (2006.01) |
| C12N 9/42 | (2006.01) |
| C12P 19/02 | (2006.01) |

(52) U.S. Cl.
CPC ............ *C12N 9/2405* (2013.01); *C07H 21/04* (2013.01); *C07K 14/37* (2013.01); *C12N 9/244* (2013.01); *C12N 9/2434* (2013.01); *C12N 9/2437* (2013.01); *C12P 19/02* (2013.01); *C12P 19/14* (2013.01); *C07K 2319/02* (2013.01); *Y02E 50/17* (2013.01)

(58) Field of Classification Search
None
See application file for complete search history.

(56) References Cited

U.S. PATENT DOCUMENTS

| 5,945,580 A * | 8/1999 | Dunsmuir | .......... C12N 15/8246 435/320.1 |
| 2009/0099079 A1* | 4/2009 | Emalfarb | ............... C07H 21/00 514/1.2 |

FOREIGN PATENT DOCUMENTS

| WO | 2005074647 A2 | 8/2005 |
| WO | 2005074656 A2 | 8/2005 |
| WO | 2007089290 A2 | 8/2007 |
| WO | 2008148131 A1 | 12/2008 |
| WO | 2008151043 A1 | 12/2008 |
| WO | 2009085859 A2 | 7/2009 |
| WO | 2009085864 A2 | 7/2009 |
| WO | 2009085868 A1 | 7/2009 |
| WO | 2009085935 A2 | 7/2009 |
| WO | 2010065830 A1 | 6/2010 |
| WO | 2010138754 A1 | 12/2010 |
| WO | 2011005867 A1 | 1/2011 |
| WO | 2011035027 A2 | 3/2011 |
| WO | 2011039319 A1 | 4/2011 |
| WO | 2011041397 A1 | 4/2011 |
| WO | 2011041504 A1 | 4/2011 |
| WO | 2012030799 A1 | 3/2012 |

OTHER PUBLICATIONS

2008, Genbank Access No. XP_959499.
2008, Genbank Access No. XP_001225931.
2008, Genbank Access No. XP_001225249.
2008, Genbank Access No. XP_001230041.
2008, Genbank Access No.—XP_001223687.
2008, Genbank Access No. XP_001219904.
2010, Genbank Access No. XP_001911495.
2011, Genbank Access No.—EGS20384.
2011, Genbank Access No. AEO68157.
2011, Genbank Access No. AEO64177.
2011 Genbank Access No. EGS23404.
2011 Genbank Access No. EGS17558.
2011 Genbank Access No. AEO64593.
2011 Genbank Access No. AEO67396.
2011 Genbank Access No. AEO68763.
2011 Genbank Access No. AEO66274.

* cited by examiner

Primary Examiner — Phuong T Bui
(74) Attorney, Agent, or Firm — Robert Starnes

(57) ABSTRACT

The present invention provides isolated polypeptides having cellulolytic enhancing activity and polynucleotides encoding the polypeptides, catalytic domains, cellulose binding domains and polynucleotides encoding the polypeptides, catalytic domains or cellulose binding domains. The invention also provides nucleic acid constructs, vectors, and host cells comprising the polynucleotides as well as methods of producing and using the polypeptides, catalytic domains or cellulose binding domains.

48 Claims, 13 Drawing Sheets
Specification includes a Sequence Listing.

SEQUENCE LISTING

<160> NUMBER OF SEQ ID NOS: 76

<210> SEQ ID NO 1
<211> LENGTH: 975
<212> TYPE: DNA
<213> ORGANISM: Corynascus thermophilus

<400> SEQUENCE: 1

```
atgccccctc cacggctaca cacgttcctt gccctcttgg ccctggtatc agccccacc       60 gcacggggc attcccatct cgcatacatc atcatcaacg gcgaggtgta ccacggattc      120
gacccgcggc cggggagga gaactcgccg gcgcgcgtgg gctggtcgac ggggcggtc       180 gacgacgggt tcgtggggcc ggccgactac tcgtcgcccg acataatctg ccacgtcgag     240
ggggccagcc cgccggcgca cgcgcccgtc cgggccggcg accgggttca cgtgcagtgg     300
aacggctggc cgctcgggca tgtggggccg gtgctgtcgt acctggcccc ctgcggcggc     360
ctggaggggg ccgagcgcgg gtgtgccgga gtggacaagc ggcagctgcg gtggaccaag     420
gtggacgact cgctgccggc gatggagaga ctgtccacca cggtcggggc cgcggacggc     480
ggcggcgtgc ccgggcagcg ctgggccacc gacgtgctgg tcgcggccaa caacagctgg     540
caggtcgaga tcccgcgcgg gctccgggac gggccgtacg tgctgcggca cgagatcgtc     600
gcgctgcact tcgcggccga ccgcggcggc gcgcagaact acccggtctg cgtcaacctc     660
tgggtcgagg gcggcgacgg caccatggag ctggacggct tcgacgccac cgagctctac     720
cggcccgacg acccgggcat cctgctcgac gtgacggccg gcccgcgctc gtacgtcgtg     780
cccggcccga cgctggtcgc ggggccacg cgggtgccgt acgcgcagca gaacagcagc     840
tcggcgaggg cggagggaac ccccgtgatg gtcatcagga gcacagagac ggtgcccctg     900
acggtagcac ctaccccgac caatagtacg ggtcgggctt acgggaggag gtacggaagc     960
aggtttcagg ggtag                                                       975
```

<210> SEQ ID NO 2
<211> LENGTH: 324
<212> TYPE: PRT
<213> ORGANISM: Corynascus thermophilus

<400> SEQUENCE: 2

```
Met Pro Pro Arg Leu His Thr Phe Leu Ala Leu Leu Ala Leu Val
1               5                   10                  15

Ser Ala Pro Thr Ala Arg Gly His Ser His Leu Ala Tyr Ile Ile Ile
            20                  25                  30

Asn Gly Glu Val Tyr His Gly Phe Asp Pro Arg Pro Gly Glu Glu Asn
                35                  40                  45

Ser Pro Ala Arg Val Gly Trp Ser Thr Gly Ala Val Asp Asp Gly Phe
50                  55                  60

Val Gly Pro Ala Asp Tyr Ser Ser Pro Asp Ile Ile Cys His Val Glu
65                  70                  75                  80

Gly Ala Ser Pro Pro Ala His Ala Pro Val Arg Ala Gly Asp Arg Val
                85                  90                  95

His Val Gln Trp Asn Gly Trp Pro Leu Gly His Val Gly Pro Val Leu
                100                 105                 110

Ser Tyr Leu Ala Pro Cys Gly Gly Leu Glu Gly Ala Glu Arg Gly Cys
            115                 120                 125

Ala Gly Val Asp Lys Arg Gln Leu Arg Trp Thr Lys Val Asp Asp Ser
130                 135                 140

Leu Pro Ala Met Glu Arg Leu Ser Thr Thr Val Gly Ala Ala Asp Gly
145                 150                 155                 160

Gly Gly Val Pro Gly Gln Arg Trp Ala Thr Asp Val Leu Val Ala Ala
                165                 170                 175

Asn Asn Ser Trp Gln Val Glu Ile Pro Arg Gly Leu Arg Asp Gly Pro
                180                 185                 190

Tyr Val Leu Arg His Glu Ile Val Ala Leu His Phe Ala Ala Asp Arg
                195                 200                 205

Gly Gly Ala Gln Asn Tyr Pro Val Cys Val Asn Leu Trp Val Glu Gly
210                 215                 220

Gly Asp Gly Thr Met Glu Leu Asp Gly Phe Asp Ala Thr Glu Leu Tyr
225                 230                 235                 240

Arg Pro Asp Asp Pro Gly Ile Leu Leu Asp Val Thr Ala Gly Pro Arg
                245                 250                 255

Ser Tyr Val Val Pro Gly Pro Thr Leu Val Ala Gly Ala Thr Arg Val
                260                 265                 270

Pro Tyr Ala Gln Gln Asn Ser Ser Ser Ala Arg Ala Glu Gly Thr Pro
            275                 280                 285

Val Met Val Ile Arg Ser Thr Glu Thr Val Pro Leu Thr Val Ala Pro
                290                 295                 300

Thr Pro Thr Asn Ser Thr Gly Arg Ala Tyr Gly Arg Arg Tyr Gly Ser
305                 310                 315                 320

Arg Phe Gln Gly

<210> SEQ ID NO 3
<211> LENGTH: 1115
<212> TYPE: DNA
<213> ORGANISM: Corynascus thermophilus

<400> SEQUENCE: 3
atggctccat taacgtccgc agccctgatc ctgggcaccc ttatcagctt ggtctcgggc      60
catggctatc tgaagagcat caccgtcaac ggcaaggagt acctcgcttg gcaggttggc     120
caggacgact atatcaaccc gactccggtc cgatatgccc gcaggcttgc aaacaacggg     180
ccagtcccgg atttcaccac caaggatatc acgtacgttt ccgtggaggc cggcactggc     240
tgtggcggaa gagggcaaga ccgccggact gacgcgtgcc atgactttac agctgcggcg     300
```

```
ccggtggtaa tgagccggct gagggaatca tcgagctgaa ggctggcgac actgtgtacg    360
cgccgtcccc tccccagcta acgttacccg atcgacctca tctggacggt tagctgacag    420
ggtcgtcttc tctcgcacac gcaaatagga ccctcaactg ggaccagtgg ggtagcagcc    480
actccggccc agtcatgaag tgagtcttgc ggccttcccg cgacggacc gtaccagagg     540 ttattacggg agtagcagtc gtaatcagcg aacccattcg aactaacccc tcccgcacca    600
gctatctcgc ccattgcacc aacgacgact gcaagtcgtt caagggcgac agcggcaacg    660
tctgggtcaa gatcgagcag ctcgcgtaca acccgtcggc caaccccccc tgggcgtccg    720
acctcctccg cgagcagggc gccaagtgga aggtgacgat cccgcccacc ctcgcccccg    780
gcgagtacct gctgcggcac gagatcctgg gcctgcacgt cgccggaacc gtgatgggcg    840
cccagttcta ccccagctgc acccagatca gggtcaccca gggcgggaac acgcagctgc    900
cctccggcat cgcgcttccc ggtgcttacg acccgcatga cggggggtgta agtctcggat    960 gtatgatctg gaattgtctc gacgcttgct gacagtgttt attccagatc ttggtcgagt    1020
tgtggagggt taaccagggc caggtcaact acaccgcgcc tggaggaccc gtctggagcg    1080
cggcggcgcc ggatcccaac cgctctggcc cctga                              1115
```

<210> SEQ ID NO 4
<211> LENGTH: 240
<212> TYPE: PRT
<213> ORGANISM: Corynascus thermophilus

<400> SEQUENCE: 4

```
Met Ala Pro Leu Thr Ser Ala Ala Leu Ile Leu Gly Thr Leu Ile Ser
1               5                   10                  15

Leu Val Ser Gly His Gly Tyr Leu Lys Ser Ile Thr Val Asn Gly Lys
            20                  25                  30

Glu Tyr Leu Ala Trp Gln Val Gly Gln Asp Asp Tyr Ile Asn Pro Thr
        35                  40                  45

Pro Val Arg Tyr Ala Arg Arg Leu Ala Asn Asn Gly Pro Val Pro Asp
    50                  55                  60

Phe Thr Thr Lys Asp Ile Thr Cys Gly Ala Gly Gly Asn Glu Pro Ala
65                  70                  75                  80

Glu Gly Ile Ile Glu Leu Lys Ala Gly Asp Thr Val Thr Leu Asn Trp
                85                  90                  95

Asp Gln Trp Gly Ser Ser His Ser Gly Pro Val Met Asn Tyr Leu Ala
            100                 105                 110

His Cys Thr Asn Asp Asp Cys Lys Ser Phe Lys Gly Asp Ser Gly Asn
        115                 120                 125

Val Trp Val Lys Ile Glu Gln Leu Ala Tyr Asn Pro Ser Ala Asn Pro
    130                 135                 140

Pro Trp Ala Ser Asp Leu Leu Arg Glu Gln Gly Ala Lys Trp Lys Val
145                 150                 155                 160

Thr Ile Pro Pro Thr Leu Ala Pro Gly Glu Tyr Leu Leu Arg His Glu
                165                 170                 175

Ile Leu Gly Leu His Val Ala Gly Thr Val Met Gly Ala Gln Phe Tyr
            180                 185                 190

Pro Ser Cys Thr Gln Ile Arg Val Thr Gln Gly Gly Asn Thr Gln Leu
        195                 200                 205

Pro Ser Gly Ile Ala Leu Pro Gly Ala Tyr Asp Pro His Asp Gly Gly
    210                 215                 220
```

Gly Pro Val Trp Ser Ala Ala Ala Pro Asp Pro Asn Arg Ser Gly Pro
225                 230                 235                 240

<210> SEQ ID NO 5
<211> LENGTH: 988
<212> TYPE: DNA
<213> ORGANISM: Corynascus thermophilus

<400> SEQUENCE: 5

```
atgaaatacg ccctccagct cgctgcggcc gcggcttttg cggtgaacag cgcggccggc    60
cactacatct tccagcagtt tgcgacaggc gggacgacgt acccgccctg gaagtacatc   120
cgccgcaaca ccaaccccga ctggctgcag aacgggccgg tgacggacct gtcgtcgacc   180
gacctgcgct gtaacgtggg cgggcaggtc agcaacggga ccgagaccat caccgtcaac   240
gccggcgacg aattcacctt catcctcgac acgcccgtct accacgccgg ccccacctcg   300
ctctacatgt ccaaggcgcc cggcgcggcg gccgactacg acggcagcgg gtcctggttc   360
aagatctatg actggggccc gcagggaacg agctggacgc tgagcggtac gtgtgcctgt   420
ttctcatcat caccacgacc atcctcatga tgattaccgc tctcgttatg attatgctgc   480
tgttgcggtt ctgctggaag agtatctgac cgtctaccg tatccaggct cgtacaccca   540
gagaattccc aggtgcatcc ctgacggcga atacctcctc cgcatccagc agatcggact   600
tcacaacccc ggcgccgagc acaggtacg gtcctggact ccgggtctc ctcttgcgca   660
ccgtcgctga cgcaggacga acaaaaacag ttctacatca gctgcgccca agtcaaggtg   720
gtcaatggcg gcagcaccaa cccgagcccg accgccagat ttccgggagc cttccacagc   780
aacgatcccg gcttgaccgt caacgtaagc ccggcctcgc atcatttccc cgggaaccga   840
aatagcaatg agctgacaac cgatcgtaga tctacaccga ccctctcaac aactacgtcg   900
tccccggacc ccgggttgta agtctctccg gatgccctcc tccgttgatg gtcacgcctt   960
gctaatgtcg tccaagttct cctgctag                                      988
```

<210> SEQ ID NO 6
<211> LENGTH: 225
<212> TYPE: PRT
<213> ORGANISM: Corynascus thermophilus

<400> SEQUENCE: 6

Met Lys Tyr Ala Leu Gln Leu Ala Ala Ala Ala Phe Ala Val Asn
1               5                   10                  15

Ser Ala Ala Gly His Tyr Ile Phe Gln Gln Phe Ala Thr Gly Gly Thr
                20                  25                  30

Thr Tyr Pro Pro Trp Lys Tyr Ile Arg Arg Asn Thr Asn Pro Asp Trp
            35                  40                  45

Leu Gln Asn Gly Pro Val Thr Asp Leu Ser Ser Thr Asp Leu Arg Cys
        50                  55                  60

Asn Val Gly Gly Gln Val Ser Asn Gly Thr Glu Thr Ile Thr Val Asn
65                  70                  75                  80

Ala Gly Asp Glu Phe Thr Phe Ile Leu Asp Thr Pro Val Tyr His Ala
                85                  90                  95

Gly Pro Thr Ser Leu Tyr Met Ser Lys Ala Pro Gly Ala Ala Ala Asp
            100                 105                 110

Tyr Asp Gly Ser Gly Ser Trp Phe Lys Ile Tyr Asp Trp Gly Pro Gln
        115                 120                 125

Gly Thr Ser Trp Thr Leu Ser Gly Ser Tyr Thr Gln Arg Ile Pro Arg
    130                 135                 140

```
Cys Ile Pro Asp Gly Glu Tyr Leu Leu Arg Ile Gln Gln Ile Gly Leu
145                 150                 155                 160

His Asn Pro Gly Ala Glu Pro Gln Phe Tyr Ile Ser Cys Ala Gln Val
                165                 170                 175

Lys Val Val Asn Gly Gly Ser Thr Asn Pro Ser Pro Thr Ala Gln Ile
            180                 185                 190

Pro Gly Ala Phe His Ser Asn Asp Pro Gly Leu Thr Val Asn Ile Tyr
        195                 200                 205

Thr Asp Pro Leu Asn Asn Tyr Val Val Pro Gly Pro Arg Val Phe Ser
    210                 215                 220

Cys
225

<210> SEQ ID NO 7
<211> LENGTH: 859
<212> TYPE: DNA
<213> ORGANISM: Corynascus thermophilus

<400> SEQUENCE: 7
atgaaggccc tctctctcct tgcggctgcc tcggcggtct ctgcccacac catcttcgtc      60
cagctcgaag cggacggcac gaggtacccg gtctcgtacg gcatccggac gccgacgtac     120
gacggcccca tcaccgacgt cacgtccaac gacgttgcct gcaacggcgg gccgaacccg     180
acgaccccgt ccggcgacgt catcacggtc acggcgggca ccacggtcaa ggccatctgg     240
agacacacgc tccagtccgg cccggacgac gtcatggacg ccagccacaa gggcccgacc     300
ctggcctacc tcaagaaggt cgacgacgcc accacggact cgggcatcgg cggcggctgg     360
ttcaagattc aggaggacgg ctacaacaac ggcgagtggg caccagcaa ggtgatctcc      420 aacggcggcg agcactacat gtgagtcctt tctccgacag agcgaggaga aacacagaga     480
gggagagaga gagaggccga ccaatctcgc tgacccgctg caacagcgac atcccggcct     540
gcattccccc gggccagtac ctcctccgcg ccgagatgat tgctctccac agcgccgggt     600
ctcccggcgg tgctcagctc tacgtaagcc tctctgccct tccttattac cacccccccc     660
ccaaacctct gactgacacg cttggcagat ggaatgcgcc cagatcaaca tcgtcggcag     720
ctccggctcc ctgcccagct cgaccgtcag cttccccggc gcgtacagcg ccaacgaccc     780
gggcatcctc atcaacatct actccatgtc cccctcggac acgtacatca ttccgggccc     840
ggaggtcttc acttgctag                                                  859

<210> SEQ ID NO 8
<211> LENGTH: 235
<212> TYPE: PRT
<213> ORGANISM: Corynascus thermophilus

<400> SEQUENCE: 8

Met Lys Ala Leu Ser Leu Leu Ala Ala Ala Ser Ala Val Ser Ala His
1               5                   10                  15

Thr Ile Phe Val Gln Leu Glu Ala Asp Gly Thr Arg Tyr Pro Val Ser
            20                  25                  30

Tyr Gly Ile Arg Thr Pro Thr Tyr Asp Gly Pro Ile Thr Asp Val Thr
        35                  40                  45

Ser Asn Asp Val Ala Cys Asn Gly Gly Pro Asn Pro Thr Thr Pro Ser
    50                  55                  60

Gly Asp Val Ile Thr Val Thr Ala Gly Thr Thr Val Lys Ala Ile Trp
65                  70                  75                  80
```

```
Arg His Thr Leu Gln Ser Gly Pro Asp Asp Val Met Asp Ala Ser His
                85                  90                  95

Lys Gly Pro Thr Leu Ala Tyr Leu Lys Lys Val Asp Asp Ala Thr Thr
            100                 105                 110

Asp Ser Gly Ile Gly Gly Trp Phe Lys Ile Gln Glu Asp Gly Tyr
        115                 120                 125

Asn Asn Gly Glu Trp Gly Thr Ser Lys Val Ile Ser Asn Gly Gly Glu
130                 135                 140

His Tyr Ile Asp Ile Pro Ala Cys Ile Pro Pro Gly Gln Tyr Leu Leu
145                 150                 155                 160

Arg Ala Glu Met Ile Ala Leu His Ser Ala Gly Ser Pro Gly Gly Ala
                165                 170                 175

Gln Leu Tyr Met Glu Cys Ala Gln Ile Asn Ile Val Gly Ser Ser Gly
            180                 185                 190

Ser Leu Pro Ser Ser Thr Val Ser Phe Pro Gly Ala Tyr Ser Ala Asn
        195                 200                 205

Asp Pro Gly Ile Leu Ile Asn Ile Tyr Ser Met Ser Pro Ser Asp Thr
    210                 215                 220

Tyr Ile Ile Pro Gly Pro Glu Val Phe Thr Cys
225                 230                 235
```

<210> SEQ ID NO 9
<211> LENGTH: 1011
<212> TYPE: DNA
<213> ORGANISM: Corynascus thermophilus

<400> SEQUENCE: 9

```
atggccaaga cctctgctct cctcgccggc ctgacgggcg cggccctcgt cgctgcccac      60
ggccacgtca gccacatcat cgtcaacggc gtgtactaca ggaactacga cccgacgacc     120
gactcgtacc agaccaaccc gccgagggtc atcggctggg cggccgccca gcaggacaat     180
ggcttcgtcg agcccaacaa ctttggctcg ccggatgtca tctgccacaa gagcgccact     240
cccggcggcg ccacgccac cgtcgctgcc ggagacaaga tcagcctcgt ctggacgccc     300
gagtggcccg agtccacat cggcccggtc atcgactatc tggcggcctg caacggcgac     360
tgcgagacgg tcgacaagac gtcgctgcgc tggttcaaga tcgacggcgc cggctacgac     420
aagtcgaccg ccgctgggc cgccgacgcc ctgcgcgcca acggcaacag ctggctcgtc     480
cagatcccgt cggacctcaa ggcgggcaac tacgtgctcc gcacgagat catcgccctc     540
cacggcgcca caacgccaa cggcgcccag tcgtacccgc agtgcatcaa cctccgcgtc     600
acgggcggcg gcaacaacct gcccagcggc gtgcccggca cctcgctgta cagggccaac     660
gacccgggca tcctcttcaa ccctacgtc ccctcgcccg actacccggt ccccggcccg     720
tccctcattc ccggcgccgt cagctccatc gcccagagca gtcggtcgc cacggccacg     780
gccacggcca cccctcccgg cggcggcaac aacaaccccc cgccaccac caccgccggc     840
ggccccacca gcaccaccag cagcccctcc cagcagacca ccaccccgcc gtcgggcagc     900
gtgcagacca gtacggcca gtgcggcggc aacggctgga ccggccgac cctgtgcgcc     960
cccggctcga gctgcaccgt tctcaacgag tggtactccc agtgcgtgta a            1011
```

<210> SEQ ID NO 10
<211> LENGTH: 336
<212> TYPE: PRT
<213> ORGANISM: Corynascus thermophilus

<400> SEQUENCE: 10

| | | | | | | | | | | | | | | |
|---|---|---|---|---|---|---|---|---|---|---|---|---|---|---|
|Met|Ala|Lys|Thr|Ser|Ala|Leu|Leu|Ala|Gly|Leu|Thr|Gly|Ala|Ala|Leu|
|1| | | |5| | | | |10| | | | |15| |

Val Ala Ala His Gly His Val Ser His Ile Ile Val Asn Gly Val Tyr
             20                  25                  30

Tyr Arg Asn Tyr Asp Pro Thr Thr Asp Ser Tyr Gln Thr Asn Pro Pro
             35                  40                  45

Arg Val Ile Gly Trp Ala Ala Ala Gln Gln Asp Asn Gly Phe Val Glu
 50                      55                  60

Pro Asn Asn Phe Gly Ser Pro Asp Val Ile Cys His Lys Ser Ala Thr
 65                      70                  75                  80

Pro Gly Gly Gly His Ala Thr Val Ala Ala Gly Asp Lys Ile Ser Leu
                 85                  90                  95

Val Trp Thr Pro Glu Trp Pro Glu Ser His Ile Gly Pro Val Ile Asp
                 100                 105                 110

Tyr Leu Ala Ala Cys Asn Gly Asp Cys Glu Thr Val Asp Lys Thr Ser
             115                 120                 125

Leu Arg Trp Phe Lys Ile Asp Gly Ala Gly Tyr Asp Lys Ser Thr Gly
130                 135                 140

Arg Trp Ala Ala Asp Ala Leu Arg Ala Asn Gly Asn Ser Trp Leu Val
145                 150                 155                 160

Gln Ile Pro Ser Asp Leu Lys Ala Gly Asn Tyr Val Leu Arg His Glu
                 165                 170                 175

Ile Ile Ala Leu His Gly Ala Asn Asn Ala Asn Gly Ala Gln Ser Tyr
             180                 185                 190

Pro Gln Cys Ile Asn Leu Arg Val Thr Gly Gly Gly Asn Asn Leu Pro
     195                 200                 205

Ser Gly Val Pro Gly Thr Ser Leu Tyr Arg Ala Asn Asp Pro Gly Ile
 210                 215                 220

Leu Phe Asn Pro Tyr Val Pro Ser Pro Asp Tyr Pro Val Pro Gly Pro
225                 230                 235                 240

Ser Leu Ile Pro Gly Ala Val Ser Ser Ile Ala Gln Ser Lys Ser Val
                 245                 250                 255

Ala Thr Ala Thr Ala Thr Ala Thr Pro Pro Gly Gly Asn Asn Asn Asn
                 260                 265                 270

Pro Pro Ala Thr Thr Ala Gly Gly Pro Thr Ser Thr Ser Ser
                 275                 280                 285

Pro Ser Gln Gln Thr Thr Thr Pro Pro Ser Gly Ser Val Gln Thr Lys
     290                 295                 300

Tyr Gly Gln Cys Gly Gly Asn Gly Trp Thr Gly Pro Thr Leu Cys Ala
305                 310                 315                 320

Pro Gly Ser Ser Cys Thr Val Leu Asn Glu Trp Tyr Ser Gln Cys Val
                 325                 330                 335

<210> SEQ ID NO 11
<211> LENGTH: 1315
<212> TYPE: DNA
<213> ORGANISM: Corynascus thermophilus

<400> SEQUENCE: 11
atgaaaacgc ttgccgccct cctcgtctcc gccggcctcg tggctgcgca cggctatgtt      60
gaccgtgcca cgatcggcgg caaggagtac caggtaatga caacaaacac ggctactccc     120
gtgtggatgc gtcgtcgaag agtagctaac aatacggtcc ctatagttct accaggtggg     180

```
ctcggtaccg gccagttggc tctccatgcc ggcagttcct gacatgcatc tcgcatattt    240
agccgtacgt tgatccgtac atgggcgaca caaggtaac aacaaaccttt aatataacaa    300 gaacaaccta tccatcctcc ctcccccccc ctctccacac ccccccccctc tctctctctt    360 tctctccttt ctcctctgat gcaccggtcg agcacgcact aaacaggggg taattacggg    420
gggcatttca gcccgacagg gtctcccgct cgatcccggg caacggcccc gtggaggacg    480
tcaactcgct cgacatccag tgcaacgcgg gcgcgcagcc ggccaagctc acgcccccg     540 ccgccgccgg ctcgaccgtg acgctcaact ggaccctctg gcccgactcg cacgtcggcc    600
ccgtcatcac ctacatggcg cgctgccccg acagcggctg ccagaactgg tcgcccggaa    660
cccagtatgg cccattccaa tcctgtttgt tgatattgat gggggtaaa gacggaggggg    720 atggttggcg tgctaaatg gtttactttc ctgatgacag gcccgtctgg ttcaagatca     780
aggagggcgg ccgtgagggc acgtccaacg tctgggcggc cgtacgtgat cacacccgt     840 tccgaaaaca acgaggcaca caccaaagcc aactaacccc tcccttcttt cgctctctat    900
ctctctcgac agacccgct catgaaggcg ccgtcggcgt acacgtacac gatcccggcc     960
tgcctcaaga gcggctacta cctggtgcgg cacgagatca tcgcgctgca ctcggcctgg   1020
cagtaccccg gcgcgcagtt ctacccgggc tgccaccagc tccaggtcac cggcggcggc   1080
tcgaccgtgc cctcggccaa cctggtcgcc ttccccggcg cctacaaggg cagcgacccc   1140
ggcatcacct acgacgcgta caagggtgag ccatctcttt ctctctttct ctctgtctcg   1200
cttttctctt tccttgtgcc tcttggttgt ccgtcttgga gcagggcagg gcgactgacg   1260
cggagtggca gcgcaacctt acacgatccc gggcccgccc gtgtttactt gctaa         1315
```

<210> SEQ ID NO 12
<211> LENGTH: 253
<212> TYPE: PRT
<213> ORGANISM: Corynascus thermophilus

<400> SEQUENCE: 12

```
Met Lys Thr Leu Ala Ala Leu Leu Val Ser Ala Gly Leu Val Ala Ala
1               5                   10                  15

His Gly Tyr Val Asp Arg Ala Thr Ile Gly Gly Lys Glu Tyr Gln Phe
            20                  25                  30

Tyr Gln Val Gly Ser Val Pro Ala Ser Trp Leu Ser Met Pro Ala Val
        35                  40                  45

Pro Asp Met His Leu Ala Tyr Leu Ala Pro Asp Arg Val Ser Arg Ser
    50                  55                  60

Ile Pro Gly Asn Gly Pro Val Glu Asp Val Asn Ser Leu Asp Ile Gln
65                  70                  75                  80

Cys Asn Ala Gly Ala Gln Pro Ala Lys Leu His Ala Pro Ala Ala Ala
                85                  90                  95

Gly Ser Thr Val Thr Leu Asn Trp Thr Leu Trp Pro Asp Ser His Val
            100                 105                 110

Gly Pro Val Ile Thr Tyr Met Ala Arg Cys Pro Asp Ser Gly Cys Gln
        115                 120                 125

Asn Trp Ser Pro Gly Thr Gln Pro Val Trp Phe Lys Ile Lys Glu Gly
    130                 135                 140

Gly Arg Glu Gly Thr Ser Asn Val Trp Ala Ala Thr Pro Leu Met Lys
145                 150                 155                 160

Ala Pro Ser Ala Tyr Thr Tyr Thr Ile Pro Ala Cys Leu Lys Ser Gly
                165                 170                 175
```

-continued

```
Tyr Tyr Leu Val Arg His Glu Ile Ile Ala Leu His Ser Ala Trp Gln
            180                 185                 190

Tyr Pro Gly Ala Gln Phe Tyr Pro Gly Cys His Gln Leu Gln Val Thr
        195                 200                 205

Gly Gly Gly Ser Thr Val Pro Ser Ala Asn Leu Val Ala Phe Pro Gly
    210                 215                 220

Ala Tyr Lys Gly Ser Asp Pro Gly Ile Thr Tyr Asp Ala Tyr Lys Ala
225                 230                 235                 240

Gln Pro Tyr Thr Ile Pro Gly Pro Val Phe Thr Cys
            245                 250
```

<210> SEQ ID NO 13
<211> LENGTH: 924
<212> TYPE: DNA
<213> ORGANISM: Corynascus thermophilus

<400> SEQUENCE: 13

```
atgtaccgca cgctcggttc ccttgccctg ctcgctggag gcgctgctgc ccacggtgcc     60
gtgaccagct acaacatcgc gggcaaggac taccctgggt aaggaaggag atctctctct    120
ctctctctct ctctctctct ctctctctct ctcgttctct tgctaacaca aaggcacctc    180
tgcagatact cgggctttgc cccgaccggc gaacccgtca tccagtggca atggcccgac    240
tacaaccccg tcatgtccgc tagcgacttc aagctccgct gcaacggcgg caccaacgcg    300
cagctgtatg ctgaggcggc cccggcgat accatcacgg ccacctgggc ccagtggacg    360
cacgcccagg gccgatcct ggtgtggatg tacaagtgcc ccggcgactt cagctcctgc    420
gacggctccg gcgagggctg gttcaagatc gacgaggccg gcttccacgg cgacggccag    480
actgtcttcc tcgacagcga gaaccctcg gctgggaca tcgccaagct ggtcggcggc    540
aacaagtcgt ggagcagcaa gatccccgag ggcctcgctc cgggcaacta cctggtccgc    600
cacgagctca tcgccctgca ccaggccaac gcccgcagt tctacccga gtgcgcccag    660
gtcaaggtta ccggctccgg caccgccgag cccgactcct cgtacaaggc cgccatcccc    720
ggctactgct cgcagagcga ccccaacatt tcggtaagga gggactcccg gccgagagag    780
agagaggact cattcctggt gctaacccgt tcacttccgc agttcaacat caacgaccac    840
tccctcccgc aggagtacaa gatccccggc ccgccggtct tcaagggcac tgcctccgcc    900
aaggctcgct ccttccaggc ctaa                                          924
```

<210> SEQ ID NO 14
<211> LENGTH: 255
<212> TYPE: PRT
<213> ORGANISM: Corynascus thermophilus

<400> SEQUENCE: 14

```
Met Tyr Arg Thr Leu Gly Ser Leu Ala Leu Leu Ala Gly Gly Ala Ala
1               5                   10                  15

Ala His Gly Ala Val Thr Ser Tyr Asn Ile Ala Gly Lys Asp Tyr Pro
            20                  25                  30

Gly Tyr Ser Gly Phe Ala Pro Thr Gly Glu Pro Val Ile Gln Trp Gln
        35                  40                  45

Trp Pro Asp Tyr Asn Pro Val Met Ser Ala Ser Asp Phe Lys Leu Arg
    50                  55                  60

Cys Asn Gly Gly Thr Asn Ala Gln Leu Tyr Ala Glu Ala Ala Pro Gly
65                  70                  75                  80

Asp Thr Ile Thr Ala Thr Trp Ala Gln Trp Thr His Ala Gln Gly Pro
```

```
              85                  90                  95
Ile Leu Val Trp Met Tyr Lys Cys Pro Gly Asp Phe Ser Ser Cys Asp
            100                 105                 110

Gly Ser Gly Glu Gly Trp Phe Lys Ile Asp Glu Ala Gly Phe His Gly
        115                 120                 125

Asp Gly Gln Thr Val Phe Leu Asp Ser Glu Asn Pro Ser Gly Trp Asp
    130                 135                 140

Ile Ala Lys Leu Val Gly Gly Asn Lys Ser Trp Ser Ser Lys Ile Pro
145                 150                 155                 160

Glu Gly Leu Ala Pro Gly Asn Tyr Leu Val Arg His Glu Leu Ile Ala
            165                 170                 175

Leu His Gln Ala Asn Ala Pro Gln Phe Tyr Pro Glu Cys Ala Gln Val
        180                 185                 190

Lys Val Thr Gly Ser Gly Thr Ala Glu Pro Asp Ser Ser Tyr Lys Ala
    195                 200                 205

Ala Ile Pro Gly Tyr Cys Ser Gln Ser Asp Pro Asn Ile Ser Phe Asn
210                 215                 220

Ile Asn Asp His Ser Leu Pro Gln Glu Tyr Lys Ile Pro Gly Pro Pro
225                 230                 235                 240

Val Phe Lys Gly Thr Ala Ser Ala Lys Ala Arg Ser Phe Gln Ala
            245                 250                 255

<210> SEQ ID NO 15
<211> LENGTH: 742
<212> TYPE: DNA
<213> ORGANISM: Corynascus thermophilus

<400> SEQUENCE: 15
atgctggcga caaccttcgc tctcctgacg gccgctctcg gcgtcagcgc ccattatacc      60
ctcccccggg tcgggtccgg ctccgagtgg cagcacgtgc gccgggctga caactggcaa     120
aacaacggct tcgtcgacaa cgtctactcg cagcagatcc gctgcttcca gtcgagcaat     180
gccggcgccc cggatgtcta caccgtccag gcgggctcga gcgtgaccta ctacgccaac     240
cccagcatct accaccccgg ccccatgcag ttctacctcg cccgcgttcc ggacggacag     300
gacgtcaagt cgtggaacgg cgacggcgct gtgtggttca aggtgtacga ggagcagcct     360
cagttcggct cccagcttac ctggcctagc aacggtgcgt cgaccatgct ctctcgtttg     420
gcccgttgcc aggtgctaac tgtccttccc gtccgcaggc aagaactcgt tccaggttcc     480
catccccagc tgcatccgcc cgggcaagta cctcctccgc gccgagcaca tcgccctgca     540
cgttgcccag agccagggcg gtgcccagtt ctacatctcg tgcgcccagc tcgacgtcac     600
tggcggcggc agcaccgagc cttcccagaa ggttgccttc ccgggtgcct actcgcccac     660
cgaccccggc attctcatca acatcaactg gcccatcccg acctcgtaca agaaccccgg     720
cccgccggtc ttccgctgct aa                                              742

<210> SEQ ID NO 16
<211> LENGTH: 225
<212> TYPE: PRT
<213> ORGANISM: Corynascus thermophilus

<400> SEQUENCE: 16

Met Leu Ala Thr Thr Phe Ala Leu Leu Thr Ala Ala Leu Gly Val Ser
1               5                   10                  15

Ala His Tyr Thr Leu Pro Arg Val Gly Ser Gly Ser Glu Trp Gln His
            20                  25                  30
```

Val Arg Arg Ala Asp Asn Trp Gln Asn Asn Gly Phe Val Asp Asn Val
       35                  40                  45

Tyr Ser Gln Gln Ile Arg Cys Phe Gln Ser Ser Asn Ala Gly Ala Pro
 50                  55                  60

Asp Val Tyr Thr Val Gln Ala Gly Ser Ser Val Thr Tyr Tyr Ala Asn
 65                  70                  75                  80

Pro Ser Ile Tyr His Pro Gly Pro Met Gln Phe Tyr Leu Ala Arg Val
                 85                  90                  95

Pro Asp Gly Gln Asp Val Lys Ser Trp Asn Gly Asp Gly Ala Val Trp
                100                 105                 110

Phe Lys Val Tyr Glu Glu Gln Pro Gln Phe Gly Ser Gln Leu Thr Trp
            115                 120                 125

Pro Ser Asn Gly Lys Asn Ser Phe Gln Val Pro Ile Pro Ser Cys Ile
        130                 135                 140

Arg Pro Gly Lys Tyr Leu Leu Arg Ala Glu His Ile Ala Leu His Val
145                 150                 155                 160

Ala Gln Ser Gln Gly Gly Ala Gln Phe Tyr Ile Ser Cys Ala Gln Leu
                165                 170                 175

Asp Val Thr Gly Gly Ser Thr Glu Pro Ser Gln Lys Val Ala Phe
            180                 185                 190

Pro Gly Ala Tyr Ser Pro Thr Asp Pro Gly Ile Leu Ile Asn Ile Asn
        195                 200                 205

Trp Pro Ile Pro Thr Ser Tyr Lys Asn Pro Gly Pro Pro Val Phe Arg
    210                 215                 220

Cys
225

<210> SEQ ID NO 17
<211> LENGTH: 901
<212> TYPE: DNA
<213> ORGANISM: Corynascus thermophilus

<400> SEQUENCE: 17
atgaaggttc tcgcgcccct ggttctggcc ggcgccgcca gcgcccacac catcttcacg     60
tcgctcgagg tgggcggcgt caaccatggc gtcggccagg gcgtccgcgt gccgtcgtac    120
aacggcccga tcgaggacgt gacgtccaac tcgatcgcct gcaacggccc ccccaacccg    180
acgacgccga cggacaaggt gatcacggtc caggccggcc agacggtgac ggccatctgg    240
cggtacatgc tcagcaccac cggctcggcc cccaacgacg tcatggacag cagccacaag    300
ggcccgacca tggcctacct caagaaggtc ggcaacgcca ccaccgactc gggcgtcggc    360
ggcggctggt tcaagatcca ggaggacggg ctgaacaacg cgtctggg cacggagcgc     420 gtcatcaacg gccagggccg ccacaacatc aagatccccg agtgcatcgc cccggccag    480 tacctcctcc gcgccgagat gctcgccctg cacggagcct ccaactaccc cggcgcccag    540
ttctacatgg agtcgctca gctcaacagt acgtttgtcc acgagagacg gaaaaacaaa    600
acagaagcaa ggggaggcgg ggcagatgtg atggctaaca ttgatgcttt cttcttcagt    660
cgtcggcggc agcggcagca agaccccgtc accgtcagc ttcccgggtg cttacagcgt     720
acgttgttcc aaaaggcttt ttcttcgcgt tttttttttct ttgaactgat acagccccct   780
ctgtgacgac tactaacacg gccacaatca acagggcaac gaccccggtg tcaagatcaa    840
catctactgg cctcccgtca ccgaatacaa ggttcccggc ccagcgtctt tcacttgcta    900
a                                                                     901

<210> SEQ ID NO 18
<211> LENGTH: 237
<212> TYPE: PRT
<213> ORGANISM: Corynascus thermophilus

<400> SEQUENCE: 18

Met Lys Val Leu Ala Pro Leu Val Leu Ala Gly Ala Ala Ser Ala His
1               5                   10                  15

Thr Ile Phe Thr Ser Leu Glu Val Gly Val Asn His Gly Val Gly
            20                  25                  30

Gln Gly Val Arg Val Pro Ser Tyr Asn Gly Pro Ile Glu Asp Val Thr
        35                  40                  45

Ser Asn Ser Ile Ala Cys Asn Gly Pro Pro Asn Pro Thr Thr Pro Thr
50                  55                  60

Asp Lys Val Ile Thr Val Gln Ala Gly Gln Thr Val Thr Ala Ile Trp
65                  70                  75                  80

Arg Tyr Met Leu Ser Thr Thr Gly Ser Ala Pro Asn Asp Val Met Asp
                85                  90                  95

Ser Ser His Lys Gly Pro Thr Met Ala Tyr Leu Lys Lys Val Gly Asn
            100                 105                 110

Ala Thr Thr Asp Ser Gly Val Gly Gly Gly Trp Phe Lys Ile Gln Glu
        115                 120                 125

Asp Gly Leu Asn Asn Gly Val Trp Gly Thr Glu Arg Val Ile Asn Gly
    130                 135                 140

Gln Gly Arg His Asn Ile Lys Ile Pro Glu Cys Ile Ala Pro Gly Gln
145                 150                 155                 160

Tyr Leu Leu Arg Ala Glu Met Leu Ala Leu His Gly Ala Ser Asn Tyr
                165                 170                 175

Pro Gly Ala Gln Phe Tyr Met Glu Cys Ala Gln Leu Asn Ile Val Gly
            180                 185                 190

Gly Ser Gly Ser Lys Thr Pro Ser Thr Val Ser Phe Pro Gly Ala Tyr
        195                 200                 205

Ser Gly Asn Asp Pro Gly Val Lys Ile Asn Ile Tyr Trp Pro Pro Val
    210                 215                 220

Thr Glu Tyr Lys Val Pro Gly Pro Ser Val Phe Thr Cys
225                 230                 235

<210> SEQ ID NO 19
<211> LENGTH: 944
<212> TYPE: DNA
<213> ORGANISM: Corynascus thermophilus

<400> SEQUENCE: 19
atgaagctga gcgctgccat cgccgtgctc gcggccgccc ttgccgaggc gcactgtaag      60
ctggcttgcc ggtcctcccc cttctcaacg acgccgagct cgagcgcgtg ggactaatga    120
cgatgtgacg acgacatcaa gatacctttc ccagcatcgc caacacgccc gactggcagt    180
atgtgcgcat cacgaccaac taccagagca acggccccgt gacggacgtc aactcggacc    240
agatccgctg ctacgagcgc aacccgggca cgggcgcgcc cggcatctac aacgtcaccg    300
ccggcaccac catcaactac aacgccaagt cgtccatctc ccacccgggc cccatggcct    360
tctacatcgc caaggtcccc gccggccagt cggccgccac ctgggacggc aagggcgccg    420
tctggtccaa gatctaccag gagatgccgc actttggctc gagcctgacc tgggactcga    480
acggtatgat gagttctctc tctccttctc tctttgatgc tctccttgtg atgctaaacg    540

```
acgaccccg  ccaggccgcg  tctccatgcc  cgtcaccatc  ccccgctgtc  tgcagaacgg    600
cgagtacctg  ctgcgtgccg  agcacattgc  cctccacagc  gccggcagcg  tcggcggcgc    660
ccagttctac  atctcgtgcg  ctcagatctc  gggtatgcat  tatatacttc  catattgtcc    720
acccactcac  cccccatccc  ccacgcttaa  tagctcgagc  agcggaacca  tctgaagcta    780
acacgtcccc  cccagtcacc  ggcggcaccg  gcacctggaa  ccccgcaac   aaggtgtcct    840 tccccggcgc  ctacaaggcc  accgacccgg  gcatcctgat  caacatctac  tggcccatcc    900
cgaccagcta  cacgcccgcc  ggcccggccg  tcgacacctg  ctag                     944
```

<210> SEQ ID NO 20
<211> LENGTH: 227
<212> TYPE: PRT
<213> ORGANISM: Corynascus thermophilus

<400> SEQUENCE: 20

```
Met Lys Leu Ser Ala Ala Ile Ala Val Leu Ala Ala Leu Ala Glu
1               5                   10                  15

Ala His Tyr Thr Phe Pro Ser Ile Ala Asn Thr Pro Asp Trp Gln Tyr
                20                  25                  30

Val Arg Ile Thr Thr Asn Tyr Gln Ser Asn Gly Pro Val Thr Asp Val
                35                  40                  45

Asn Ser Asp Gln Ile Arg Cys Tyr Glu Arg Asn Pro Gly Thr Gly Ala
50                  55                  60

Pro Gly Ile Tyr Asn Val Thr Ala Gly Thr Thr Ile Asn Tyr Asn Ala
65                  70                  75                  80

Lys Ser Ser Ile Ser His Pro Gly Pro Met Ala Phe Tyr Ile Ala Lys
                85                  90                  95

Val Pro Ala Gly Gln Ser Ala Ala Thr Trp Asp Gly Lys Gly Ala Val
                100                 105                 110

Trp Ser Lys Ile Tyr Gln Glu Met Pro His Phe Gly Ser Ser Leu Thr
                115                 120                 125

Trp Asp Ser Asn Gly Arg Val Ser Met Pro Val Thr Ile Pro Arg Cys
130                 135                 140

Leu Gln Asn Gly Glu Tyr Leu Leu Arg Ala Glu His Ile Ala Leu His
145                 150                 155                 160

Ser Ala Gly Ser Val Gly Gly Ala Gln Phe Tyr Ile Ser Cys Ala Gln
                165                 170                 175

Ile Ser Val Thr Gly Gly Thr Gly Thr Trp Asn Pro Arg Asn Lys Val
                180                 185                 190

Ser Phe Pro Gly Ala Tyr Lys Ala Thr Asp Pro Gly Ile Leu Ile Asn
                195                 200                 205

Ile Tyr Trp Pro Ile Pro Thr Ser Tyr Thr Pro Ala Gly Pro Ala Val
        210                 215                 220

Asp Thr Cys
225
```

<210> SEQ ID NO 21
<211> LENGTH: 948
<212> TYPE: DNA
<213> ORGANISM: Corynascus thermophilus

<400> SEQUENCE: 21

```
atgtcttcct  tcacctccaa  gggcctcctt  tccgccctca  tgggcgctgc  cacggttgcc     60
gcccacggcc  acgtcaccaa  tatcgtcatc  aacggcgtct  cgtaccagaa  ctacgatccg    120
```

```
ttcagccacc cttacatgcg aaccccccg acggttgtcg gctggacggc gagcaacacg      180
gacaacggct tcgtcggccc cgagtccttc tctagcccgg acatcatctg ccacaagtcg      240
gccaccaacg ccggcggtca tgccgttgtt gccgccggcg acaagatttc catccagtgg      300
gacacctggc ccgagtcgca ccacggtccg gtcatcgact acctcgccga ctgcggcgac      360
gcgggctgcg agaaggtcga caagaccacg ctcgagttct tcaagatcag cgagaagggc      420
ctgatcgacg gcagcagcgc gcccggcagg tgggcgtccg acgagctgat cgccaacaac      480
aactcgtggc tggtccagat cccgccccgac atcgcccccg gcaactacgt cctgcgccac      540
gagatcatcg ccctgcacag cgccggccag cagaacggcg cgcagaacta cccccagtgc      600
gtcaacctgc acatcaccgg ctccggcacc cggaaaccct cgggcgtccc cggcaccgag      660
ctctaccggc cgaccgaccc cggcatcctg ccaacatct acacctcccc cgtcgcctac      720
cagatccccg gcccggccat catccccggc gcctccgccg tcgagcagac cacctcggcc      780
atcaccgcct ccgccagcgc ggttcttccc ggcttcgcta ccgccgcgcc ccggctgcg      840 accaccacaa ccaccaccgc ctccgctacc agtgctcccc gcccgaccgg ctgtgccggt      900
ctgaggaagc gccgtcgcca cgcccgtgat gtcaaggttg ccctctag                   948
```

<210> SEQ ID NO 22
<211> LENGTH: 315
<212> TYPE: PRT
<213> ORGANISM: Corynascus thermophilus

<400> SEQUENCE: 22

```
Met Ser Ser Phe Thr Ser Lys Gly Leu Leu Ser Ala Leu Met Gly Ala
1               5                   10                  15

Ala Thr Val Ala Ala His Gly His Val Thr Asn Ile Val Ile Asn Gly
                20                  25                  30

Val Ser Tyr Gln Asn Tyr Asp Pro Phe Ser His Pro Tyr Met Arg Asn
            35                  40                  45

Pro Pro Thr Val Val Gly Trp Thr Ala Ser Asn Thr Asp Asn Gly Phe
        50                  55                  60

Val Gly Pro Glu Ser Phe Ser Pro Asp Ile Ile Cys His Lys Ser
65                  70                  75                  80

Ala Thr Asn Ala Gly Gly His Ala Val Val Ala Ala Gly Asp Lys Ile
                85                  90                  95

Ser Ile Gln Trp Asp Thr Trp Pro Glu Ser His His Gly Pro Val Ile
            100                 105                 110

Asp Tyr Leu Ala Asp Cys Gly Asp Ala Gly Cys Glu Lys Val Asp Lys
        115                 120                 125

Thr Thr Leu Glu Phe Phe Lys Ile Ser Glu Lys Gly Leu Ile Asp Gly
    130                 135                 140

Ser Ser Ala Pro Gly Arg Trp Ala Ser Asp Glu Leu Ile Ala Asn Asn
145                 150                 155                 160

Asn Ser Trp Leu Val Gln Ile Pro Pro Asp Ile Ala Pro Gly Asn Tyr
                165                 170                 175

Val Leu Arg His Glu Ile Ile Ala Leu His Ser Ala Gly Gln Gln Asn
            180                 185                 190

Gly Ala Gln Asn Tyr Pro Gln Cys Val Asn Leu His Ile Thr Gly Ser
        195                 200                 205

Gly Thr Arg Lys Pro Ser Gly Val Pro Gly Thr Glu Leu Tyr Arg Pro
    210                 215                 220
```

Thr Asp Pro Gly Ile Leu Ala Asn Ile Tyr Thr Ser Pro Val Ala Tyr
225                 230                 235                 240

Gln Ile Pro Gly Pro Ala Ile Ile Pro Gly Ala Ser Ala Val Glu Gln
            245                 250                 255

Thr Thr Ser Ala Ile Thr Ala Ser Ala Ser Val Leu Pro Gly Phe
        260                 265                 270

Ala Thr Ala Ala Pro Pro Ala Ala Thr Thr Thr Thr Thr Ala Ser
        275                 280                 285

Ala Thr Ser Ala Pro Arg Pro Thr Gly Cys Ala Gly Leu Arg Lys Arg
        290                 295                 300

Arg Arg His Ala Arg Asp Val Lys Val Ala Leu
305                 310                 315

<210> SEQ ID NO 23
<211> LENGTH: 1380
<212> TYPE: DNA
<213> ORGANISM: Corynascus thermophilus

<400> SEQUENCE: 23

```
atgcatcctc ccatctttgt tcttgggctt gcgagcctgc tttgccccct ctcgtctgca      60
cacactactt tcaccaccct cttcatcaat gatgtcaacc aaggtgacgg aacctgcatt     120
cgcatggcga aggagggcaa cgtcgctact catcctctcg cgggcggcct cgactctgaa     180
gacatggcct gtggtacgtt gacacgtcct tgaccccgcc gagactgtcc cgtgtatcta     240
aacttctcat caggccggga tggccaagaa cccgttgcat ttacctgccc ggccccagct     300
ggtgccaagt tgaccttcga gtttcgcatg tgggccgacg cttcgcagcc cggatcgatc     360
gacccgtccc atcttggcgc tatggccatc tacctcaaga aggtttctaa catgaaatct     420
gacgcggccg ctgggccggg ctggttcaag atttgggacc aaggctacga cacggaggcc     480
aagaagtggg ccaccgagaa tctcattgag aacaacggcc tgctgagcgt caaccttccc     540
tcgggcttgt cgaccggcta ctacctcgtc cgtcaggaga ccattacctt ccaaaacgtc     600
accaatgaca tgccagatcc ccagttctac gtcggttgcg cgcagctcta cgtcgaaggc     660
acctcggact cacccatccc cccagacaag accgtctcca ttcccggcca catcagcgac     720
ccggccgacc cgggcctgac cttaacatc tacacgacg acgtgtccgc ctacaagccc     780
cccggcccgg aggtttactt ccccaccgcc atcacctcct ccggaagcag cgacgacagg     840
ggggccgcgc gccagcagac tcccgccgac aagcaggccg agaaggcct cgttcccacc     900
gactgcgtcg tcaagaacgc aaactggtgc gccgccgccc tgccgcccta caccgacgag     960
gccggctgct gggccgccgt ggaggactgc aacaggcagc tggacgagtg ctacaccagc    1020
gcgccccct cgggcagcag ggggtgcaag atctgggagg agcaggtatg catcgtcgtc    1080
tcgcggaagt gcgaggcccg ggatttccag cccctcccgc ggctgtggaa ggatctaaga    1140
gagggaattg atgagccgat cccgggtggg aagttgcctc cggcgctcaa cgcgggagag    1200
agcgggatc atggcggaag aggctgcggc caccatggtg gcgaggagga ggctggggct    1260
ggggcggcct ccactcctgc ttttgctgct ccccatgcgg ccaggattca aacccaaat    1320
ttcaagaggg gccggcgccg tgagtcgcgt tggcggcgac tggcatctgg tgagcaatag    1380
```

<210> SEQ ID NO 24
<211> LENGTH: 439
<212> TYPE: PRT
<213> ORGANISM: Corynascus thermophilus

<400> SEQUENCE: 24

-continued

```
Met His Pro Pro Ile Phe Val Leu Gly Leu Ala Ser Leu Leu Cys Pro
1               5                   10                  15

Leu Ser Ser Ala His Thr Thr Phe Thr Thr Leu Phe Ile Asn Asp Val
            20                  25                  30

Asn Gln Gly Asp Gly Thr Cys Ile Arg Met Ala Lys Glu Gly Asn Val
            35                  40                  45

Ala Thr His Pro Leu Ala Gly Leu Asp Ser Glu Asp Met Ala Cys
50                  55                  60

Gly Arg Asp Gly Gln Glu Pro Val Ala Phe Thr Cys Pro Ala Pro Ala
65                  70                  75                  80

Gly Ala Lys Leu Thr Phe Glu Phe Arg Met Trp Ala Asp Ala Ser Gln
                85                  90                  95

Pro Gly Ser Ile Asp Pro Ser His Leu Gly Ala Met Ala Ile Tyr Leu
                100                 105                 110

Lys Lys Val Ser Asn Met Lys Ser Asp Ala Ala Gly Pro Gly Trp
            115                 120                 125

Phe Lys Ile Trp Asp Gln Gly Tyr Asp Thr Glu Ala Lys Lys Trp Ala
            130                 135                 140

Thr Glu Asn Leu Ile Glu Asn Asn Gly Leu Leu Ser Val Asn Leu Pro
145                 150                 155                 160

Ser Gly Leu Ser Thr Gly Tyr Tyr Leu Val Arg Gln Glu Thr Ile Thr
                165                 170                 175

Phe Gln Asn Val Thr Asn Asp Met Pro Asp Pro Gln Phe Tyr Val Gly
                180                 185                 190

Cys Ala Gln Leu Tyr Val Glu Gly Thr Ser Asp Ser Pro Ile Pro Pro
                195                 200                 205

Asp Lys Thr Val Ser Ile Pro Gly His Ile Ser Asp Pro Ala Asp Pro
            210                 215                 220

Gly Leu Thr Phe Asn Ile Tyr Thr Asp Asp Val Ser Ala Tyr Lys Pro
225                 230                 235                 240

Pro Gly Pro Glu Val Tyr Phe Pro Thr Ala Ile Thr Ser Ser Gly Ser
                245                 250                 255

Ser Asp Asp Arg Gly Ala Ala Arg Gln Gln Thr Pro Ala Asp Lys Gln
            260                 265                 270

Ala Gly Glu Gly Leu Val Pro Thr Asp Cys Val Val Lys Asn Ala Asn
            275                 280                 285

Trp Cys Ala Ala Ala Leu Pro Pro Tyr Thr Asp Glu Ala Gly Cys Trp
            290                 295                 300

Ala Ala Val Glu Asp Cys Asn Arg Gln Leu Asp Glu Cys Tyr Thr Ser
305                 310                 315                 320

Ala Pro Pro Ser Gly Ser Arg Gly Cys Lys Ile Trp Glu Glu Gln Val
                325                 330                 335

Cys Ile Val Val Ser Arg Lys Cys Glu Ala Arg Asp Phe Gln Pro Leu
            340                 345                 350

Pro Arg Leu Trp Lys Asp Leu Arg Glu Gly Ile Asp Glu Pro Ile Pro
            355                 360                 365

Gly Gly Lys Leu Pro Pro Ala Leu Asn Ala Gly Glu Ser Gly Asp His
            370                 375                 380

Gly Gly Arg Gly Cys Gly His His Gly Gly Glu Glu Ala Gly Ala
385                 390                 395                 400

Gly Ala Ala Ser Thr Pro Ala Phe Ala Ala Pro His Ala Ala Arg Ile
                405                 410                 415
```

His Asn Pro Asn Phe Lys Arg Gly Arg Arg Glu Ser Arg Trp Arg
            420                 425                 430

Arg Leu Ala Ser Gly Glu Gln
        435

<210> SEQ ID NO 25
<211> LENGTH: 821
<212> TYPE: DNA
<213> ORGANISM: Corynascus thermophilus

<400> SEQUENCE: 25

| | | | | | |
|---|---|---|---|---|---|
| atgaagctct | ctctcttttc | cgtcctggcc | gctgccctca | ccgtcgaggg | gcatgccatc | 60 |
| ttccagaagg | tctccgtcaa | cggggcggac | cagggctccc | tcaccggcct | ccgcgctccc | 120 |
| aacaacaaca | acccggtgca | ggatgtcagc | agccaggaca | tgatctgcgg | ccagccggga | 180 |
| tcgacgtcga | gcacggtcat | cgaggtcaag | gccggcgaca | ggatcggcgc | ctggtaccag | 240 |
| cacgtcatcg | gcggtgccca | gttccccggc | gaccctgaca | acccgatcgc | cgcgtcgcac | 300 |
| aagggccccg | tcatggccta | cctcgccaag | gttgacaatg | ccgcaaccgc | cgacaagacg | 360 |
| ggcctgcagt | ggtatgtgtt | cccgccgccc | gagggacgtc | agcttggggc | aagtcgcgtc | 420 |
| tgaccgggct | cgcttctttc | tctctgtata | ggttcaagat | ctgggaggac | acctttgatc | 480 |
| ccagcagcaa | gacctggggt | gtcgacaacc | tcatcaacaa | caacggctgg | gtgtacttca | 540 |
| acatcccgca | gtgcatcgcc | gacgccact | acctcctccg | ggttgaggtc | ctcgccctgc | 600 |
| actcggccta | ccagaccggc | ggggctcagt | tctaccagtc | ctgcgcccag | atcagcgtgt | 660 |
| ccggcggcgg | ctccttcacg | ccgtcgtcga | ctgtgagctt | cccgggcgcc | tacaacgcca | 720 |
| acgaccccgg | catcacgatc | aacatctacg | gcgctaccgg | tcagcccgac | aacaacggcc | 780 |
| agccgtacac | tgcccctggc | cccgcgccca | tctcctgctg | a | | 821 |

<210> SEQ ID NO 26
<211> LENGTH: 246
<212> TYPE: PRT
<213> ORGANISM: Corynascus thermophilus

<400> SEQUENCE: 26

Met Lys Leu Ser Leu Phe Ser Val Leu Ala Ala Ala Leu Thr Val Glu
1               5                   10                  15

Gly His Ala Ile Phe Gln Lys Val Ser Val Asn Gly Ala Asp Gln Gly
            20                  25                  30

Ser Leu Thr Gly Leu Arg Ala Pro Asn Asn Asn Pro Val Gln Asp
        35                  40                  45

Val Ser Ser Gln Asp Met Ile Cys Gly Gln Pro Gly Ser Thr Ser Ser
    50                  55                  60

Thr Val Ile Glu Val Lys Ala Gly Asp Arg Ile Gly Ala Trp Tyr Gln
65                  70                  75                  80

His Val Ile Gly Gly Ala Gln Phe Pro Gly Asp Pro Asn Pro Ile
                85                  90                  95

Ala Ala Ser His Lys Gly Pro Val Met Ala Tyr Leu Ala Lys Val Asp
            100                 105                 110

Asn Ala Ala Thr Ala Asp Lys Thr Gly Leu Gln Trp Phe Lys Ile Trp
        115                 120                 125

Glu Asp Thr Phe Asp Pro Ser Ser Lys Thr Trp Gly Val Asp Asn Leu
    130                 135                 140

Ile Asn Asn Asn Gly Trp Val Tyr Phe Asn Ile Pro Gln Cys Ile Ala
145                 150                 155                 160

```
Asp Gly His Tyr Leu Leu Arg Val Glu Val Leu Ala Leu His Ser Ala
            165                 170                 175

Tyr Gln Thr Gly Gly Ala Gln Phe Tyr Gln Ser Cys Ala Gln Ile Ser
        180                 185                 190

Val Ser Gly Gly Ser Phe Thr Pro Ser Ser Thr Val Ser Phe Pro
        195                 200                 205

Gly Ala Tyr Asn Ala Asn Asp Pro Gly Ile Thr Ile Asn Ile Tyr Gly
    210                 215                 220

Ala Thr Gly Gln Pro Asp Asn Asn Gly Gln Pro Tyr Thr Ala Pro Gly
225                 230                 235                 240

Pro Ala Pro Ile Ser Cys
            245
```

<210> SEQ ID NO 27
<211> LENGTH: 1125
<212> TYPE: DNA
<213> ORGANISM: Corynascus thermophilus

<400> SEQUENCE: 27

```
atgaagtcct tcaccctcac cgccctggcc gccctggccg caacgccgc cgcccacgcg      60
accttccagg ccctctgggt cgacggcgtc gactacggct cgcagtgcgc ccgtcttccc     120
ggatccaact ccccgatcac cgacgtgagc tcgacggcca tccgctgcaa tgccaacgcc     180
ggccgcgccc agggcaagtg cccggtcaag gccggctcga ccgtgacgat cgagatgcac     240
caggtatgtt ccactaaaag gaggaaaaga aaaaaaacag agtggaacgg tcaggctgac     300
tgaggctctc tcgctacgat cagcaacccg gtgaccggtc gtgcggcagc gacgccatcg     360
gcggcgccca ccacggcccc gtcctcgtgt acatgtccaa ggtgtcggat gcggcgtcgg     420
ccgacggctc gtccggctgg ttcaaggtgt cgaggacgc ctgggccaag aacccgtcgg     480
gcggctccgg cgacgacgac tactgggca ccaaggacct caacgcctgc tgcggcaaga     540
tgaacgtcaa gatcccgtcc gacctgccgt cgggcgacta cctgctccgt gccgaggcca     600
tcgccctgca cacggccggc ggctcgggcg cgcccagtt ctacatcacc tgctaccagc     660
tcaccgtcga gggttccggc aacgccagcc cggccaccgt ctccttccct ggcgcctaca     720
aggcctccga cccgggcatc ctggtcaaca tccacgccgc catgtccggc tacaccgtgc     780
ccggccgtc cgtctactcg gcggcagca ccaagaaggc cggcagcggc tgctccggct     840
gcgaggccac ctgcgccgtc ggctctagcc ccagcgccac cgtcacctcg tcgcccggca     900
gccagcccac ctcccccggc ggcggcgacg gcggcggctg caccgtcccc aagtaccagc     960
agtgcggtgg ccagggctac agcggctgca ccaactgcga ggtgagttcc cctgcttact    1020
tgttgtcctc tgtacccctt ccatgttttc gatgctgact ttctgcgtta gtctggctct    1080
acttgcagcg ccgtctcgcc gccgtactac taccagtgcg tgtaa                    1125
```

<210> SEQ ID NO 28
<211> LENGTH: 324
<212> TYPE: PRT
<213> ORGANISM: Corynascus thermophilus

<400> SEQUENCE: 28

```
Met Lys Ser Phe Thr Leu Thr Ala Leu Ala Ala Leu Ala Gly Asn Ala
1               5                   10                  15

Ala Ala His Ala Thr Phe Gln Ala Leu Trp Val Asp Gly Val Asp Tyr
            20                  25                  30
```

Gly Ser Gln Cys Ala Arg Leu Pro Gly Ser Asn Ser Pro Ile Thr Asp
                35                  40                  45

Val Ser Ser Thr Ala Ile Arg Cys Asn Ala Asn Ala Gly Arg Ala Gln
 50                  55                  60

Gly Lys Cys Pro Val Lys Ala Gly Ser Thr Val Thr Ile Glu Met His
 65                  70                  75                  80

Gln Gln Pro Gly Asp Arg Ser Cys Gly Ser Asp Ala Ile Gly Ala
                 85                  90                  95

His His Gly Pro Val Leu Val Tyr Met Ser Lys Val Ser Asp Ala Ala
                100                 105                 110

Ser Ala Asp Gly Ser Ser Gly Trp Phe Lys Val Phe Glu Asp Gly Trp
                115                 120                 125

Ala Lys Asn Pro Ser Gly Gly Ser Gly Asp Asp Tyr Trp Gly Thr
130                 135                 140

Lys Asp Leu Asn Ala Cys Cys Gly Lys Met Asn Val Lys Ile Pro Ser
145                 150                 155                 160

Asp Leu Pro Ser Gly Asp Tyr Leu Leu Arg Ala Glu Ala Ile Ala Leu
                165                 170                 175

His Thr Ala Gly Gly Ser Gly Gly Ala Gln Phe Tyr Ile Thr Cys Tyr
                180                 185                 190

Gln Leu Thr Val Glu Gly Ser Gly Asn Ala Ser Pro Ala Thr Val Ser
                195                 200                 205

Phe Pro Gly Ala Tyr Lys Ala Ser Asp Pro Gly Ile Leu Val Asn Ile
        210                 215                 220

His Ala Ala Met Ser Gly Tyr Thr Val Pro Gly Pro Ser Val Tyr Ser
225                 230                 235                 240

Gly Gly Ser Thr Lys Lys Ala Gly Ser Gly Cys Ser Gly Cys Glu Ala
                245                 250                 255

Thr Cys Ala Val Gly Ser Ser Pro Ser Ala Thr Val Thr Ser Ser Pro
                260                 265                 270

Gly Ser Gln Pro Thr Ser Pro Gly Gly Gly Asp Gly Gly Gly Cys Thr
                275                 280                 285

Val Pro Lys Tyr Gln Gln Cys Gly Gly Gln Gly Tyr Ser Gly Cys Thr
                290                 295                 300

Asn Cys Glu Ser Gly Ser Thr Cys Ser Ala Val Ser Pro Pro Tyr Tyr
305                 310                 315                 320

Tyr Gln Cys Val

<210> SEQ ID NO 29
<211> LENGTH: 1037
<212> TYPE: DNA
<213> ORGANISM: Corynascus thermophilus

<400> SEQUENCE: 29
atgaagtcgt tcacctcagc cttgttcgcc gctgggctcc ttgctcagca tgccgcagcc      60
cactccatct tccagcaggc aagcagcggc tcgatcgact cgacacgct gtgcacccgg     120 atgccggtca gtcccgaggg cccttgggtg atggatcatc tgcccataga cttgttaccg     180
acgagctgac gggttctcgt tattaatagc caacaatag ccctgtcact agcgtgacca     240
gcggcgacat gacctgcaac gtcggcggca ccaacggagt gtcgggcttc tgcgaggtga     300
acggtatggt ttcccgagtt ttcgaccagt cccccgtttt gattttttacc gccgcctgac    360 acgtgggctt cttgcttcgc tccttcggct agccggcgac gagttacgg ttgagatgca     420 cgcgcagccc ggcgaccgct cgtgcgacaa cgaggccatc ggcgggaacc acttcggccc    480

```
ggtcctcatc tacatgagca aggtcgacga cgcctcgact gccgacgggt ccggcgactg    540
gttcaaggtg acgagttcg gctacgaccc gagcaccaag acctgggca ccgacaagct     600 caacgagaac tgcggcaagc gcactttcaa gatccccgc aacatccctg cgggcgacta    660
tctcgtccgg gccgaggcca tcgcgctgca cactgccagc cagccgggcg cgcgcagtt    720 ctacatgagc tgctatgtaa gtttctagag tctctctctc tctctcgctt tctctctctc    780
gctcgccccg tctctccatt tgtcttcgtt cttccttttc ccttccttca aatgatgtct    840
ccccgctaac tttctctctc cccacaactt agcaagtccg gatttccggc ggcaacggag    900
gccagctgcc tgccggagtc aagatcccgg gcgcgtacag tgccaacgac cccggtatcc    960
tcatcgacat ctggggcaac gacttcaacg agtacatcat cccgggcccg cccgttatcg   1020
acagcagcta cttctaa                                                  1037
```

```
<210> SEQ ID NO 30
<211> LENGTH: 242
<212> TYPE: PRT
<213> ORGANISM: Corynascus thermophilus

<400> SEQUENCE: 30
```

Met Lys Ser Phe Thr Ser Ala Leu Phe Ala Ala Gly Leu Leu Ala Gln
1               5                   10                  15

His Ala Ala His Ser Ile Phe Gln Gln Ala Ser Ser Gly Ser Ile
            20                  25                  30

Asp Phe Asp Thr Leu Cys Thr Arg Met Pro Pro Asn Asn Ser Pro Val
        35                  40                  45

Thr Ser Val Thr Ser Gly Asp Met Thr Cys Asn Val Gly Gly Thr Asn
    50                  55                  60

Gly Val Ser Gly Phe Cys Glu Val Asn Ala Gly Asp Glu Phe Thr Val
65                  70                  75                  80

Glu Met His Ala Gln Pro Gly Asp Arg Ser Cys Asp Asn Glu Ala Ile
                85                  90                  95

Gly Gly Asn His Phe Gly Pro Val Leu Ile Tyr Met Ser Lys Val Asp
            100                 105                 110

Asp Ala Ser Thr Ala Asp Gly Ser Gly Asp Trp Phe Lys Val Asp Glu
        115                 120                 125

Phe Gly Tyr Asp Pro Ser Thr Lys Thr Trp Gly Thr Asp Lys Leu Asn
    130                 135                 140

Glu Asn Cys Gly Lys Arg Thr Phe Lys Ile Pro Arg Asn Ile Pro Ala
145                 150                 155                 160

Gly Asp Tyr Leu Val Arg Ala Glu Ala Ile Ala Leu His Thr Ala Ser
                165                 170                 175

Gln Pro Gly Gly Ala Gln Phe Tyr Met Ser Cys Tyr Gln Val Arg Ile
            180                 185                 190

Ser Gly Gly Asn Gly Gly Gln Leu Pro Ala Gly Val Lys Ile Pro Gly
        195                 200                 205

Ala Tyr Ser Ala Asn Asp Pro Gly Ile Leu Ile Asp Ile Trp Gly Asn
    210                 215                 220

Asp Phe Asn Glu Tyr Ile Ile Pro Gly Pro Val Ile Asp Ser Ser
225                 230                 235                 240

Tyr Phe

```
<210> SEQ ID NO 31
<211> LENGTH: 1200
```

```
<212> TYPE: DNA
<213> ORGANISM: Corynascus thermophilus

<400> SEQUENCE: 31
atgaaggcct ttagcctcgt cgccctggcg acggccgtga gcggccatac catcttccag     60
cgggtgtcgg tcaacgggca agaccagggc cagctcaagg gcgtgcgggc gccgtcgagc    120
aacttcccga tccagaacgt caacgattcc aacttcgcct gcaacgcaaa catcgtgtac    180
aaggacgaca ccatcatcaa gatccccgcg ggagcccgcg tgggttcgtg gtggcagcac    240
gtcatcggcg gcccgcaggg ctccaacgac ccggacaacc cgatcgccgc ctcccacaag    300
ggtatgctga tggcgaac caacccgcgc ccccttccc ccctcaacc tcccggaaca        360 cgcgtagctg acgggcaaat ccaggcccca tccaggtcta cctggccaag gttgacaacg    420
cggcgacagc gtcgcccacg ggcctcaggt ggttcaaggt tgccgagcgc gggctgaaca    480
acggcgtgtg gcggtcgac gagctcatcg ccaacaacgg ctggcactac ttcgacctgc    540
cgtcgtgcgt ggccccggc cagtacctga tgcgcgtcga gctgctcgcc ctgcacagcg    600
cctcgagccc cggcggcgcc cagttctaca tgggctgcgc ccagatcgaa ggtgggtgca    660
attctcgttc tgcttccccg tcccttccgg cccttcttt ctctctctcc ccttgtgctt     720
tcttcgctcc ttgacgaacc cgaggaaaga gggaagagga agaggaaag agggaggaaa    780 cggggcggag agacagacgg gatcgaatga gagagacaag acaagatcgg ctgacgagga    840
caaccagtca ccggctcggg cacccacacg ggctccgact tcgtctcgtt cccgggcgcc    900
tactcggcca cgacccgggg catcctgctg agcatctacg actcctcggg caagcccacc    960
aacggcgggc gggcgtacca gatccccggc ccgcgcccca tctcgtgctc gggcggcagc   1020
aacggcggcg gtgacaacgg cggcggcgac aacggcggcg gcaacaacgg cggcggcaac   1080
agcggcggca ccgtccccct ctacggccag tgcggcggca acggatacac cggcccgacc   1140
acctgcgccg agggaacctg caaggtgtcg aacgagtggt acagccagtg cctcccctag   1200

<210> SEQ ID NO 32
<211> LENGTH: 306
<212> TYPE: PRT
<213> ORGANISM: Corynascus thermophilus

<400> SEQUENCE: 32

Met Lys Ala Phe Ser Leu Val Ala Leu Ala Thr Ala Val Ser Gly His
1               5                   10                  15

Thr Ile Phe Gln Arg Val Ser Val Asn Gly Gln Asp Gln Gly Gln Leu
            20                  25                  30

Lys Gly Val Arg Ala Pro Ser Ser Asn Phe Pro Ile Gln Asn Val Asn
        35                  40                  45

Asp Ser Asn Phe Ala Cys Asn Ala Asn Ile Val Tyr Lys Asp Asp Thr
    50                  55                  60

Ile Ile Lys Ile Pro Ala Gly Ala Arg Val Gly Ser Trp Trp Gln His
65                  70                  75                  80

Val Ile Gly Gly Pro Gln Gly Ser Asn Asp Pro Asp Asn Pro Ile Ala
                85                  90                  95

Ala Ser His Lys Gly Pro Ile Gln Val Tyr Leu Ala Lys Val Asp Asn
            100                 105                 110

Ala Ala Thr Ala Ser Pro Thr Gly Leu Arg Trp Phe Lys Val Ala Glu
        115                 120                 125

Arg Gly Leu Asn Asn Gly Val Trp Ala Val Asp Glu Leu Ile Ala Asn
    130                 135                 140
```

-continued

```
Asn Gly Trp His Tyr Phe Asp Leu Pro Ser Cys Val Ala Pro Gly Gln
145                 150                 155                 160
Tyr Leu Met Arg Val Glu Leu Leu Ala Leu His Ser Ala Ser Ser Pro
            165                 170                 175
Gly Gly Ala Gln Phe Tyr Met Gly Cys Ala Gln Ile Glu Val Thr Gly
        180                 185                 190
Ser Gly Thr His Thr Gly Ser Asp Phe Val Ser Phe Pro Gly Ala Tyr
        195                 200                 205
Ser Ala Asn Asp Pro Gly Ile Leu Leu Ser Ile Tyr Asp Ser Ser Gly
        210                 215                 220
Lys Pro Thr Asn Gly Gly Arg Ala Tyr Gln Ile Pro Gly Pro Arg Pro
225                 230                 235                 240
Ile Ser Cys Ser Gly Gly Ser Asn Gly Gly Asp Asn Gly Gly
                245                 250                 255
Asp Asn Gly Gly Gly Asn Asn Gly Gly Asn Ser Gly Gly Thr Val
            260                 265                 270
Pro Leu Tyr Gly Gln Cys Gly Gly Asn Gly Tyr Thr Gly Pro Thr Thr
            275                 280                 285
Cys Ala Glu Gly Thr Cys Lys Val Ser Asn Glu Trp Tyr Ser Gln Cys
290                 295                 300
Leu Pro
305
```

<210> SEQ ID NO 33
<211> LENGTH: 37
<212> TYPE: DNA
<213> ORGANISM: Corynascus thermophilus

<400> SEQUENCE: 33
acacaactgg ggatccacca tgcccctcc acggcta                            37

<210> SEQ ID NO 34
<211> LENGTH: 41
<212> TYPE: DNA
<213> ORGANISM: Corynascus thermophilus

<400> SEQUENCE: 34
gtcaccctct agatctgcaa gtacccaggt aaggagcagt g                      41

<210> SEQ ID NO 35
<211> LENGTH: 40
<212> TYPE: DNA
<213> ORGANISM: Corynascus thermophilus

<400> SEQUENCE: 35
acacaactgg ggatccacca tggctccatt aacgtccgca                        40

<210> SEQ ID NO 36
<211> LENGTH: 35
<212> TYPE: DNA
<213> ORGANISM: Corynascus thermophilus

<400> SEQUENCE: 36
gtcaccctct agatctctcc acgatgtcgc cgttc                             35

<210> SEQ ID NO 37
<211> LENGTH: 41
<212> TYPE: DNA
<213> ORGANISM: Corynascus thermophilus

```
<400> SEQUENCE: 37
acacaactgg ggatccacca tgaaatacgc cctccagctc g                          41

<210> SEQ ID NO 38
<211> LENGTH: 41
<212> TYPE: DNA
<213> ORGANISM: Corynascus thermophilus

<400> SEQUENCE: 38
gtcaccctct agatctcatc cattctgtcg aaaatccctt g                          41

<210> SEQ ID NO 39
<211> LENGTH: 42
<212> TYPE: DNA
<213> ORGANISM: Corynascus thermophilus

<400> SEQUENCE: 39
acacaactgg ggatccacca tgaaggccct ctctctcctt gc                         42

<210> SEQ ID NO 40
<211> LENGTH: 38
<212> TYPE: DNA
<213> ORGANISM: Corynascus thermophilus

<400> SEQUENCE: 40
gtcaccctct agatctactg cgctcaaacg accaagtc                              38

<210> SEQ ID NO 41
<211> LENGTH: 37
<212> TYPE: DNA
<213> ORGANISM: Corynascus thermophilus

<400> SEQUENCE: 41
acacaactgg ggatccacca tgaaaacgct tgccgcc                               37

<210> SEQ ID NO 42
<211> LENGTH: 39
<212> TYPE: DNA
<213> ORGANISM: Corynascus thermophilus

<400> SEQUENCE: 42
gtcaccctct agatctcaaa tagacggctt ccccttctg                             39

<210> SEQ ID NO 43
<211> LENGTH: 36
<212> TYPE: DNA
<213> ORGANISM: Corynascus thermophilus

<400> SEQUENCE: 43
acacaactgg ggatccacca tgtaccgcac gctcgg                                36

<210> SEQ ID NO 44
<211> LENGTH: 39
<212> TYPE: DNA
<213> ORGANISM: Corynascus thermophilus

<400> SEQUENCE: 44
gtcaccctct agatctcgtt gcccaatagc ttgtcaaac                             39

<210> SEQ ID NO 45
<211> LENGTH: 38
<212> TYPE: DNA
```

<213> ORGANISM: Corynascus thermophilus

<400> SEQUENCE: 45
acacaactgg ggatccacca tgctggcgac aaccttcg                              38

<210> SEQ ID NO 46
<211> LENGTH: 37
<212> TYPE: DNA
<213> ORGANISM: Corynascus thermophilus

<400> SEQUENCE: 46
gtcaccctct agatctcgac cacctcaact tgtggtg                               37

<210> SEQ ID NO 47
<211> LENGTH: 37
<212> TYPE: DNA
<213> ORGANISM: Corynascus thermophilus

<400> SEQUENCE: 47
acacaactgg ggatccacca tgaaggttct cgcgccc                               37

<210> SEQ ID NO 48
<211> LENGTH: 42
<212> TYPE: DNA
<213> ORGANISM: Corynascus thermophilus

<400> SEQUENCE: 48
gtcaccctct agatctagag agagagatac cgcgacgatg ag                         42

<210> SEQ ID NO 49
<211> LENGTH: 36
<212> TYPE: DNA
<213> ORGANISM: Corynascus thermophilus

<400> SEQUENCE: 49
acacaactgg ggatccacca tgaagctgag cgctgc                                36

<210> SEQ ID NO 50
<211> LENGTH: 34
<212> TYPE: DNA
<213> ORGANISM: Corynascus thermophilus

<400> SEQUENCE: 50
gtcaccctct agatctttgt cgcttctcgg ctcg                                  34

<210> SEQ ID NO 51
<211> LENGTH: 42
<212> TYPE: DNA
<213> ORGANISM: Corynascus thermophilus

<400> SEQUENCE: 51
acacaactgg ggatccacca tgtcttcctt cacctccaag gg                         42

<210> SEQ ID NO 52
<211> LENGTH: 45
<212> TYPE: DNA
<213> ORGANISM: Corynascus thermophilus

<400> SEQUENCE: 52
gtcaccctct agatctgtga acgatatcta cgaataactc ggttg                      45

<210> SEQ ID NO 53
<211> LENGTH: 44

```
<212> TYPE: DNA
<213> ORGANISM: Corynascus thermophilus

<400> SEQUENCE: 53
acacaactgg ggatccacca tgcatcctcc catctttgtt cttg                    44

<210> SEQ ID NO 54
<211> LENGTH: 39
<212> TYPE: DNA
<213> ORGANISM: Corynascus thermophilus

<400> SEQUENCE: 54
gtcaccctct agatctatca gccaaaacac ccgtcctag                          39

<210> SEQ ID NO 55
<211> LENGTH: 43
<212> TYPE: DNA
<213> ORGANISM: Corynascus thermophilus

<400> SEQUENCE: 55
acacaactgg ggatccacca tgaagctctc tctcttttcc gtc                     43

<210> SEQ ID NO 56
<211> LENGTH: 38
<212> TYPE: DNA
<213> ORGANISM: Corynascus thermophilus

<400> SEQUENCE: 56
gtcaccctct agatctactc ggaaaggtcg gcctagac                           38

<210> SEQ ID NO 57
<211> LENGTH: 39
<212> TYPE: DNA
<213> ORGANISM: Corynascus thermophilus

<400> SEQUENCE: 57
acacaactgg ggatccacca tgaagtcctt caccctcac                          39

<210> SEQ ID NO 58
<211> LENGTH: 38
<212> TYPE: DNA
<213> ORGANISM: Corynascus thermophilus

<400> SEQUENCE: 58
gtcaccctct agatctagaa agtgccctgg ctagggac                           38

<210> SEQ ID NO 59
<211> LENGTH: 43
<212> TYPE: DNA
<213> ORGANISM: Corynascus thermophilus

<400> SEQUENCE: 59
acacaactgg ggatccacca tgaagtcgtt cacctcagcc ttg                     43

<210> SEQ ID NO 60
<211> LENGTH: 36
<212> TYPE: DNA
<213> ORGANISM: Corynascus thermophilus

<400> SEQUENCE: 60
gtcaccctct agatctgggt ctggttccag cgacaa                             36

<210> SEQ ID NO 61
```

```
<211> LENGTH: 40
<212> TYPE: DNA
<213> ORGANISM: Corynascus thermophilus

<400> SEQUENCE: 61
acacaactgg ggatccacca tgaaggcctt tagcctcgtc                           40

<210> SEQ ID NO 62
<211> LENGTH: 34
<212> TYPE: DNA
<213> ORGANISM: Corynascus thermophilus

<400> SEQUENCE: 62
gtcaccctct agatctcctc tctcggctcg ggag                                 34

<210> SEQ ID NO 63
<211> LENGTH: 41
<212> TYPE: DNA
<213> ORGANISM: Corynascus thermophilus

<400> SEQUENCE: 63
acacaactgg ggatccacca tggccaagac ctctgctctc c                         41

<210> SEQ ID NO 64
<211> LENGTH: 36
<212> TYPE: DNA
<213> ORGANISM: Corynascus thermophilus

<400> SEQUENCE: 64
gtcaccctct agatctcgct caccgacttg gcattc                               36

<210> SEQ ID NO 65
<211> LENGTH: 1599
<212> TYPE: DNA
<213> ORGANISM: Aspergillus fumigatus

<400> SEQUENCE: 65
atgctggcct ccaccttctc ctaccgcatg tacaagaccg cgctcatcct ggccgccctt     60
ctgggctctg gccaggctca gcaggtcggt acttcccagg cggaagtgca tccgtccatg    120
acctggcaga gctgcacggc tggcggcagc tgcaccacca caacggcaa ggtggtcatc    180
gacgcgaact ggcgttgggt gcacaaagtc ggcgactaca ccaactgcta caccggcaac    240
acctgggaca cgactatctg ccctgacgat gcgacctgcg catccaactg cgcccttgag    300
ggtgccaact acgaatccac ctatggtgtg accgccagcg gcaattccct ccgcctcaac    360
ttcgtcacca ccagccagca agaacatt ggctcgcgtc tgtacatgat gaaggacgac    420
tcgacctacg agatgtttaa gctgctgaac caggagttca ccttcgatgt cgatgtctcc    480
aacctcccct gcggtctcaa cggtgctctg tactttgtcg ccatggacgc cgacggtggc    540
atgtccaagt acccaaccaa caaggccggt gccaagtacg gtactggata ctgtgactcg    600
cagtgccctc gcgacctcaa gttcatcaac ggtcaggcca cgtcgaagg gtggcagccc    660
tcctccaacg atgccaatgc gggtaccggc aaccacgggt cctgctgcgc ggagatggat    720
atctgggagg ccaacagcat ctccacggcc ttcacccccc atccgtgcga cacgcccggc    780
caggtgatgt gcaccggtga tgcctgcggt ggcacctaca gctccgaccg ctacggcggc    840
acctgcgacc ccgacggatg tgatttcaac tccttccgcc agggcaacaa gaccttctac    900
ggccctggca tgaccgtcga caccaagagc aagtttaccg tcgtcaccca gttcatcacc    960
gacgacggca cctccagcgg caccctcaag gagatcaagc gcttctacgt gcagaacggc   1020
```

```
aaggtgatcc ccaactcgga gtcgacctgg accggcgtca gcggcaactc catcaccacc    1080
gagtactgca ccgcccagaa gagcctgttc caggaccaga acgtcttcga aaagcacggc    1140
ggcctcgagg gcatgggtgc tgccctcgcc cagggtatgg ttctcgtcat gtccctgtgg    1200
gatgatcact cggccaacat gctctggctc gacagcaact acccgaccac tgcctcttcc    1260
accactcccg gcgtcgcccg tggtacctgc gacatctcct ccggcgtccc tgcggatgtc    1320
gaggcgaacc accccgacgc ctacgtcgtc tactccaaca tcaaggtcgg ccccatcggc    1380
tcgaccttca acagcggtgg ctcgaacccc ggtggcggaa ccaccacgac aactaccacc    1440
cagcctacta ccaccacgac cacggctgga accctggcg gcaccggagt cgcacagcac    1500
tatggccagt gtggtggaat cggatggacc ggacccacaa cctgtgccag cccttatacc    1560
tgccagaagc tgaatgatta ttactctcag tgcctgtag                           1599
```

<210> SEQ ID NO 66
<211> LENGTH: 532
<212> TYPE: PRT
<213> ORGANISM: Aspergillus fumigatus

<400> SEQUENCE: 66

```
Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80

Thr Trp Asp Thr Thr Ile Cys Pro Asp Asp Ala Thr Cys Ala Ser Asn
                85                  90                  95

Cys Ala Leu Glu Gly Ala Asn Tyr Glu Ser Thr Tyr Gly Val Thr Ala
            100                 105                 110

Ser Gly Asn Ser Leu Arg Leu Asn Phe Val Thr Thr Ser Gln Gln Lys
        115                 120                 125

Asn Ile Gly Ser Arg Leu Tyr Met Met Lys Asp Asp Ser Thr Tyr Glu
    130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175

Ala Asp Gly Gly Met Ser Lys Tyr Pro Thr Asn Lys Ala Gly Ala Lys
            180                 185                 190

Tyr Gly Thr Gly Tyr Cys Asp Ser Gln Cys Pro Arg Asp Leu Lys Phe
        195                 200                 205

Ile Asn Gly Gln Ala Asn Val Glu Gly Trp Gln Pro Ser Ser Asn Asp
    210                 215                 220

Ala Asn Ala Gly Thr Gly Asn His Gly Ser Cys Cys Ala Glu Met Asp
225                 230                 235                 240

Ile Trp Glu Ala Asn Ser Ile Ser Thr Ala Phe Thr Pro His Pro Cys
                245                 250                 255

Asp Thr Pro Gly Gln Val Met Cys Thr Gly Asp Ala Cys Gly Gly Thr
            260                 265                 270
```

```
Tyr Ser Ser Asp Arg Tyr Gly Gly Thr Cys Asp Pro Asp Gly Cys Asp
            275                 280                 285

Phe Asn Ser Phe Arg Gln Gly Asn Lys Thr Phe Tyr Gly Pro Gly Met
            290                 295                 300

Thr Val Asp Thr Lys Ser Lys Phe Thr Val Val Thr Gln Phe Ile Thr
305                 310                 315                 320

Asp Asp Gly Thr Ser Ser Gly Thr Leu Lys Glu Ile Lys Arg Phe Tyr
            325                 330                 335

Val Gln Asn Gly Lys Val Ile Pro Asn Ser Glu Ser Thr Trp Thr Gly
            340                 345                 350

Val Ser Gly Asn Ser Ile Thr Thr Glu Tyr Cys Thr Ala Gln Lys Ser
            355                 360                 365

Leu Phe Gln Asp Gln Asn Val Phe Glu Lys His Gly Gly Leu Glu Gly
            370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
            405                 410                 415

Thr Ala Ser Ser Thr Thr Pro Gly Val Ala Arg Gly Thr Cys Asp Ile
            420                 425                 430

Ser Ser Gly Val Pro Ala Asp Val Glu Ala Asn His Pro Asp Ala Tyr
            435                 440                 445

Val Val Tyr Ser Asn Ile Lys Val Gly Pro Ile Gly Ser Thr Phe Asn
            450                 455                 460

Ser Gly Gly Ser Asn Pro Gly Gly Gly Thr Thr Thr Thr Thr Thr Thr
465                 470                 475                 480

Gln Pro Thr Thr Thr Thr Thr Ala Gly Asn Pro Gly Gly Thr Gly
            485                 490                 495

Val Ala Gln His Tyr Gly Gln Cys Gly Gly Ile Gly Trp Thr Gly Pro
            500                 505                 510

Thr Thr Cys Ala Ser Pro Tyr Thr Cys Gln Lys Leu Asn Asp Tyr Tyr
            515                 520                 525

Ser Gln Cys Leu
        530

<210> SEQ ID NO 67
<211> LENGTH: 1713
<212> TYPE: DNA
<213> ORGANISM: Aspergillus fumigatus

<400> SEQUENCE: 67
atgaagcacc ttgcatcttc catcgcattg actctactgt tgcctgccgt gcaggcccag    60
cagaccgtat ggggccaatg tatgttctgg ctgtcactgg aataagactg tatcaactgc   120
tgatatgctt ctaggtggcg gccaaggctg gtctggcccg acgagctgtg ttgccggcgc   180
agcctgtagc acactgaatc cctgtatgtt agatatcgtc ctgagtggag acttatactg   240
acttccttag actacgctca gtgtatcccg ggagccaccg cgacgtccac caccctcacg   300
acgacgacgg cggcgacgac gacatcccag accaccacca aacctaccac gactggtcca   360
actacatccg cacccaccgt gaccgcatcc ggtaacccct tcagcggcta ccagctgtat   420
gccaaccccc tactactcct cgaggtccat actctggcca tgccttctct gcccagctcg   480
ctgcagccca aggctagtgc tgttgctgaa gtgccctcat tgtttggct gtaagtggcc   540 ttatcccaat actgagacca actctctgac agtcgtagcg acgttgccgc caaggtgccc   600
```

```
actatgggaa cctacctggc cgacattcag gccaagaaca aggccggcgc caaccctcct    660
atcgctggta tcttcgtggt ctacgacttg ccggaccgtg actgcgccgc tctggccagt    720
aatggcgagt actcaattgc caacaacggt gtggccaact acaaggcgta cattgacgcc    780
atccgtgctc agctggtgaa gtactctgac gttcacacca tcctcgtcat cggtaggccg    840
tacacctccg ttgcgcgccg cctttctctg acatcttgca gaacccgaca gcttggccaa    900
cctggtgacc aacctcaacg tcgccaaatg cgccaatgcg cagagcgcct acctggagtg    960
tgtcgactat gctctgaagc agctcaacct gcccaacgtc gccatgtacc tcgacgcagg   1020
tatgcctcac ttcccgcatt ctgtatccct tccagacact aactcatcag gccatgcggg   1080
ctggctcgga tggcccgcca acttgggccc cgccgcaaca ctcttcgcca agtctacac    1140
cgacgcgggt tcccccgcgg ctgttcgtgg cctggccacc aacgtcgcca actacaacgc   1200
ctggtcgctc agtacctgcc cctcctacac ccagggagac cccaactgcg acgagaagaa   1260
gtacatcaac gccatggcgc tcttctcaa ggaagccggc ttcgatgccc acttcatcat    1320
ggatacctgt aagtgcttat tccaatcgcc gatgtgtgcc gactaatcaa tgtttcagcc   1380
cggaatggcg tccagcccac gaagcaaaac gcctggggtg actggtgcaa cgtcatcggc   1440
accggcttcg gtgttcgccc ctcgactaac accggcgatc cgctccagga tgcctttgtg   1500
tggatcaagc ccggtggaga gagtgatggc acgtccaact cgacttcccc ccggtatgac   1560
gcgcactgcg gatatagtga tgctctgcag cctgctcctg aggctggtac ttggttccag   1620
gtatgtcatc cattagccag atgagggata agtgactgac ggacctaggc ctactttgag   1680
cagcttctga ccaacgctaa cccgtccttt taa                                1713
```

<210> SEQ ID NO 68
<211> LENGTH: 454
<212> TYPE: PRT
<213> ORGANISM: Aspergillus fumigatus

<400> SEQUENCE: 68

```
Met Lys His Leu Ala Ser Ser Ile Ala Leu Thr Leu Leu Pro Ala
1               5                  10                  15

Val Gln Ala Gln Gln Thr Val Trp Gly Gln Cys Gly Gly Gln Gly Trp
            20                  25                  30

Ser Gly Pro Thr Ser Cys Val Ala Gly Ala Ala Cys Ser Thr Leu Asn
        35                  40                  45

Pro Tyr Tyr Ala Gln Cys Ile Pro Gly Ala Thr Ala Thr Ser Thr Thr
    50                  55                  60

Leu Thr Thr Thr Thr Ala Ala Thr Thr Thr Ser Gln Thr Thr Thr Lys
65                  70                  75                  80

Pro Thr Thr Thr Gly Pro Thr Thr Ser Ala Pro Thr Val Thr Ala Ser
                85                  90                  95

Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
        115                 120                 125

Pro Lys Ala Ser Ala Val Ala Glu Val Pro Ser Phe Val Trp Leu Asp
    130                 135                 140

Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
                165                 170                 175
```

Val Tyr Asp Leu Pro Asp Arg Asp Cys Ala Ala Leu Ala Ser Asn Gly
            180                 185                 190

Glu Tyr Ser Ile Ala Asn Asn Gly Val Ala Asn Tyr Lys Ala Tyr Ile
        195                 200                 205

Asp Ala Ile Arg Ala Gln Leu Val Lys Tyr Ser Asp Val His Thr Ile
    210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
                245                 250                 255

Tyr Ala Leu Lys Gln Leu Asn Leu Pro Asn Val Ala Met Tyr Leu Asp
            260                 265                 270

Ala Gly His Ala Gly Trp Leu Gly Trp Pro Ala Asn Leu Gly Pro Ala
        275                 280                 285

Ala Thr Leu Phe Ala Lys Val Tyr Thr Asp Ala Gly Ser Pro Ala Ala
    290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys
                325                 330                 335

Lys Tyr Ile Asn Ala Met Ala Pro Leu Leu Lys Glu Ala Gly Phe Asp
            340                 345                 350

Ala His Phe Ile Met Asp Thr Ser Arg Asn Gly Val Gln Pro Thr Lys
        355                 360                 365

Gln Asn Ala Trp Gly Asp Trp Cys Asn Val Ile Gly Thr Gly Phe Gly
    370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
                405                 410                 415

Pro Arg Tyr Asp Ala His Cys Gly Tyr Ser Asp Ala Leu Gln Pro Ala
            420                 425                 430

Pro Glu Ala Gly Thr Trp Phe Gln Ala Tyr Phe Glu Gln Leu Leu Thr
        435                 440                 445

Asn Ala Asn Pro Ser Phe
    450

<210> SEQ ID NO 69
<211> LENGTH: 1849
<212> TYPE: DNA
<213> ORGANISM: Trichoderma reesei

<400> SEQUENCE: 69
tgccatttct gacctggata ggttttccta tggtcattcc tataagagac acgctctttc      60
gtcggcccgt agatatcaga ttggtattca gtcgcacaga cgaaggtgag ttgatcctcc     120
aacatgagtt ctatgagccc cccccttgcc cccccccgtt caccttgacc tgcaatgaga     180
atcccacctt ttacaagagc atcaagaagt attaatggcg ctgaatagcc tctgctcgat     240
aatatctccc cgtcatcgac aatgaacaag tccgtggctc cattgctgct tgcagcgtcc     300
atactatatg gcggcgccgt cgcacagcag actgtctggg ccagtgtgg aggtattggt       360 tggagcggac ctacgaattg tgctcctggc tcagcttgtt cgaccctcaa tccttattat     420
gcgcaatgta ttccgggagc cactactatc accacttcga cccggccacc atccggtcca     480

-continued

| | |
|---|---|
| accaccacca ccagggctac ctcaacaagc tcatcaactc cacccacgag ctctggggtc | 540 |
| cgatttgccg gcgttaacat cgcgggtttt gactttggct gtaccacaga gtgagtaccc | 600 |
| ttgtttcctg gtgttgctgg ctggttgggc gggtatacag cgaagcggac gcaagaacac | 660 |
| cgccggtccg ccaccatcaa gatgtgggtg taagcggcg gtgttttgta caactacctg | 720 |
| acagctcact caggaaatga gaattaatgg aagtcttgtt acagtggcac ttgcgttacc | 780 |
| tcgaaggttt atcctccgtt gaagaacttc accggctcaa caactaccc cgatggcatc | 840 |
| ggccagatgc agcacttcgt caacgaggac gggatgacta ttttccgctt acctgtcgga | 900 |
| tggcagtacc tcgtcaacaa caatttgggc ggcaatcttg attccacgag catttccaag | 960 |
| tatgatcagc ttgttcaggg gtgcctgtct ctgggcgcat actgcatcgt cgacatccac | 1020 |
| aattatgctc gatggaacgg tgggatcatt ggtcagggcg gccctactaa tgctcaattc | 1080 |
| acgagccttt ggtcgcagtt ggcatcaaag tacgcatctc agtcgagggt gtggttcggc | 1140 |
| atcatgaatg agccccacga cgtgaacatc aacacctggg ctgccacggt ccaagaggtt | 1200 |
| gtaaccgcaa tccgcaacgc tggtgctacg tcgcaattca tctctctttgcc tggaaatgat | 1260 |
| tggcaatctg ctgggctttt catatccgat ggcagtgcag ccgccctgtc tcaagtcacg | 1320 |
| aacccggatg ggtcaacaac gaatctgatt tttgacgtgc acaaatactt ggactcagac | 1380 |
| aactccggta ctcacgccga atgtactaca ataacattg acggcgcctt ttctccgctt | 1440 |
| gccacttggc tccgacagaa caatcgccag gctatcctga cagaaaccgg tggtggcaac | 1500 |
| gttcagtcct gcatacaaga catgtgccag caaatccaat atctcaacca gaactcagat | 1560 |
| gtctatcttg gctatgttgg ttggggtgcc ggatcatttg atagcacgta tgtcctgacg | 1620 |
| gaaacaccga ctggcagtgg taactcatgg acggacacat ccttggtcag ctcgtgtctc | 1680 |
| gcaagaaagt agcactctga gctgaatgca gaagcctcgc caacgtttgt atctcgctat | 1740 |
| caaacatagt agctactcta tgaggctgtc tgttctcgat ttcagcttta tatagtttca | 1800 |
| tcaaacagta catattccct ctgtggccac gcaaaaaaaa aaaaaaaaa | 1849 |

<210> SEQ ID NO 70
<211> LENGTH: 418
<212> TYPE: PRT
<213> ORGANISM: Trichoderma reesei

<400> SEQUENCE: 70

```
Met Asn Lys Ser Val Ala Pro Leu Leu Ala Ala Ser Ile Leu Tyr
1               5                   10                  15

Gly Gly Ala Val Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Glu
```

```
                130             135             140
Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
                325                 330                 335

Thr Trp Leu Arg Gln Asn Asn Arg Gln Ala Ile Leu Thr Glu Thr Gly
            340                 345                 350

Gly Gly Asn Val Gln Ser Cys Ile Gln Asp Met Cys Gln Gln Ile Gln
        355                 360                 365

Tyr Leu Asn Gln Asn Ser Asp Val Tyr Leu Gly Tyr Val Gly Trp Gly
    370                 375                 380

Ala Gly Ser Phe Asp Ser Thr Tyr Val Leu Thr Glu Thr Pro Thr Gly
385                 390                 395                 400

Ser Gly Asn Ser Trp Thr Asp Thr Ser Leu Val Ser Ser Cys Leu Ala
                405                 410                 415

Arg Lys

<210> SEQ ID NO 71
<211> LENGTH: 1415
<212> TYPE: DNA
<213> ORGANISM: Aspergillus fumigatus

<400> SEQUENCE: 71
atggtccatc tatcttcatt ggcagcagcc ctggctgctc tgcctctgta tgtttaccca      60
ctcacgagag aggaacagc tttgacattg ctatagtgta tatggagctg cctgaacac      120 agcagccaaa gccaaaggac taaagtactt tggttccgcc acggacaatc agagctcac      180 ggactctgcg tatgtcgcgc aactgagcaa caccgatgat tttggtcaaa tcacacccgg      240
aaactccatg aaggtttgct tacgtctgcc tccctggagc attgcctcaa agctaattg      300 gttgttttgt ttggatagtg ggatgccacc gagccttctc agaattcttt ttcgttcgca      360
aatggagacg ccgtggtcaa tctggcgaac aagaatggcc agctgatgcg atgccatact      420
ctggtctggc acagtcagct accgaactgg ggtatgtaaa cgtcttgtct attctcaaat      480
```

```
actctctaac agttgacagt ctctagcggg tcatggacca atgcgaccct tttggcggcc    540
atgaagaatc atatccacaa tgtggttact cactacaagg ggaagtgcta cgcctgggat    600
gttgtcaatg aaggtttgtt gctccatcta tcctcaatag ttcttttgaa actgacaagc    660
ctgtcaatct agccctgaac gaggacggta ctttccgtaa ctctgtcttc taccagatca    720
tcggcccagc atacattcct attgcgttcg ccacggctgc tgccgcagat cccgacgtga    780
aactctacta caacgactac aacattgaat actcaggcgc caaagcgact gctgcgcaga    840
atatcgtcaa gatgatcaag gcctacggcg cgaagatcga cggcgtcggc ctccaggcac    900
actttatcgt cggcagcact ccgagtcaat cggatctgac gaccgtcttg aagggctaca    960
ctgctctcgg cgttgaggtg gcctataccg aacttgacat ccgcatgcag ctgccctcga   1020
ccgccgcaaa gctggcccag cagtccactg acttccaagg cgtggccgca gcatgcgtta   1080
gcaccactgg ctgcgtgggt gtcactatct gggactggac cgacaagtac tcctgggtcc   1140
ccagcgtgtt ccaaggctac ggcgccccat tgccttggga tgagaactat gtgaagaagc   1200
cagcgtacga tggcctgatg gcgggtcttg gagcaagcgg ctccggcacc acaacgacca   1260
ctactactac ttctactacg acaggaggta cggaccctac tggagtcgct cagaaatggg   1320
gacagtgtgg cggtattggc tggaccgggc caacaacttg tgtcagtggt accacttgcc   1380
aaaagctgaa tgactggtac tcacagtgcc tgtaa                              1415
```

<210> SEQ ID NO 72
<211> LENGTH: 397
<212> TYPE: PRT
<213> ORGANISM: Aspergillus fumigatus

<400> SEQUENCE: 72

```
Met Val His Leu Ser Ser Leu Ala Ala Leu Ala Ala Leu Pro Leu
1               5                   10                  15

Val Tyr Gly Ala Gly Leu Asn Thr Ala Ala Lys Ala Lys Gly Leu Lys
            20                  25                  30

Tyr Phe Gly Ser Ala Thr Asp Asn Pro Glu Leu Thr Asp Ser Ala Tyr
        35                  40                  45

Val Ala Gln Leu Ser Asn Thr Asp Asp Phe Gly Gln Ile Thr Pro Gly
    50                  55                  60

Asn Ser Met Lys Trp Asp Ala Thr Glu Pro Ser Gln Asn Ser Phe Ser
65                  70                  75                  80

Phe Ala Asn Gly Asp Ala Val Val Asn Leu Ala Asn Lys Asn Gly Gln
                85                  90                  95

Leu Met Arg Cys His Thr Leu Val Trp His Ser Gln Leu Pro Asn Trp
            100                 105                 110

Val Ser Ser Gly Ser Trp Thr Asn Ala Thr Leu Leu Ala Ala Met Lys
        115                 120                 125

Asn His Ile Thr Asn Val Val Thr His Tyr Lys Gly Lys Cys Tyr Ala
    130                 135                 140

Trp Asp Val Val Asn Glu Ala Leu Asn Glu Asp Gly Thr Phe Arg Asn
145                 150                 155                 160

Ser Val Phe Tyr Gln Ile Ile Gly Pro Ala Tyr Ile Pro Ile Ala Phe
                165                 170                 175

Ala Thr Ala Ala Ala Ala Asp Pro Asp Val Lys Leu Tyr Tyr Asn Asp
            180                 185                 190

Tyr Asn Ile Glu Tyr Ser Gly Ala Lys Ala Thr Ala Ala Gln Asn Ile
        195                 200                 205
```

```
Val Lys Met Ile Lys Ala Tyr Gly Ala Lys Ile Asp Gly Val Gly Leu
    210                 215                 220
Gln Ala His Phe Ile Val Gly Ser Thr Pro Ser Gln Ser Asp Leu Thr
225                 230                 235                 240
Thr Val Leu Lys Gly Tyr Thr Ala Leu Gly Val Glu Val Ala Tyr Thr
                245                 250                 255
Glu Leu Asp Ile Arg Met Gln Leu Pro Ser Thr Ala Ala Lys Leu Ala
                260                 265                 270
Gln Gln Ser Thr Asp Phe Gln Gly Val Ala Ala Ala Cys Val Ser Thr
            275                 280                 285
Thr Gly Cys Val Gly Val Thr Ile Trp Asp Trp Thr Asp Lys Tyr Ser
    290                 295                 300
Trp Val Pro Ser Val Phe Gln Gly Tyr Gly Ala Pro Leu Pro Trp Asp
305                 310                 315                 320
Glu Asn Tyr Val Lys Lys Pro Ala Tyr Asp Gly Leu Met Ala Gly Leu
                325                 330                 335
Gly Ala Ser Gly Ser Gly Thr Thr Thr Thr Thr Thr Thr Thr Ser Thr
            340                 345                 350
Thr Thr Gly Gly Thr Asp Pro Thr Gly Val Ala Gln Lys Trp Gly Gln
    355                 360                 365
Cys Gly Gly Ile Gly Trp Thr Gly Pro Thr Thr Cys Val Ser Gly Thr
    370                 375                 380
Thr Cys Gln Lys Leu Asn Asp Trp Tyr Ser Gln Cys Leu
385                 390                 395

<210> SEQ ID NO 73
<211> LENGTH: 3060
<212> TYPE: DNA
<213> ORGANISM: Aspergillus fumigatus

<400> SEQUENCE: 73
atgagattcg gttggctcga ggtggccgct ctgacggccg cttctgtagc caatgcccag      60
gtttgtgatg cttttccgtc attgtttcgg atatagttga caatagtcat ggaaataatc     120
aggaattggc tttctctcca ccattctacc cttcgccttg gctgatggca gggagagt      180 gggcagatgc ccatcgacgc gccgtcgaga tcgtttctca gatgacactg gcggagaagg     240
ttaaccttac aacgggtact gggtgggttg cgactttttt gttgacagtg agctttcttc     300
actgaccatc tacacagatg ggaaatggac cgatgcgtcg gtcaaaccgg cagcgttccc     360
aggtaagctt gcaattctgc aacaacgtgc aagtgtagtt gctaaaacgc ggtggtgcag     420
acttggtatc aactggggtc tttgtggcca ggattcccct ttgggtatcc gtttctgtga     480
gctatacccg cggagtcttt cagtccttgt attatgtgct gatgattgtc tctgtatagc     540
tgacctcaac tccgccttcc ctgctggtac taatgtcgcc gcgacatggg acaagacact     600
cgcctacctt cgtggcaagg ccatgggtga ggaattcaac gacaagggcg tggacatttt     660 gctgggcct gctgctggtc ctctcggcaa atacccggac ggcggcagaa tctgggaagg     720
cttctctcct gatccggttc tcactggtgt acttttcgcc gaaactatca gggtatcca     780 agacgcgggt gtgattgcta ctgccaagca ttacattctg aatgaacagg agcatttccg     840
acaggttggc gaggcccagg gatatggtta caacatcacg gagacgatca gctccaacgt     900
ggatgacaag accatgcacg agttgtacct tggtgagta gttgacactg caaatgagga     960
ccttgattga tttgactgac ctggaatgca ggcccttgc agatgctgtg gcggtaaga    1020 tttttccgtag acttgacctc gcgacgaaga aatcgctgac gaaccatcgt agctggcgtt    1080
```

```
ggcgctgtca tgtgttccta caatcaaatc aacaacagct acggttgtca aaacagtcaa    1140
actctcaaca agctcctcaa ggctgagctg ggcttccaag gcttcgtcat gagtgactgg    1200
agcgctcacc acagcggtgt cggcgctgcc ctcgctgggt tggatatgtc gatgcctgga    1260
gacatttcct tcgacgacgg actctccttc tggggcacga acctaactgt cagtgttctt    1320
aacggcaccg ttccagcctg gcgtgtcgat gacatggctg ttcgtatcat gaccgcgtac    1380
tacaaggttg gtcgtgaccg tcttcgtatt cccctaact tcagctcctg acccgggat     1440 gagtacggct gggagcattc tgctgtctcc gagggagcct ggaccaaggt gaacgacttc    1500
gtcaatgtgc agcgcagtca ctctcagatc atccgtgaga ttggtgccgc tagtacagtg    1560
ctcttgaaga acacgggtgc tcttcctttg accggcaagg aggttaaagt gggtgttctc    1620
ggtgaagacg ctggttccaa cccgtggggt gctaacggct gccccgaccg cggctgtgat    1680
aacggcactc ttgctatggc ctggggtagt ggtactgcca acttcccttta ccttgtcacc    1740 cccgagcagc tatccagcg agaggtcatc agcaacggcg gcaatgtctt tgctgtgact    1800
gataacgggg ctctcagcca gatggcagat gttgcatctc aatccaggtg agtgcgggct    1860
cttagaaaaa gaacgttctc tgaatgaagt tttttaacca ttgcgaacag cgtgtctttg    1920
gtgtttgtca acgccgactc tggagagggt ttcatcagtg tcgacggcaa cgagggtgac    1980
cgcaaaaatc tcactctgtg gaagaacggc gaggccgtca ttgacactgt tgtcagccac    2040
tgcaacaaca cgattgtggt tattcacagt gttgggcccg tcttgatcga ccggtggtat    2100
gataacccca acgtcactgc catcatctgg gccggcttgc ccggtcagga gagtggcaac    2160
tccctggtcg acgtgctcta tggccgcgtc aaccccagcg ccaagacccc gttcacctgg    2220
ggcaagactc gggagtctta cggggctccc ttgctcaccg agcctaacaa tggcaatggt    2280
gctccccagg atgatttcaa cgagggcgtc ttcattgact accgtcactt tgacaagcgc    2340
aatgagaccc ccatttatga gtttggccat ggcttgagct acaccacctt tggttactct    2400
caccttcggg ttcaggccct caatagttcg agttcggcat atgtcccgac tagcggagag    2460
accaagcctg cgccaaccta tggtgagatc ggtagtgccg ccgactacct gtatcccgag    2520
ggtctcaaaa gaattaccaa gtttatttac ccttggctca actcgaccga cctcgaggat    2580
tcttctgacg acccgaacta cggctgggag gactcggagt acattcccga aggcgctagg    2640
gatgggtctc ctcaaccccc tctgaaggct ggcggcgctc ctggtggtaa ccctacccct    2700
tatcaggatc ttgttagggt gtcggccacc ataaccaaca ctggtaacgt cgccggttat    2760
gaagtccctc aattggtgag tgaccccgcat gttccttgcg ttgcaatttg gctaactcgc    2820
ttctagtatg tttcactggg cggaccgaac gagcctcggg tcgttctgcg caagttcgac    2880
cgaatcttcc tggctcctgg ggagcaaaag gtttggacca cgactcttaa ccgtcgtgat    2940
ctcgccaatt gggatgtgga ggctcaggac tgggtcatca aaagtacccc caagaaagtg    3000
cacgtcggca gctcctcgcg taagctgcct ctgagagcgc tctgccccg tgtctactag    3060
```

<210> SEQ ID NO 74
<211> LENGTH: 863
<212> TYPE: PRT
<213> ORGANISM: Aspergillus fumigatus

<400> SEQUENCE: 74

Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro

-continued

```
                 20                  25                  30
Trp Ala Asp Gly Gln Gly Glu Trp Ala Asp Ala His Arg Arg Ala Val
             35                  40                  45
Glu Ile Val Ser Gln Met Thr Leu Ala Glu Lys Val Asn Leu Thr Thr
         50                  55                  60
Gly Thr Gly Trp Glu Met Asp Arg Cys Val Gly Gln Thr Gly Ser Val
 65                  70                  75                  80
Pro Arg Leu Gly Ile Asn Trp Gly Leu Cys Gly Gln Asp Ser Pro Leu
                 85                  90                  95
Gly Ile Arg Phe Ser Asp Leu Asn Ser Ala Phe Pro Ala Gly Thr Asn
            100                 105                 110
Val Ala Ala Thr Trp Asp Lys Thr Leu Ala Tyr Leu Arg Gly Lys Ala
            115                 120                 125
Met Gly Glu Glu Phe Asn Asp Lys Gly Val Asp Ile Leu Leu Gly Pro
            130                 135                 140
Ala Ala Gly Pro Leu Gly Lys Tyr Pro Asp Gly Gly Arg Ile Trp Glu
145                 150                 155                 160
Gly Phe Ser Pro Asp Pro Val Leu Thr Gly Val Leu Phe Ala Glu Thr
                165                 170                 175
Ile Lys Gly Ile Gln Asp Ala Gly Val Ile Ala Thr Ala Lys His Tyr
            180                 185                 190
Ile Leu Asn Glu Gln Glu His Phe Arg Gln Val Gly Glu Ala Gln Gly
            195                 200                 205
Tyr Gly Tyr Asn Ile Thr Glu Thr Ile Ser Ser Asn Val Asp Asp Lys
        210                 215                 220
Thr Met His Glu Leu Tyr Leu Trp Pro Phe Ala Asp Ala Val Arg Ala
225                 230                 235                 240
Gly Val Gly Ala Val Met Cys Ser Tyr Asn Gln Ile Asn Asn Ser Tyr
                245                 250                 255
Gly Cys Gln Asn Ser Gln Thr Leu Asn Lys Leu Leu Lys Ala Glu Leu
            260                 265                 270
Gly Phe Gln Gly Phe Val Met Ser Asp Trp Ser Ala His His Ser Gly
            275                 280                 285
Val Gly Ala Ala Leu Ala Gly Leu Asp Met Ser Met Pro Gly Asp Ile
        290                 295                 300
Ser Phe Asp Asp Gly Leu Ser Phe Trp Gly Thr Asn Leu Thr Val Ser
305                 310                 315                 320
Val Leu Asn Gly Thr Val Pro Ala Trp Arg Val Asp Asp Met Ala Val
                325                 330                 335
Arg Ile Met Thr Ala Tyr Tyr Lys Val Gly Arg Asp Arg Leu Arg Ile
            340                 345                 350
Pro Pro Asn Phe Ser Ser Trp Thr Arg Asp Glu Tyr Gly Trp Glu His
            355                 360                 365
Ser Ala Val Ser Glu Gly Ala Trp Thr Lys Val Asn Asp Phe Val Asn
        370                 375                 380
Val Gln Arg Ser His Ser Gln Ile Ile Arg Glu Ile Gly Ala Ala Ser
385                 390                 395                 400
Thr Val Leu Leu Lys Asn Thr Gly Ala Leu Pro Leu Thr Gly Lys Glu
                405                 410                 415
Val Lys Val Gly Val Leu Gly Glu Asp Ala Gly Ser Asn Pro Trp Gly
            420                 425                 430
Ala Asn Gly Cys Pro Asp Arg Gly Cys Asp Asn Gly Thr Leu Ala Met
            435                 440                 445
```

```
Ala Trp Gly Ser Gly Thr Ala Asn Phe Pro Tyr Leu Val Thr Pro Glu
            450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Phe
                500                 505                 510

Ile Ser Val Asp Gly Asn Glu Gly Asp Arg Lys Asn Leu Thr Leu Trp
            515                 520                 525

Lys Asn Gly Glu Ala Val Ile Asp Thr Val Ser His Cys Asn Asn
530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
                580                 585                 590

Pro Ser Ala Lys Thr Pro Phe Thr Trp Gly Lys Thr Arg Glu Ser Tyr
            595                 600                 605

Gly Ala Pro Leu Leu Thr Glu Pro Asn Asn Gly Asn Gly Ala Pro Gln
            610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
                660                 665                 670

Ser Ala Tyr Val Pro Thr Ser Gly Glu Thr Lys Pro Ala Pro Thr Tyr
            675                 680                 685

Gly Glu Ile Gly Ser Ala Ala Asp Tyr Leu Tyr Pro Glu Gly Leu Lys
            690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
                740                 745                 750

Gly Ala Pro Gly Gly Asn Pro Thr Leu Tyr Gln Asp Leu Val Arg Val
            755                 760                 765

Ser Ala Thr Ile Thr Asn Thr Gly Asn Val Ala Gly Tyr Glu Val Pro
770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
                820                 825                 830

Gln Asp Trp Val Ile Thr Lys Tyr Pro Lys Lys Val His Val Gly Ser
            835                 840                 845

Ser Ser Arg Lys Leu Pro Leu Arg Ala Pro Leu Pro Arg Val Tyr
850                 855                 860
```

<210> SEQ ID NO 75
<211> LENGTH: 2388
<212> TYPE: DNA
<213> ORGANISM: Talaromyces emersonii

<400> SEQUENCE: 75

| | | | | | |
|---|---|---|---|---|---|
| atgatgactc | ccacggcgat | tctcaccgca | gtggcggcgc | tcctgcccac | cgcgacatgg | 60 |
| gcacaggata | accaaaccta | tgccaattac | tcgtcgcagt | ctcagccgga | cctgtttccc | 120 |
| cggaccgtcg | cgaccatcga | cctgtccttc | cccgactgtg | agaatgggcc | gctcagcacg | 180 |
| aacctggtgt | gcaacaaatc | ggccgatccc | tgggcccgag | ctgaggccct | catctcgctc | 240 |
| tttaccctcg | aagagctgat | taacaacacc | cagaacaccg | ctcctggcgt | gccccgtttg | 300 |
| ggtctgcccc | agtatcaggt | gtggaatgaa | gctctgcacg | gactggaccg | cgccaatttc | 360 |
| tcccattcgg | gcgaatacag | ctgggccacg | tccttcccca | tgccatcct | gtcgatggcg | 420 |
| tccttcaacc | ggaccctcat | caaccagatt | gcctccatca | ttgcaacgca | agcccgtgcc | 480 |
| ttcaacaacg | ccggccgtta | cggccttgac | agctatgcgc | caacatcaa | tggcttccgc | 540 |
| agtcccctct | ggggccgtgg | acaggagacg | cctggtgagg | atgcgttctt | cttgagttcc | 600 |
| acctatgcgt | acgagtacat | cacaggcctg | cagggcggtg | tcgacccaga | gcatgtcaag | 660 |
| atcgtcgcga | cggcgaagca | cttcgccggc | tatgatctgg | agaactgggg | caacgtctct | 720 |
| cggctggggt | tcaatgctat | catcacgcag | caggatctct | ccgagtacta | caccctcag | 780 |
| ttcctggcgt | ctgctcgata | cgccaagacg | cgcagcatca | tgtgctccta | caatgcagtg | 840 |
| aatgagtcc | caagctgtgc | caactccttc | ttcctccaga | cgcttctccg | agaaaacttt | 900 |
| gacttcgttg | acgacgggta | cgtctcgtcg | gattgcgacg | ccgtctacaa | cgtcttcaac | 960 |
| ccacacggtt | acgcccttaa | ccagtcggga | gccgctgcgg | actcgctcct | agcaggtacc | 1020 |
| gatatcgact | gtggtcagac | cttgccgtgg | cacctgaatg | agtccttcgt | agaaggatac | 1080 |
| gtctcccgcg | gtgatatcga | gaaatccctc | accgtctctct | actcaaacct | ggtgcgtctc | 1140 |
| ggctactttg | acggcaacaa | cagcgagtac | cgcaacctca | ctggaacga | cgtcgtgact | 1200 |
| acggacgcct | ggaacatctc | gtacgaggcc | gcggtggaag | gtatcaccct | gctcaagaac | 1260 |
| gacggaacgc | tgccgctgtc | caagaaggtc | cgcagcattg | cgctcatcgg | tccttgggcc | 1320 |
| aatgccacgg | tgcagatgca | gggtaactac | tatggaacgc | caccgtatct | gatcagtccg | 1380 |
| ctggaagccg | ccaaggccag | tgggttcacg | gtcaactatg | cattcggtac | caacatctcg | 1440 |
| accgattcta | cccagtggtt | cgcggaagcc | atcgcggcgg | cgaagaagtc | ggacgtgatc | 1500 |
| atctacgccg | gtggtattga | caacacgatc | gaggcagagg | acaggaccg | cacggatctc | 1560 |
| aagtggccgg | ggaaccagct | ggatctgatc | gagcagctca | gccaggtggg | caagcccttg | 1620 |
| gtcgtcctgc | agatgggcgg | tggccaggtg | gattcgtcgt | cactcaaggc | caacaagaat | 1680 |
| gtcaacgctc | tggtgtgggg | tggctatccc | ggacagtcgg | gtggtgcggc | cctgtttgac | 1740 |
| atccttacgg | gcaagcgtgc | gccggccggt | cgtctggtga | gcacgcagta | cccggccgag | 1800 |
| tatgcgacgc | agttcccggc | caacgacatg | aacctgcgtc | gaacggcag | caacccggga | 1860 |
| cagacataca | tctggtacac | gggcacgccc | gtgtatgagt | tcggccacgg | tctgttctac | 1920 |
| acggagttcc | aggagtcggc | tgcggcgggc | acgaacaaga | cgtcgacttt | cgacattctg | 1980 |
| gaccttttct | ccaccctca | tccgggatac | gagtacatcg | agcaggttcc | gttcatcaac | 2040 |
| gtgactgtgg | acgtgaagaa | cgtcggccac | acgccatcgc | cgtacacggg | tctgttgttc | 2100 |
| gcgaacacga | cagccgggcc | caagccgtac | ccgaacaaat | ggctcgtcgg | gttcgactgg | 2160 |

```
ctgccgacga tccagccggg cgagactgcc aagttgacga tcccggtgcc gttgggcgcg    2220
attgcgtggg cggacgagaa cggcaacaag gtggtcttcc cgggcaacta cgaattggca    2280
ctgaacaatg agcgatcggt agtggtgtcg ttcacgctga cgggcgatgc ggcgactcta    2340
gagaaatggc ctttgtggga gcaggcggtt ccggggtgc tgcagcaa                 2388
```

<210> SEQ ID NO 76
<211> LENGTH: 796
<212> TYPE: PRT
<213> ORGANISM: Talaromyces emersonii

<400> SEQUENCE: 76

```
Met Met Thr Pro Thr Ala Ile Leu Thr Ala Val Ala Ala Leu Leu Pro
1               5                   10                  15

Thr Ala Thr Trp Ala Gln Asp Asn Gln Thr Tyr Ala Asn Tyr Ser Ser
            20                  25                  30

Gln Ser Gln Pro Asp Leu Phe Pro Arg Thr Val Ala Thr Ile Asp Leu
        35                  40                  45

Ser Phe Pro Asp Cys Glu Asn Gly Pro Leu Ser Thr Asn Leu Val Cys
    50                  55                  60

Asn Lys Ser Ala Asp Pro Trp Ala Arg Ala Glu Ala Leu Ile Ser Leu
65                  70                  75                  80

Phe Thr Leu Glu Glu Leu Ile Asn Asn Thr Gln Asn Thr Ala Pro Gly
                85                  90                  95

Val Pro Arg Leu Gly Leu Pro Gln Tyr Gln Val Trp Asn Glu Ala Leu
            100                 105                 110

His Gly Leu Asp Arg Ala Asn Phe Ser His Ser Gly Glu Tyr Ser Trp
        115                 120                 125

Ala Thr Ser Phe Pro Met Pro Ile Leu Ser Met Ala Ser Phe Asn Arg
    130                 135                 140

Thr Leu Ile Asn Gln Ile Ala Ser Ile Ile Ala Thr Gln Ala Arg Ala
145                 150                 155                 160

Phe Asn Asn Ala Gly Arg Tyr Gly Leu Asp Ser Tyr Ala Pro Asn Ile
                165                 170                 175

Asn Gly Phe Arg Ser Pro Leu Trp Gly Arg Gly Gln Glu Thr Pro Gly
            180                 185                 190

Glu Asp Ala Phe Phe Leu Ser Ser Thr Tyr Ala Tyr Glu Tyr Ile Thr
        195                 200                 205

Gly Leu Gln Gly Gly Val Asp Pro Glu His Val Lys Ile Val Ala Thr
    210                 215                 220

Ala Lys His Phe Ala Gly Tyr Asp Leu Glu Asn Trp Gly Asn Val Ser
225                 230                 235                 240

Arg Leu Gly Phe Asn Ala Ile Ile Thr Gln Gln Asp Leu Ser Glu Tyr
                245                 250                 255

Tyr Thr Pro Gln Phe Leu Ala Ser Ala Arg Tyr Ala Lys Thr Arg Ser
            260                 265                 270

Ile Met Cys Ser Tyr Asn Ala Val Asn Gly Val Pro Ser Cys Ala Asn
        275                 280                 285

Ser Phe Phe Leu Gln Thr Leu Leu Arg Glu Asn Phe Asp Phe Val Asp
    290                 295                 300

Asp Gly Tyr Val Ser Ser Asp Cys Asp Ala Val Tyr Asn Val Phe Asn
305                 310                 315                 320

Pro His Gly Tyr Ala Leu Asn Gln Ser Gly Ala Ala Ala Asp Ser Leu
                325                 330                 335
```

```
Leu Ala Gly Thr Asp Ile Asp Cys Gly Gln Thr Leu Pro Trp His Leu
            340                 345                 350

Asn Glu Ser Phe Val Glu Gly Tyr Val Ser Arg Gly Asp Ile Glu Lys
            355                 360                 365

Ser Leu Thr Arg Leu Tyr Ser Asn Leu Val Arg Leu Gly Tyr Phe Asp
        370                 375                 380

Gly Asn Asn Ser Glu Tyr Arg Asn Leu Asn Trp Asn Asp Val Val Thr
385                 390                 395                 400

Thr Asp Ala Trp Asn Ile Ser Tyr Glu Ala Val Glu Gly Ile Thr
                405                 410                 415

Leu Leu Lys Asn Asp Gly Thr Leu Pro Leu Ser Lys Lys Val Arg Ser
            420                 425                 430

Ile Ala Leu Ile Gly Pro Trp Ala Asn Ala Thr Val Gln Met Gln Gly
            435                 440                 445

Asn Tyr Tyr Gly Thr Pro Pro Tyr Leu Ile Ser Pro Leu Glu Ala Ala
            450                 455                 460

Lys Ala Ser Gly Phe Thr Val Asn Tyr Ala Phe Gly Thr Asn Ile Ser
465                 470                 475                 480

Thr Asp Ser Thr Gln Trp Phe Ala Glu Ala Ile Ala Ala Lys Lys
                485                 490                 495

Ser Asp Val Ile Ile Tyr Ala Gly Gly Ile Asp Asn Thr Ile Glu Ala
            500                 505                 510

Glu Gly Gln Asp Arg Thr Asp Leu Lys Trp Pro Gly Asn Gln Leu Asp
            515                 520                 525

Leu Ile Glu Gln Leu Ser Gln Val Gly Lys Pro Leu Val Val Leu Gln
            530                 535                 540

Met Gly Gly Gly Gln Val Asp Ser Ser Ser Leu Lys Ala Asn Lys Asn
545                 550                 555                 560

Val Asn Ala Leu Val Trp Gly Gly Tyr Pro Gly Gln Ser Gly Gly Ala
                565                 570                 575

Ala Leu Phe Asp Ile Leu Thr Gly Lys Arg Ala Pro Ala Gly Arg Leu
            580                 585                 590

Val Ser Thr Gln Tyr Pro Ala Glu Tyr Ala Thr Gln Phe Pro Ala Asn
            595                 600                 605

Asp Met Asn Leu Arg Pro Asn Gly Ser Asn Pro Gly Gln Thr Tyr Ile
            610                 615                 620

Trp Tyr Thr Gly Thr Pro Val Tyr Glu Phe Gly His Gly Leu Phe Tyr
625                 630                 635                 640

Thr Glu Phe Gln Glu Ser Ala Ala Ala Gly Thr Asn Lys Thr Ser Thr
                645                 650                 655

Phe Asp Ile Leu Asp Leu Phe Ser Thr Pro His Pro Gly Tyr Glu Tyr
            660                 665                 670

Ile Glu Gln Val Pro Phe Ile Asn Val Thr Val Asp Val Lys Asn Val
            675                 680                 685

Gly His Thr Pro Ser Pro Tyr Thr Gly Leu Leu Phe Ala Asn Thr Thr
            690                 695                 700

Ala Gly Pro Lys Pro Tyr Pro Asn Lys Trp Leu Val Gly Phe Asp Trp
705                 710                 715                 720

Leu Pro Thr Ile Gln Pro Gly Glu Thr Ala Lys Leu Thr Ile Pro Val
                725                 730                 735

Pro Leu Gly Ala Ile Ala Trp Ala Asp Glu Asn Gly Asn Lys Val Val
            740                 745                 750
```

```
Phe Pro Gly Asn Tyr Glu Leu Ala Leu Asn Asn Glu Arg Ser Val Val
        755                 760                 765

Val Ser Phe Thr Leu Thr Gly Asp Ala Ala Thr Leu Glu Lys Trp Pro
    770                 775                 780

Leu Trp Glu Gln Ala Val Pro Gly Val Leu Gln Gln
785                 790                 795
```

POLYPEPTIDES HAVING CELLULOLYTIC ENHANCING ACTIVITY AND POLYNUCLEOTIDES ENCODING SAME

CROSS-REFERENCE TO RELATED APPLICATIONS

This application is a 35 U.S.C. § 371 national application of PCT/CN2012/083853 filed on Oct. 31, 2012, which claims priority or the benefit under 35 U.S.C. § 119 of PCT/CN2011/081564 filed on Oct. 31, 2011 and U.S. Provisional Application No. 61/565,776 filed on Dec. 1, 2011, the contents of which are fully incorporated herein by reference.

STATEMENT AS TO RIGHTS TO INVENTIONS MADE UNDER FEDERALLY SPONSORED RESEARCH AND DEVELOPMENT

This invention was made with Government support under Cooperative Agreement DE-FC36-08GO18080 awarded by the Department of Energy. The government has certain rights in this invention.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having cellulolytic enhancing activity, catalytic domains, and cellulose binding domains, and polynucleotides encoding the polypeptides, catalytic domains, and cellulose binding domains. The invention also relates to nucleic acid constructs, vectors, and host cells comprising the polynucleotides as well as methods of producing and using the polypeptides, catalytic domains, and cellulose binding domains.

Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose. Once the cellulose is converted to glucose, the glucose can easily be fermented by yeast into ethanol.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin.

WO 2005/074647, WO 2008/148131, and WO 2011/035027 disclose GH61 polypeptides having cellulolytic enhancing activity and the polynucleotides thereof from *Thielavia terrestris*. WO 2005/074656 and WO 2010/065830 disclose GH61 polypeptides having cellulolytic enhancing activity and the polynucleotides thereof from *Thermoascus aurantiacus*. WO 2007/089290 discloses a GH61 polypeptide having cellulolytic enhancing activity and the polynucleotide thereof from *Trichoderma reesei*. WO 2009/085935, WO 2009/085859, WO 2009/085864, and WO 2009/085868 disclose GH61 polypeptides having cellulolytic enhancing activity and the polynucleotides thereof from *Myceliophthora thermophila*. WO 2010/138754 discloses a GH61 polypeptide having cellulolytic enhancing activity and the polynucleotide thereof from *Aspergillus fumigatus*. WO 2011/005867 discloses a GH61 polypeptide having cellulolytic enhancing activity and the polynucleotide thereof from *Penicillium pinophilum*. WO 2011/039319 discloses a GH61 polypeptide having cellulolytic enhancing activity and the polynucleotide thereof from *Thermoascus* sp. WO 2011/041397 discloses a GH61 polypeptide having cellulolytic enhancing activity and the polynucleotide thereof from *Penicillium* sp. (*emersonii*). WO 2011/041504 discloses GH61 polypeptides having cellulolytic enhancing activity and the polynucleotides thereof from *Thermoascus crustaceus*. WO 2012/030799 discloses GH61 polypeptides having cellulolytic enhancing activity and the polynucleotides thereof from *Aspergillus aculeatus*. WO 2008/151043 discloses methods of increasing the activity of a GH61 polypeptide having cellulolytic enhancing activity by adding a soluble activating divalent metal cation to a composition comprising the polypeptide.

There is a need in the art for new enzymes to increase efficiency and to provide cost-effective enzyme solutions for saccharification of cellulosic material.

The present invention provides GH61 polypeptides having cellulolytic enhancing activity and polynucleotides encoding the polypeptides.

SUMMARY OF THE INVENTION

The present invention relates to isolated polypeptides having cellulolytic enhancing activity selected from the group consisting of:

(a) a polypeptide having at least 60% sequence identity to the mature polypeptide of SEQ ID NO: 2; at least 75% sequence identity to the mature polypeptide of SEQ ID NO: 12 or SEQ ID NO: 22; at least 80% sequence identity to the mature polypeptide of SEQ ID NO: 4, SEQ ID NO: 10, or SEQ ID NO: 24; at least 85% sequence identity to the mature polypeptide of SEQ ID NO: 6, SEQ ID NO: 16, or SEQ ID NO: 28; or at least 90% sequence identity to the mature polypeptide of SEQ ID NO: 8, SEQ ID NO: 14, SEQ ID NO: 18, SEQ ID NO: 20, SEQ ID NO: 26, SEQ ID NO: 30, or SEQ ID NO: 32;

(b) a polypeptide encoded by a polynucleotide that hybridizes under at least medium-high stringency conditions with (i) the mature polypeptide coding sequence of SEQ ID NO: 1, or (ii) the full-length complement of (i); or at least high stringency conditions with (i) the mature polypeptide coding sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, or SEQ ID NO: 31, (ii) the cDNA sequence of SEQ ID NO: 3, SEQ ID NO: 5, SEQ ID NO: 7, SEQ ID NO: 11, SEQ ID NO: 13, SEQ ID NO: 15, SEQ ID NO: 17, SEQ ID NO: 19, SEQ ID NO: 23, SEQ ID NO: 25, SEQ ID NO: 27, SEQ ID NO: 29, or SEQ ID NO: 31, or (iii) the full-length complement of (i) or (ii);

(c) a polypeptide encoded by a polynucleotide having at least 60% sequence identity to the mature polypeptide coding sequence of SEQ ID NO: 1; at least 75% sequence identity to the mature polypeptide coding sequence of SEQ ID NO: 11 or the cDNA sequence thereof, or SEQ ID NO: 21; at least 80% sequence identity to the mature polypeptide coding sequence of SEQ ID NO: 3 or the cDNA sequence thereof, SEQ ID NO: 9, or SEQ ID NO: 23 or the cDNA sequence thereof; at least 85% sequence identity to the mature polypeptide coding sequence of SEQ ID NO: 5, SEQ ID NO: 15, or SEQ ID NO: 27, or the cDNA sequences thereof; or at least 90% sequence identity to the mature polypeptide coding sequence of SEQ ID NO: 7, SEQ ID NO: 13, SEQ ID NO: 17, SEQ ID NO: 19, SEQ ID NO: 25, SEQ ID NO: 29, or SEQ ID NO: 31, or the cDNA sequences thereof;

(d) a variant of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, or SEQ ID NO: 32 comprising a substitution, deletion, and/or insertion at one or more (e.g., several) positions; and (e) a fragment of the polypeptide of (a), (b), (c), or (d) that has cellulolytic enhancing activity.

The present invention also relates to isolated polypeptides comprising a catalytic domain selected from the group consisting of:

(a) a catalytic domain having at least 80% sequence identity to amino acids 20 to 251 of SEQ ID NO: 10 or amino acids 21 to 244 of SEQ ID NO: 24; at least 85% sequence identity to amino acids 19 to 241 of SEQ ID NO: 28, or at least 90% sequence identity to amino acids 16 to 243 of SEQ ID NO: 32;

(b) a catalytic domain encoded by a polynucleotide that hybridizes under at least high stringency conditions with (i) nucleotides 58 to 753 of SEQ ID NO: 9, nucleotides 61 to 792 of SEQ ID NO: 23 or the cDNA sequence thereof, nucleotides 55 to 803 of SEQ ID NO: 27 or the cDNA sequence thereof, nucleotides 46 to 1008 of SEQ ID NO: 31 or the cDNA sequence thereof, or (ii) the full-length complement of (i);

(c) a catalytic domain encoded by a polynucleotide having at least 80% sequence identity to nucleotides 58 to 753 of SEQ ID NO: 9, or nucleotides 61 to 792 of SEQ ID NO: 23 or the cDNA sequence thereof, at least 85% sequence identity to nucleotides 55 to 803 of SEQ ID NO: 27 or the cDNA sequence thereof, or at least 90% sequence identity to nucleotides 46 to 1008 of SEQ ID NO: 31 or the cDNA sequence thereof;

(d) a variant of amino acids 20 to 251 of SEQ ID NO: 10, amino acids 21 to 244 of SEQ ID NO: 24, amino acids 19 to 241 of SEQ ID NO: 28, or amino acids 16 to 243 of SEQ ID NO: 32 comprising a substitution, deletion, and/or insertion at one or more (e.g., several) positions; and (e) a fragment of the catalytic domain of (a), (b), (c), or (d) that has cellulolytic enhancing activity.

The present invention also relates to isolated polypeptides comprising a cellulose binding domain selected from the group consisting of:

(a) a cellulose binding domain having at least 80% sequence identity to amino acids 304 to 332 of SEQ ID NO: 10 or amino acids 282 to 337 of SEQ ID NO: 24, at least 85% sequence identity to amino acids 291 to 319 of SEQ ID NO: 28, or at least 90% sequence identity to amino acids 274 to 301 of SEQ ID NO: 32;

(b) a cellulose binding domain encoded by a polynucleotide that hybridizes under at least high stringency conditions with (i) nucleotides 910 to 996 of SEQ ID NO: 9, nucleotides 904 to 1071 of SEQ ID NO: 23, nucleotides 951 to 1107 of SEQ ID NO: 27 or the cDNA sequence thereof, or nucleotides 1099 to 1182 of SEQ ID NO: 31, or (ii) the full-length complement of (i);

(c) a cellulose binding domain encoded by a polynucleotide having at least 80% sequence identity to nucleotides 910 to 996 of SEQ ID NO: 9 or nucleotides 904 to 1071 of SEQ ID NO: 23, at least 85% sequence identity to nucleotides 951 to 1107 of SEQ ID NO: 27 or the cDNA sequence thereof, or at least 90% sequence identity to nucleotides 1099 to 1182 of SEQ ID NO: 31;

(d) a variant of amino acids 304 to 332 of SEQ ID NO: 10, amino acids 282 to 337 of SEQ ID NO: 24, amino acids 291 to 319 of SEQ ID NO: 28, or amino acids 274 to 301 of SEQ ID NO: 32 comprising a substitution, deletion, and/or insertion at one or more (e.g., several) positions; and (e) a fragment of the cellulose binding domain of (a), (b), (c), or (d) that has binding activity.

The present invention also relates to isolated polynucleotides encoding the polypeptides of the present invention; nucleic acid constructs, recombinant expression vectors, and recombinant host cells comprising the polynucleotides; and methods of producing the polypeptides.

The present invention also relates to processes for degrading a cellulosic material, comprising: treating the cellulosic material with an enzyme composition in the presence of a polypeptide having cellulolytic enhancing activity of the present invention.

The present invention also relates to processes of producing a fermentation product, comprising: (a) saccharifying a cellulosic material with an enzyme composition in the presence of a polypeptide having cellulolytic enhancing activity of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a polypeptide having cellulolytic enhancing activity of the present invention.

The present invention also relates to an isolated polynucleotide encoding a signal peptide comprising or consisting of amino acids 1 to 23 of SEQ ID NO: 2, amino acids 1 to 20 of SEQ ID NO: 4, amino acids 1 to 20 of SEQ ID NO: 6, amino acids 1 to 15 of SEQ ID NO: 8, amino acids 1 to 19 of SEQ ID NO: 10, amino acids 1 to 16 of SEQ ID NO: 12, amino acids 1 to 17 of SEQ ID NO: 14, amino acids 1 to 17 of SEQ ID NO: 16, amino acids 1 to 15 of SEQ ID NO: 18, amino acids 1 to 17 of SEQ ID NO: 20, amino acids 1 to 21 of SEQ ID NO: 22, amino acids 1 to 20 of SEQ ID NO: 24, amino acids 1 to 17 of SEQ ID NO: 26, amino acids 1 to 18 of SEQ ID NO: 28, amino acids 1 to 20 of SEQ ID NO: 30, or amino acids 1 to 15 of SEQ ID NO: 32, which is operably linked to a gene encoding a protein, wherein the protein is foreign to the signal peptide; nucleic acid constructs, expression vectors, and recombinant host cells comprising the polynucleotides; and methods of producing a protein.

DEFINITIONS

Figure 1:
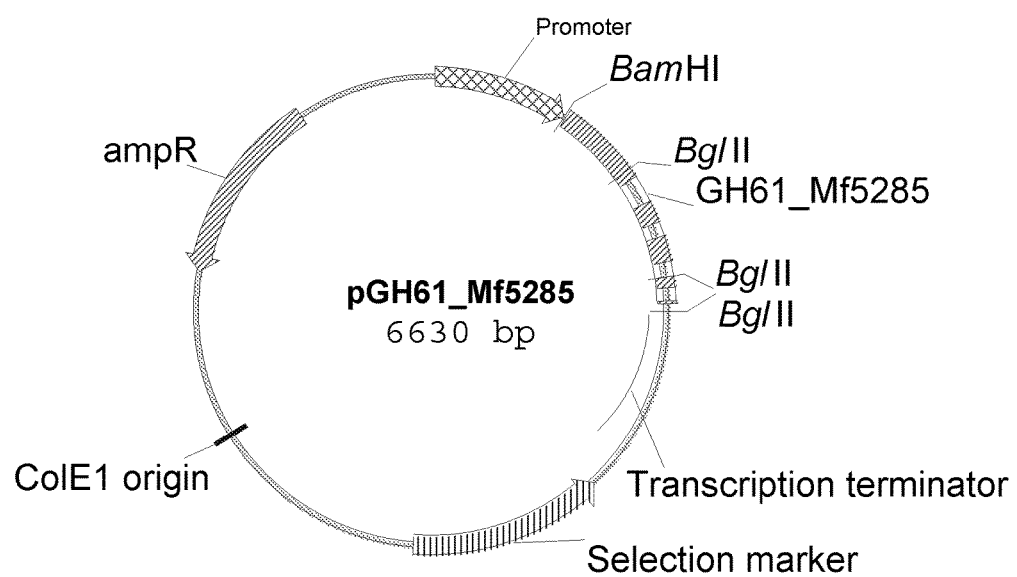
FIG. 1 shows a restriction map of plasmid of pGH61_Mf5285.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 μmole of glucuronic or 4-O-methylglucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 μmole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Carbohydrate binding domain: The term "carbohydrate binding domain" means the region of an enzyme that mediates binding of the enzyme to amorphous regions of a cellulose substrate. The carbohydrate binding domain (CBD) is typically found either at the N-terminal or at the C-terminal extremity of an enzyme. The term "cellulose binding domain" is used interchangeably herein with carbohydrate binding domain.

Catalytic domain: The term "catalytic domain" means the region of an enzyme containing the catalytic machinery of the enzyme.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581. In the present invention, the Tomme et al. method can be used to determine cellobiohydrolase activity.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No. 1 filter paper, microcrystalline cellulose, bacterial cellulose, algal cellulose, cotton, pretreated lignocellulose, etc. The most common total cellulolytic activity assay is the filter paper assay using Whatman No. 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al, 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of a mature polypeptide; wherein the fragment has cellulolytic enhancing activity. In one aspect, a fragment contains at least 255 amino acid residues, e.g., at least 270 amino acid residues or at least 285 amino acid residues of SEQ ID NO: 2. In another aspect, a fragment contains at least 190 amino acid residues, e.g., at least 200 amino acid residues or at least 210 amino acid residues of SEQ ID NO: 4. In another aspect, a fragment contains at least 170 amino acid residues, e.g., at least 180 amino acid residues or at least 190 amino acid residues of SEQ ID NO: 6. In another aspect, a fragment contains at least 190 amino acid residues, e.g., at least 200 amino acid residues or at least 210 amino acid residues of SEQ ID NO: 8. In another aspect, a fragment contains at least 270 amino acid residues, e.g., at least 285 amino acid residues or at least 300 amino acid residues of SEQ ID NO: 10. In another aspect, a fragment contains at least 210 amino acid residues, e.g., at least 220 amino acid residues or at least 230 amino acid residues of SEQ ID NO: 12. In another aspect, a fragment contains at least 200 amino acid residues, e.g., at least 210 amino acid residues or at least 220 amino acid residues of SEQ ID NO: 14. In another aspect, a fragment contains at least 180 amino acid residues, e.g., at least 190 amino acid residues or at least 200 amino acid residues of SEQ ID NO: 16. In another aspect, a fragment contains at least 190 amino acid residues, e.g., at least 200 amino acid residues or at least 210 amino acid residues of SEQ ID NO: 18. In another aspect, a fragment contains at least 180 amino acid residues, e.g., at least 190 amino acid residues or at least 200 amino acid residues of SEQ ID NO: 20. In another aspect, a fragment contains at least 245 amino acid residues, e.g., at least 260 amino acid residues or at least 275 amino acid residues of SEQ ID NO: 22. In another aspect, a fragment contains at least 360 amino acid residues, e.g., at least 380 amino acid residues or at least 400 amino acid residues of SEQ ID NO: 24. In another aspect, a fragment contains at least 200 amino acid residues, e.g., at least 210 amino acid residues or at least 220 amino acid residues of SEQ ID NO: 26. In another aspect, a fragment contains at least 255 amino acid residues, e.g., at least 270 amino acid residues or at least 285 amino acid residues of SEQ ID NO: 28. In another aspect, a fragment contains at least 190 amino acid residues, e.g., at least 200 amino acid residues or at least 210 amino acid residues of SEQ ID NO: 30. In another aspect, a fragment contains at least 245 amino acid residues, e.g., at least 260 amino acid residues or at least 275 amino acid residues of SEQ ID NO: 32.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. Current Opinion In Microbiology, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 24 to 324 of SEQ ID NO: 2 (P24MRR) based on the SignalP program (Nielsen et al., 1997, *Protein Engineering* 10: 1-6) that predicts amino acids 1 to 23 of SEQ ID NO: 2 are a signal peptide. In another aspect, the mature polypeptide is amino acids 21 to 240 of SEQ ID NO: 4 based on the SignalP program that predicts amino acids 1 to 20 of SEQ ID NO: 4 are a signal peptide. In another aspect, the mature polypeptide is amino acids 21 to 225 of SEQ ID NO: 6 (P24MDK) based on the SignalP program that predicts amino acids 1 to 20 of SEQ ID NO: 6 are a signal peptide. In another aspect, the mature polypeptide is amino acids 16 to 235 of SEQ ID NO: 8 (P24MDM) based on the SignalP program that predicts amino acids 1 to 15 of SEQ ID NO: 8 are a signal peptide. In another aspect, the mature polypeptide is amino acids 20 to 336 of SEQ ID NO: 10 (P24MRY) based on the SignalP program that predicts amino acids 1 to 19 of SEQ ID NO: 10 are a signal peptide. In another aspect, the mature polypeptide is amino acids 17 to 253 of SEQ ID NO: 12 (P24MRT) based on the SignalP program that predicts amino acids 1 to 16 of SEQ ID NO: 12 are a signal peptide. In another aspect, the mature polypeptide is amino acids 18 to 255 of SEQ ID NO: 14 (P24MDQ) based on the SignalP program that predicts amino acids 1 to 17 of SEQ ID NO: 14 are a signal peptide. In another aspect, the mature polypeptide is amino acids 18 to 225 of SEQ ID NO: 16 (P24MDR) based on the SignalP program that predicts amino acids 1 to 17 of SEQ ID NO: 16 are a signal peptide. In another aspect, the mature polypeptide is amino acids 16 to 237 of SEQ ID NO: 18 (P24QE1) based on the SignalP program that predicts amino acids 1 to 15 of SEQ ID NO: 18 are a signal peptide. In another aspect, the mature polypeptide is amino acids 18 to 227 of SEQ ID NO: 20 (P24MDS) based on the SignalP program that predicts amino acids 1 to 17 of SEQ ID NO: 20 are a signal peptide. In another aspect, the mature polypeptide is amino acids 22 to 315 of SEQ ID NO: 22 (P24GU3) based on the SignalP program that predicts amino acids 1 to 21 of SEQ ID NO: 22 are a signal peptide. In another aspect, the mature polypeptide is amino acids 21 to 439 of SEQ ID NO: 24 (P24MDT) based on the SignalP program that predicts amino acids 1 to 20 of SEQ ID NO: 24 are a signal peptide. In another aspect, the mature polypeptide is amino acids 18 to 246 of SEQ ID NO: 26 (P24MDU) based on the SignalP program that predicts amino acids 1 to 17 of SEQ ID NO: 26 are a signal peptide. In another aspect, the mature polypeptide is amino acids 19 to 324 of SEQ ID NO: 28 (P24QE3) based on the SignalP program that predicts amino acids 1 to 18 of SEQ ID NO: 28 are a signal peptide. In another aspect, the mature polypeptide is amino acids 21 to 242 of SEQ ID NO: 30 (P24MRW) based on the SignalP program that predicts amino acids 1 to 20 of SEQ ID NO: 30 are a signal peptide. In another aspect, the mature polypeptide is amino acids 16 to 306 of SEQ ID NO: 32 (P24MRX) based on the SignalP program that predicts amino acids 1 to 15 of SEQ ID NO: 32 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having cellulolytic enhancing activity. In one aspect, the mature polypeptide coding sequence is nucleotides 70 to 972 of SEQ ID NO: 1 (D1321N) or the cDNA sequence thereof based on the SignalP program (Nielsen et al., 1997, supra) that predicts nucleotides 1 to 69 of SEQ ID NO: 1 encode a signal peptide. In another aspect, the mature polypeptide coding sequence is nucleotides 61 to 1112 of SEQ ID NO: 3 or the cDNA sequence thereof based on the SignalP program that predicts nucleotides 1 to 60 of SEQ ID NO: 3 encode a signal peptide. In another aspect, the mature polypeptide coding sequence is nucleotides 61 to 985 of SEQ ID NO: 5 (D1317F) or the cDNA sequence thereof based on the SignalP program that predicts nucleotides 1 to 60 of SEQ ID NO: 5 encode a signal peptide. In another aspect, the mature polypeptide coding sequence is nucleotides 46 to 856 of SEQ ID NO: 7 (D1317G) or the cDNA sequence thereof based on the SignalP program that predicts nucleotides 1 to 45 of SEQ ID NO: 7 encode a signal peptide. In another aspect, the mature polypeptide coding sequence is nucleotides 58 to 1008 of SEQ ID NO: 9 (D1321V) or the cDNA sequence thereof based on the SignalP program that predicts nucleotides 1 to 57 of SEQ ID NO: 9 encode a signal peptide. In another aspect, the mature polypeptide coding sequence is nucleotides 49 to 1312 of SEQ ID NO: 11 (D1321Q) or the cDNA sequence thereof based on the SignalP program that predicts nucleotides 1 to 48 of SEQ ID NO: 11 encode a signal peptide. In another aspect, the mature polypeptide coding sequence is nucleotides 52 to 921 of SEQ ID NO: 13 (D1317K) or the cDNA sequence thereof based on the SignalP program that predicts nucleotides 1 to 51 of SEQ ID NO: 13 encode a signal peptide. In another aspect, the mature polypeptide coding sequence is nucleotides 52 to 739 of SEQ ID NO: 15 (D1317M) or the cDNA sequence thereof based on the SignalP program that predicts nucleotides 1 to 51 of SEQ ID NO: 15 encode a signal peptide. In another aspect, the mature polypeptide coding sequence is nucleotides 46 to 898 of SEQ ID NO: 17 (D137US) or the cDNA sequence thereof based on the SignalP program that predicts nucleotides 1 to 45 of SEQ ID NO: 17 encode a signal peptide. In another aspect, the mature polypeptide coding sequence is nucleotides 52 to 941 of SEQ ID NO: 19 (D1317P) or the cDNA sequence thereof based on the SignalP program that predicts nucleotides 1 to 51 of SEQ ID NO: 19 encode a signal peptide. In another aspect, the mature polypeptide coding sequence is nucleotides 64 to 945 of SEQ ID NO: 21 (D1321R) or the cDNA sequence thereof based on the SignalP program that predicts nucleotides 1 to 63 of SEQ ID NO: 21 encode a signal peptide. In another aspect, the mature polypeptide coding sequence is nucleotides 61 to 1377 of SEQ ID NO: 23 (D1317Q) or the cDNA sequence thereof based on the SignalP program that predicts nucleotides 1 to 60 of SEQ ID NO: 23 encode a signal peptide. In another aspect, the mature polypeptide coding sequence is nucleotides 52 to 818 of SEQ ID NO: 25 (D1317R) or the cDNA sequence thereof based on the SignalP program that predicts nucleotides 1 to 51 of SEQ ID NO: 25 encode a signal peptide. In another aspect, the mature polypeptide coding sequence is nucleotides 55 to 1122 of SEQ ID NO: 27 (D137UU) or the cDNA sequence thereof based on the SignalP program that predicts nucleotides 1 to 54 of SEQ ID NO: 27 encode a signal peptide. In another aspect, the mature polypeptide coding sequence is nucleotides 60 to 1034 of SEQ ID NO: 29 (D1321T) or the cDNA sequence thereof based on the SignalP program that predicts nucleotides 1 to 61 of SEQ ID NO: 29 encode a signal peptide. In another aspect, the mature polypeptide coding sequence is nucleotides 46 to 1197 of SEQ ID NO: 31 (D1321U) or the cDNA sequence thereof based on the SignalP program that predicts nucleotides 1 to 45 of SEQ ID NO: 31 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and a suitable pH such 4-9, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity. Cellulolytic enhancing activity can also be determined according to the procedure described in Example 5 herein.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

The polypeptides of the present invention have at least 20%, e.g., at least 40%, at least 50%, at least 60%, at least 70%, at least 80%, at least 90%, at least 95%, and at least 100% of the cellulolytic enhancing activity of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, or SEQ ID NO: 32.

Pretreated corn stover: The term "PCS" or "Pretreated Corn Stover" means a cellulosic material derived from corn stover by treatment with heat and dilute sulfuric acid, alkaline pretreatment, or neutral pretreatment.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0, 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0, 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having cellulolytic enhancing activity. In one aspect, a subsequence contains at least 765 nucleotides, e.g., at least 810 nucleotides or at least 855 nucleotides of SEQ ID NO: 1. In another aspect, a subsequence contains at least 570 nucleotides, e.g., at least 600 nucleotides or at least 630 nucleotides of SEQ ID NO: 3. In another aspect, a subsequence contains at least 510 nucleotides, e.g., at least 540 nucleotides or at least 570 nucleotides of SEQ ID NO: 5. In another aspect, a subsequence contains at least 570 nucleotides, e.g., at least 600 nucleotides or at least 630 nucleotides of SEQ ID NO: 7. In another aspect, a subsequence contains at least 810 nucleotides, e.g., at least 855 nucleotides or at least 900 nucleotides of SEQ ID NO: 9. In another aspect, a subsequence contains at least 630 nucleotides, e.g., at least 660 nucleotides or at least 690 nucleotides of SEQ ID NO: 11. In another aspect, a subsequence contains at least 600 nucleotides, e.g., at least 630 nucleotides or at least 660 nucleotides of SEQ ID NO: 13. In another aspect, a subsequence contains at least 540 nucleotides, e.g., at least 570 nucleotides or at least 600 nucleotides of SEQ ID NO: 15. In another aspect, a subsequence contains at least 570 nucleotides, e.g., at least 600 nucleotides or at least 630 nucleotides of SEQ ID NO: 17. In another aspect, a subsequence contains at least 540 nucleotides, e.g., at least 570 nucleotides or at least 600 nucleotides of SEQ ID NO: 19. In another aspect, a subsequence contains at least 735 nucleotides, e.g., at least 780 nucleotides or at least 825 nucleotides of SEQ ID NO: 21. In another aspect, a subsequence contains at least 1080 nucleotides, e.g., at least 1140 nucleotides or at least 1200 nucleotides of SEQ ID NO: 23. In another aspect, a subsequence contains at least 600 nucleotides, e.g., at least 630 nucleotides or at least 660 nucleotides of SEQ ID NO: 25. In another aspect, a subsequence contains at least 765 nucleotides, e.g., at least 810 nucleotides or at least 855 nucleotides of SEQ ID NO: 27. In another aspect, a subsequence contains at least 570 nucleotides, e.g., at least 600 nucleotides or at least 630 nucleotides of SEQ ID NO: 29. In another aspect, a subsequence contains at least 735 nucleotides, e.g., at least 780 nucleotides or at least 825 nucleotides of SEQ ID NO: 31.

Variant: The term "variant" means a polypeptide having cellulolytic enhancing activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, Recent progress in the assays of xylanolytic enzymes, *Journal of the Science of Food and Agriculture* 86(11): 1636-1647; Spanikova and Biely, 2006, Glucuronoyl esterase—Novel carbohydrate esterase produced by *Schizophyllum commune*, *FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

DETAILED DESCRIPTION OF THE INVENTION

Polypeptides Having Cellulolytic Enhancing Activity

In an embodiment, the present invention relates to isolated polypeptides having a sequence identity to the mature polypeptide of SEQ ID NO: 2 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 12 or SEQ ID NO: 22 of at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 4, SEQ ID NO: 10, or SEQ ID NO: 24 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; mature polypeptide of SEQ ID NO: 6, SEQ ID NO: 16, or SEQ ID NO: 28 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%; or the mature polypeptide of SEQ ID NO: 8, SEQ ID NO: 14, SEQ ID NO: 18, SEQ ID NO: 20, SEQ ID NO: 26, SEQ ID NO: 30, or SEQ ID NO: 32 of at least 90%, e.g., at least 91%, at least 92%, at least 93%, at least 94%, at least 95%, at least 96%, at least 97%, at least 98%, at least 99%, or 100%.

A polypeptide of the present invention preferably comprises or consists of the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, or SEQ ID NO: 32 or an allelic variant thereof; or is a fragment thereof having cellulolytic enhancing activity. In another aspect, the polypeptide comprises or consists of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, or SEQ ID NO: 32. In another aspect, the polypeptide comprises or consists of amino acids 24 to 324 of SEQ ID NO: 2, amino acids 21 to 240 of SEQ ID NO: 4, amino acids 21 to 225 of SEQ ID NO: 6, amino acids 16 to 235 of SEQ ID NO: 8, amino acids 20 to 336 of SEQ ID NO: 10, amino acids 17 to 253 of SEQ ID NO: 12, amino acids 18 to 255 of SEQ ID NO: 14, amino acids 18 to 225 of SEQ ID NO: 16, amino acids 16 to 237 of SEQ ID NO: 18, amino acids 18 to 227 of SEQ ID NO: 20, amino acids 22 to 315 of SEQ ID NO: 22, amino acids 21 to 439 of SEQ ID NO: 24, amino acids 18 to 246 of SEQ ID NO: 26, amino acids 19 to 324 of SEQ ID NO: 28, amino acids 21 to 242 of SEQ ID NO: 30, or amino acids 16 to 306 of SEQ ID NO: 32.

In another embodiment, the present invention relates an isolated polypeptides having cellulolytic enhancing activity encoded by polynucleotides that hybridize under very low stringency conditions, low stringency conditions, medium stringency conditions, medium-high stringency conditions, high stringency conditions, or very high stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, or SEQ ID NO: 31, (ii) the cDNA sequence of SEQ ID NO: 3, SEQ ID NO: 5, SEQ ID NO: 7, SEQ ID NO: 11, SEQ ID NO: 13, SEQ ID NO: 15, SEQ ID NO: 17, SEQ ID NO: 19, SEQ ID NO: 23, SEQ ID NO: 25, SEQ ID NO: 27, SEQ ID NO: 29, or SEQ ID NO: 31 or (iii) the full-length complement of (i) or (ii) (Sambrook et al., 1989, *Molecular Cloning, A Laboratory Manual*, 2d edition, Cold Spring Harbor, N.Y.).

The polynucleotide of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, or SEQ ID NO: 31, or a subsequence thereof, as well as the polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, or SEQ ID NO: 32, or a fragment thereof, may be used to design nucleic acid probes to identify and clone DNA encoding polypeptides having cellulolytic enhancing activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having cellulolytic enhancing activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, or SEQ ID NO: 31, the mature polypeptide coding sequence thereof, or a subsequence thereof, the carrier material is used in a Southern blot.

For purposes of the present invention, hybridization indicates that the polynucleotides hybridize to a labeled nucleic acid probe corresponding to (i) SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, or SEQ ID NO: 31; (ii) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, or SEQ ID NO: 31; (iii) the cDNA sequence of SEQ ID NO: 3, SEQ ID NO: 5, SEQ ID NO: 7, SEQ ID NO: 11, SEQ ID NO: 13, SEQ ID NO: 15, SEQ ID NO: 17, SEQ ID NO: 19, SEQ ID NO: 23, SEQ ID NO: 25, SEQ ID NO: 27, SEQ ID NO: 29, or SEQ ID NO: 31; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is a polynucleotide that encodes the polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, or SEQ ID NO: 32; the mature polypeptide thereof; or a fragment thereof. In another aspect, the nucleic acid probe is SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, or SEQ ID NO: 31; the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, or SEQ ID NO: 31; or the cDNA sequence of SEQ ID NO: 3, SEQ ID NO: 5, SEQ ID NO: 7, SEQ ID NO: 11, SEQ ID NO: 13, SEQ ID NO: 15, SEQ ID NO: 17, SEQ ID NO: 19, SEQ ID NO: 23, SEQ ID NO: 25, SEQ ID NO: 27, SEQ ID NO: 29, or SEQ ID NO: 31. In another aspect, the nucleic acid probe is the polynucleotide contained in *Corynascus thermophilus* CBS 174.70, wherein the polynucleotide encodes a polypeptide having cellulolytic enhancing activity. In another aspect, the nucleic acid probe is the mature polypeptide coding region contained in *Corynascus thermophilus* CBS 174.70.

In another embodiment, the present invention relates to isolated polypeptides having cellulolytic enhancing activity encoded by polynucleotides having a sequence identity to the mature polypeptide coding sequence of SEQ ID NO: 1 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide coding sequence of SEQ ID NO: 11 or the cDNA sequence thereof, or SEQ ID NO: 21 of at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide coding sequence of SEQ ID NO: 3 or the cDNA sequence thereof, SEQ ID NO: 9, or SEQ ID NO: 23 or the cDNA sequence thereof, of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; mature polypeptide coding sequence of SEQ ID NO: 5, SEQ ID NO: 15, or SEQ ID NO: 27, or the cDNA sequences thereof, of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%; or the mature polypeptide coding sequence of SEQ ID NO: 7, SEQ ID NO: 13, SEQ ID NO: 17, SEQ ID NO: 19, SEQ ID NO: 25, SEQ ID NO: 29, or SEQ ID NO: 31, or the cDNA sequences thereof, of at least 90%, e.g., at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, or SEQ ID NO: 32 comprising a substitution, deletion, and/or insertion at one or more (e.g., several) positions. In an aspect, the number of amino acid substitutions, deletions and/or insertions introduced into the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, or SEQ ID NO: 32 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for cellulolytic enhancing activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a *hybrid* polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al, 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Cellulolytic Enhancing Activity

A polypeptide having cellulolytic enhancing activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. In one aspect, the polypeptide is a *Corynascus* polypeptide. In another aspect, the polypeptide is a *Corynascus thermophilus* polypeptide. In another aspect, the polypeptide is a *Corynascus thermophilus* CBS 174.70 polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Catalytic Domains

In one embodiment, the present invention also relates to catalytic domains having a sequence identity to amino acids 20 to 251 of SEQ ID NO: 12 or amino acids 21 to 244 of SEQ ID NO: 24 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; amino acids 19 to 241 of SEQ ID NO: 28 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%; or amino acids 16 to 243 of SEQ ID NO: 32 of at least 90%, e.g., at least 91%, at least 92%, at least 93%, at least 94%, at least 95%, at least 96%, at least 97%, at least 98%, at least 99%, or 100%. In one aspect, the catalytic domains comprise amino acid sequences that differ by up to 10 amino acids, e.g., 1, 2, 3, 4, 5, 6, 7, 8, 9, or 10, from amino acids 20 to 251 of SEQ ID NO: 10, amino acids 21 to 244 of SEQ ID NO: 24, amino acids 19 to 241 of SEQ ID NO: 28, or amino acids 16 to 243 of SEQ ID NO: 32.

The catalytic domain preferably comprises or consists of amino acids 20 to 251 of SEQ ID NO: 10, amino acids 21 to 244 of SEQ ID NO: 24, amino acids 19 to 241 of SEQ ID NO: 28, or amino acids 16 to 243 of SEQ ID NO: 32, or an allelic variant thereof; or is a fragment thereof having cellulolytic enhancing activity.

In another embodiment, the present invention also relates to catalytic domains encoded by polynucleotides that hybridize under very low stringency conditions, low stringency conditions, medium stringency conditions, medium-high stringency conditions, high stringency conditions, or very high stringency conditions (as defined above) with (i) nucleotides 58 to 753 of SEQ ID NO: 9, nucleotides 61 to 792 of SEQ ID NO: 23 or the cDNA sequence thereof, nucleotides 55 to 803 of SEQ ID NO: 27 or the cDNA sequence thereof, nucleotides 46 to 1008 of SEQ ID NO: 31 or the cDNA sequence thereof, or (ii) the full-length complement of (i) (Sambrook et al., 1989, supra).

In another embodiment, the present invention also relates to catalytic domains encoded by polynucleotides having a sequence identity to nucleotides 58 to 753 of SEQ ID NO: 9, or nucleotides 61 to 792 of SEQ ID NO: 23 or the cDNA sequence thereof of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; nucleotides 55 to 803 of SEQ ID NO: 27 or the cDNA sequence thereof of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%; or nucleotides 46 to 1008 of SEQ ID NO: 31 or the cDNA sequence thereof of at least 90%, e.g., at least 91%, at least 92%, at least 93%, at least 94%, at least 95%, at least 96%, at least 97%, at least 98%, at least 99%, or 100%.

The polynucleotide encoding the catalytic domain preferably comprises or consists of nucleotides 58 to 753 of SEQ ID NO: 9, nucleotides 61 to 792 of SEQ ID NO: 23 or the cDNA sequence thereof, nucleotides 55 to 803 of SEQ ID NO: 27 or the cDNA sequence thereof, nucleotides 46 to 1008 of SEQ ID NO: 31 or the cDNA sequence thereof, or is the sequence contained in *Corynascus thermophilus* CBS 174.70.

In another embodiment, the present invention also relates to catalytic domain variants of amino acids 20 to 251 of SEQ ID NO: 10, amino acids 21 to 244 of SEQ ID NO: 24, amino acids 19 to 241 of SEQ ID NO: 28, or amino acids 16 to 243 of SEQ ID NO: 32, comprising a substitution, deletion, and/or insertion at one or more (e.g., several) positions. In one aspect, the number of amino acid substitutions, deletions and/or insertions introduced into the sequence of amino acids 20 to 251 of SEQ ID NO: 10, amino acids 21 to 244 of SEQ ID NO: 24, amino acids 19 to 241 of SEQ ID NO: 28, or amino acids 16 to 243 of SEQ ID NO: 32 is 10, e.g., 1, 2, 3, 4, 5, 6, 8, 9, or 10.

Binding Domains

In one embodiment, the present invention also relates to cellulose binding domains having a sequence identity to amino acids 304 to 332 of SEQ ID NO: 10 or amino acids 282 to 337 of SEQ ID NO: 24 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; amino acids 291 to 319 of SEQ ID NO: 28 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%; or amino acids 274 to 301 of SEQ ID NO: 32 of at least 90%, e.g., at least 91%, at least 92%, at least 93%, at least 94%, at least 95%, at least 96%, at least 97%, at least 98%, at least 99%, or 100%. In one aspect, the cellulose binding domains comprise amino acid sequences that differ by up to 10 amino acids, e.g., 1, 2, 3, 4, 5, 6, 7, 8, 9, or 10, from amino acids 304 to 332 of SEQ ID NO: 10, amino acids 282 to 337 of SEQ ID NO: 24, amino acids 291 to 319 of SEQ ID NO: 28, or amino acids 274 to 301 of SEQ ID NO: 32.

The cellulose binding domain preferably comprises or consists of amino acids 304 to 332 of SEQ ID NO: 10, amino acids 282 to 337 of SEQ ID NO: 24, amino acids 291 to 319 of SEQ ID NO: 28, amino acids 274 to 301 of SEQ ID NO: 32, or an allelic variant thereof; or is a fragment thereof having cellulose binding activity.

In another embodiment, the present invention also relates to cellulose binding domains encoded by polynucleotides that hybridize under very low stringency conditions, low stringency conditions, medium stringency conditions, medium-high stringency conditions, high stringency conditions, or very high stringency conditions (as defined above) with (i) nucleotides 910 to 996 of SEQ ID NO: 9, nucleotides 904 to 1071 of SEQ ID NO: 23, nucleotides 951 to 1107 of SEQ ID NO: 27 or the cDNA sequence thereof, or nucleotides 1099 to 1182 of SEQ ID NO: 31, or (ii) the full-length complement of (i) (Sambrook et al., 1989, supra).

In another embodiment, the present invention also relates to cellulose binding domains encoded by polynucleotides having a sequence identity to nucleotides 910 to 996 of SEQ ID NO: 9 or nucleotides 904 to 1071 of SEQ ID NO: 23 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; nucleotides 951 to 1107 of SEQ ID NO: 27 or the cDNA sequence thereof of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%; or nucleotides 1099 to 1182 of SEQ ID NO: 31 of at least 90%, e.g., at least 91%, at least 92%, at least 93%, at least 94%, at least 95%, at least 96%, at least 97%, at least 98%, at least 99%, or 100%.

The polynucleotide encoding the cellulose binding domain preferably comprises or consists of nucleotides 910 to 996 of SEQ ID NO: 9, nucleotides 904 to 1071 of SEQ ID NO: 23, nucleotides 951 to 1107 of SEQ ID NO: 27 or the cDNA sequence thereof, or nucleotides 1099 to 1182 of SEQ ID NO: 31, or is the sequence contained in *Corynascus thermophilus* CBS 174.70.

In another embodiment, the present invention also relates to cellulose binding domain variants of amino acids 304 to 332 of SEQ ID NO: 10, amino acids 282 to 337 of SEQ ID NO: 24, amino acids 291 to 319 of SEQ ID NO: 28, or amino acids 274 to 301 of SEQ ID NO: 32 comprising a substitution, deletion, and/or insertion at one or more (e.g., several) positions. In one aspect, the number of amino acid substitutions, deletions and/or insertions introduced into the sequence of amino acids 304 to 332 of SEQ ID NO: 10, amino acids 282 to 337 of SEQ ID NO: 24, amino acids 291 to 319 of SEQ ID NO: 28, or amino acids 274 to 301 of SEQ ID NO: 32 is 10, e.g., 1, 2, 3, 4, 5, 6, 8, 9, or 10.

A catalytic domain operably linked to the cellulose binding domain may be from a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase. The polynucleotide encoding the catalytic domain may be obtained from any prokaryotic, eukaryotic, or other source.

Polynucleotides

The present invention also relates to isolated polynucleotides encoding a polypeptide, a catalytic domain, or cellulose binding domain of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al, 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Corynascus*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, or SEQ ID NO: 31, or the cDNA sequences thereof, by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci.*

USA 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al, 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding sequences for filamentous fungal host cells are the signal peptide coding sequences obtained from the genes for *Aspergillus niger* neutral amylase, *Aspergillus nigerglucoamylase, Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al, 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al, 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al, 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp. 182-187, Academic Press, Inc., New York; Ito et al, 1983, *J. Bacteriol* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally (b) recovering the polypeptide. In one aspect, the cell is a *Corynascus* cell. In another aspect, the cell is a *Corynascus thermophilus* cell. In another aspect, the cell is *Corynascus thermophilus* CBS 174.70.

The present invention also relates to methods of producing a polypeptide of the present invention, comprising (a) cultivating a recombinant host cell of the present invention under conditions conducive for production of the polypeptide; and optionally (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a whole fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or *tomato* (Kyozuka et al, 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al, 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al, 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and optionally (b) recovering the polypeptide or domain.

Removal or Reduction of Cellulolytic Enhancing Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may also be accomplished by insertion, substitution, or deletion of one or more nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

The present invention also relates to methods of inhibiting the expression of a polypeptide having cellulolytic enhancing activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA for inhibiting transcription. In another preferred aspect, the dsRNA is micro RNA for inhibiting translation.

The present invention also relates to such double-stranded RNA (dsRNA) molecules, comprising a portion of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, or SEQ ID NO: 31 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

The present invention further relates to a mutant cell of a parent cell that comprises a disruption or deletion of a polynucleotide encoding the polypeptide or a control sequence thereof or a silenced gene encoding the polypeptide, which results in the mutant cell producing less of the polypeptide or no polypeptide compared to the parent cell.

The polypeptide-deficient mutant cells are particularly useful as host cells for expression of native and heterologous polypeptides. Therefore, the present invention further relates to methods of producing a native or heterologous polypeptide, comprising (a) cultivating the mutant cell under conditions conducive for production of the polypeptide; and (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

The methods of the present invention for producing an essentially cellulolytic enhancing activity-free product are of particular interest in the production of eukaryotic polypeptides, in particular fungal proteins such as enzymes. The cellulolytic enhancing activity-deficient cells may also be used to express heterologous proteins of pharmaceutical interest such as hormones, growth factors, receptors, and the like. The term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from cellulolytic enhancing activity that is produced by a method of the present invention.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The fermentation broth formulations or cell compositions may further comprise multiple enzymatic activities, such as one or more (e.g., several) enzymes selected from the group consisting of a cellulase, a hemicellulase, an esterase, an expansin, a laccase, a ligninolytic enzyme, a pectinase, a peroxidase, a protease, and a swollenin. The fermentation broth formulations or cell compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of preferred uses of the compositions of the present invention. The dosage of the composition and other conditions under which the composition is used may be determined on the basis of methods known in the art.

Enzyme Compositions

The present invention also relates to compositions comprising a polypeptide of the present invention. Preferably, the compositions are enriched in such a polypeptide. The term "enriched" indicates that the cellulolytic enhancing activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of a cellulase, a hemicellulase, an esterase, an expansin, a laccase, a ligninolytic enzyme, a pectinase, a peroxidase, a protease, and a swollenin. The compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase. The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Uses

The present invention is also directed to the following processes for using the polypeptides having cellulolytic enhancing activity, or compositions thereof.

The present invention also relates to processes for degrading a cellulosic material, comprising: treating the cellulosic material with an enzyme composition in the presence of a polypeptide having cellulolytic enhancing activity of the present invention. In one aspect, the processes further comprise recovering the degraded or converted cellulosic material. Soluble products of degradation or conversion of the cellulosic material can be separated from insoluble cellulosic material using a method known in the art such as, for example, centrifugation, filtration, or gravity settling.

The present invention also relates to processes of producing a fermentation product, comprising: (a) saccharifying a cellulosic material with an enzyme composition in the presence of a polypeptide having cellulolytic enhancing activity of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a polypeptide having cellulolytic enhancing activity of the present invention. In one aspect, the fermenting of the cellulosic material produces a fermentation product. In another aspect, the processes further comprise recovering the fermentation product from the fermentation.

The processes of the present invention can be used to saccharify the cellulosic material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material typically involves pretreatment, enzymatic hydrolysis (saccharification), and fermentation.

The processing of the cellulosic material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic material (Chandra et al, 2007, Substrate pretreatment: The key to effective enzymatic hydrolysis of lignocellulosics?, *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al, 2006, *Appl. Biochem. Biotechnol.* 129-132: 496-508; Varga et al., 2004, *Appl. Biochem. Biotechnol.* 113-116: 509-523; Sassner et al, 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al, 2004, *Bioresource Technol.* 91: 179-188; Lee et al, 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al, 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al, 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al, 2002, *Appl. Biochem. Biotechnol.* 98: 23-35; Chundawat et al, 2007, *Biotechnol. Bioeng.* 96: 219-231; Alizadeh et al, 2005, *Appl. Biochem. Biotechnol.* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al, 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol. Vol.* 105-108, p. 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt %, e.g., 20-70 wt % or 30-60 wt %, such as around 40 wt %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition as described herein in the presence of a polypeptide having cellulolytic enhancing activity of the present invention. The enzyme components of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme components, i.e., optimal for the enzyme components. The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

The enzyme compositions can comprise any protein useful in degrading the cellulosic material.

In one aspect, the enzyme composition comprises or further comprises one or more (e.g., several) proteins selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin.

In the processes of the present invention, the enzyme(s) can be added prior to or during saccharification, saccharification and fermentation, or fermentation.

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and a polypeptide having cellulolytic enhancing activity depend on several factors including, but not limited to, the mixture of cellulolytic and/or hemicellulolytic enzyme components, the cellulosic material, the concentration of cellulosic material, the pretreatment(s) of the cellulosic material, temperature, time, pH, and inclusion of fermenting organism (e.g., yeast for Simultaneous Saccharification and Fermentation).

In one aspect, an effective amount of cellulolytic or hemicellulolytic enzyme to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In another aspect, an effective amount of a polypeptide having cellulolytic enhancing activity to the cellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material.

In another aspect, an effective amount of a polypeptide having cellulolytic enhancing activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a Gram positive bacterial polypeptide such as a *Bacillus*, *Streptococcus*, *Streptomyces*, *Staphylococcus*, *Enterococcus*, *Lactobacillus*, *Lactococcus*, *Clostridium*, *Geobacillus*, *Caldicellulosiruptor*, *Acidothermus*, *Thermobifidia*, or *Oceanobacillus* polypeptide having enzyme activity, or a Gram negative bacterial polypeptide such as an *E. coli*, *Pseudomonas*, *Salmonella*, *Campylobacter*, *Helicobacter*, *Flavobacterium*, *Fusobacterium*, *Ilyobacter*, *Neisseria*, or *Ureaplasma* polypeptide having enzyme activity.

In one aspect, the polypeptide is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* polypeptide having enzyme activity.

In another aspect, the polypeptide is a *Streptococcus equisimilis*, *Streptococcus pyogenes*, *Streptococcus uberis*, or *Streptococcus equi* subsp. *Zooepidemicus* polypeptide having enzyme activity.

In another aspect, the polypeptide is a *Streptomyces achromogenes*, *Streptomyces avermitilis*, *Streptomyces coelicolor*, *Streptomyces griseus*, or *Streptomyces lividans* polypeptide having enzyme activity.

The polypeptide having enzyme activity may also be a fungal polypeptide, and more preferably a yeast polypeptide such as a *Candida*, *Kluyveromyces*, *Pichia*, *Saccharomyces*, *Schizosaccharomyces*, or *Yarrowia* polypeptide having enzyme activity; or more preferably a filamentous fungal polypeptide such as an *Acremonium*, *Agaricus*, *Alternaria*, *Aspergillus*, *Aureobasidium*, *Botryosphaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* polypeptide having enzyme activity.

In one aspect, the polypeptide is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* polypeptide having enzyme activity.

In another aspect, the polypeptide is an *Acremonium cellulolyticus*, *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Chrysosporium keratinophilum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium funiculosum*, *Penicillium purpurogenum*, *Phanerochaete chrysosporium*, *Thielavia achro-*

*matica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride,* or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLIC® CTec3 (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), FILTRASE® NL (DSM); METHAPLUS® S/L 100 (DSM), ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt % of solids, e.g., about 0.025 to about 4.0 wt % of solids or about 0.005 to about 2.0 wt % of solids.

Examples of bacterial endoglucanases that can be used in the processes of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, *Gene* 45: 253-263, *Trichoderma reesei* Cel7B endoglucanase I (GENBANK™ accession no. M15665), *Trichoderma reesei* endoglucanase II (Saloheimo, et al., 1988, Gene 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii* endoglucanase (Sakamoto et al., 1995, Current Genetics 27: 435-439), *Erwinia carotovara* endoglucanase (Saarilahti et al., 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), *Melanocarpus albomyces* endoglucanase (GENBANK™ accession no. MAL515703), *Neurospora crassa* endoglucanase (GENBANK™ accession no. XM_324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, *Cladorrhinum foecundissimum* ATCC 62373 CEL7A endoglucanase, and *Trichoderma reesei* strain No. VTT-D-80133 endoglucanase (GENBANK™ accession no. M15665).

Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al, 2000, *J. Biol. Chem.* 275: 4973-4980), *Aspergillus oryzae* (WO 2002/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637.

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 5,457,046, 5,648,263, and 5,686,593.

In one aspect, the GH61 polypeptide having cellulolytic enhancing activity is used in the presence of a soluble activating divalent metal cation according to WO 2008/151043, e.g., manganese or copper.

In another aspect, the GH61 polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of the bicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothienopyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl)furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of the nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), CELLIC® HTec3 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt accession number Q7SOW4), *Trichoderma reesei* (UniProtKB/TrEMBL accession number Q92458), and *Talaromyces emersonii* (SwissProt accession number Q8X212).

Examples of acetylxylan esterases useful in the processes of the present invention include, but are not limited to, acetylxylan esterases from *Aspergillus aculeatus* (WO 2010/108918), *Chaetomium globosum* (Uniprot accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria nodorum* (Uniprot accession number QOUHJI), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt Accession number Al D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt accession number alcc12), *Aspergillus fumigatus* (SwissProt accession number Q4WW45), *Aspergillus niger* (Uniprot accession number Q96WX9), *Aspergillus terreus* (SwissProt accession number QOCJP9), *Humicola insolens* (WO 2010/014706), *Penicillium aurantiogriseum* (WO 2009/068565), *Talaromyces emersonii* (UniProt accession number Q8X211), and *Trichoderma reesei* (Uniprot accession number Q99024).

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al, 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida, Kluyveromyces*, and *Saccharomyces*, e.g., *Candida sonorensis, Kluyveromyces marxianus*, and *Saccharomyces cerevisiae*.

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans; Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae; Clostridium*, such as *C. acetobutylicum, C. thermocellum*, and *C. phytofermentans; E. coli*, especially *E. coli* strains that have been genetically modified to improve the yield of ethanol; *Geobacillus* sp.; *Hansenula*, such as *Hansenula anomala; Klebsiella*, such as *K. oxytoca; Kluyveromyces*, such as *K. marxianus, K. lactis, K. thermotolerans*, and *K. fragilis; Schizosaccharomyces*, such as *S. pombe; Thermoanaerobacter*, such as *Thermoanaerobacter saccharolyticum*; and *Zymomonas*, such as *Zymomonas mobilis*.

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida blankii*. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida scehatae*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In another more preferred aspect, the yeast is *Saccharomyces cerevisiae*. In another more preferred aspect, the yeast is *Saccharomyces distaticus*. In another more preferred aspect, the yeast is *Saccharomyces uvarum*.

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacillus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae, Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae, Appl. Microbiol Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli, Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis, Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately 105 to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al, Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another more preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Signal Peptides

The present invention also relates to an isolated polynucleotide encoding a signal peptide comprising or consisting of amino acids 1 to 23 of SEQ ID NO: 2, amino acids 1 to 20 of SEQ ID NO: 4, amino acids 1 to 20 of SEQ ID NO: 6, amino acids 1 to 15 of SEQ ID NO: 8, amino acids 1 to 19 of SEQ ID NO: 10, amino acids 1 to 16 of SEQ ID NO: 12, amino acids 1 to 17 of SEQ ID NO: 14, amino acids 1 to 17 of SEQ ID NO: 16, amino acids 1 to 15 of SEQ ID NO: 18, amino acids 1 to 17 of SEQ ID NO: 20, amino acids 1 to 21 of SEQ ID NO: 22, amino acids 1 to 20 of SEQ ID NO: 24, amino acids 1 to 17 of SEQ ID NO: 26, amino acids 1 to 18 of SEQ ID NO: 28, amino acids 1 to 20 of SEQ ID NO: 30, or amino acids 1 to 15 of SEQ ID NO: 32. The polynucleotide may further comprise a gene encoding a protein, which is operably linked to the signal peptide. The protein is preferably foreign to the signal peptide. In one aspect, the polynucleotide encoding the signal peptide is nucleotides 1 to 69 of SEQ ID NO: 1. In another aspect, the polynucleotide encoding the signal peptide is nucleotides 1 to 60 of SEQ ID NO: 3. In another aspect, the polynucleotide encoding the signal peptide is nucleotides 1 to 60 of SEQ ID NO: 5. In another aspect, the polynucleotide encoding the signal peptide is nucleotides 1 to 45 of SEQ ID NO: 7. In another aspect, the polynucleotide encoding the signal peptide is nucleotides 1 to 57 of SEQ ID NO: 9. In another aspect, the polynucleotide encoding the signal peptide is nucleotides 1 to 48 of SEQ ID NO: 11. In another aspect, the polynucleotide encoding the signal peptide is nucleotides 1 to 51 of SEQ ID NO: 13. In another aspect, the polynucleotide encoding the signal peptide is nucleotides 1 to 51 of SEQ ID NO: 15. In another aspect, the polynucleotide encoding the signal peptide is nucleotides 1 to 45 of SEQ ID NO: 17. In another aspect, the polynucleotide encoding the signal peptide is nucleotides 1 to 51 of SEQ ID NO: 19. In another aspect, the polynucleotide encoding the signal peptide is nucleotides 1 to 63 of SEQ ID NO: 21. In another aspect, the polynucleotide encoding the signal peptide is nucleotides 1 to 60 of SEQ ID NO: 23. In another aspect, the polynucleotide encoding the signal peptide is nucleotides 1 to 51 of SEQ ID NO: 25. In another aspect, the polynucleotide encoding the signal peptide is nucleotides 1 to 54 of SEQ ID NO: 27. In another aspect, the polynucleotide encoding the signal peptide is nucleotides 1 to 60 of SEQ ID NO: 29. In another aspect, the polynucleotide encoding the signal peptide is nucleotides 1 to 45 of SEQ ID NO: 31.

The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and optionally (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The gene may be obtained from any prokaryotic, eukaryotic, or other source.

The present invention is further described by the following examples that should not be construed as limiting the scope of the invention.

EXAMPLES

Strain

*Corynascus thermophilus* CBS 174.70 (synonym *Myceliophthora fergusii*) was used as the source of the GH61 polypeptide coding sequences.

Media

PDA plates were composed of 39 grams of potato dextrose agar and deionized water to 1 liter.

YPG medium was composed of 0.4% of yeast extract, 0.1% of $KH_2PO_4$, 0.05% of $MgSO_4.7H_2O$, and 1.5% glucose in deionized water.

YPM medium was composed of 1% of yeast extract, 2% of peptone, and 2% of maltose in deionized water.

Selection plates were composed of 342 g of sucrose, 20 ml of salt solution, 20 g of agar, and deionized water to 1 liter. The salt solution was composed of 2.6% KCl, 2.6% $MgSO_4.7H2O$, 7.6% $KH_2PO_4$, 2 ppm $Na_2B_4O_7.10H_2O$, 20 ppm $CuSO_4.5H_2O$, 40 ppm $FeSO_4.7H_2O$, 40 ppm $MnSO_4.2H_2O$, 40 ppm $Na_2MoO_4.2H_2O$, and 400 ppm $ZnSO_4.7H_2O$.

Example 1: *Corynascus thermophilus* Genomic DNA Extraction

*Corynascus thermophilus* CBS 174.70 was inoculated onto a PDA plate and incubated for 3 days at 45° C. in the darkness. Several mycelia-PDA plugs were inoculated into 500 ml shake flasks containing 100 ml of YPG medium. The flasks were incubated for 4 days at 45° C. with shaking at 160 rpm. The mycelia were collected by filtration through MIRACLOTH® (Calbiochem, La Jolla, Calif., USA) and frozen in liquid nitrogen. Frozen mycelia were ground, by a mortar and a pestle, to a fine powder, and genomic DNA was isolated using a DNEASY® Plant Maxi Kit (QIAGEN Inc., Valencia, Calif., USA).

Example 2: Genome Sequencing, Assembly and Annotation

The extracted genomic DNA was delivered to Beijing Genome Institute (BGI, Shenzhen, China) for genome sequencing using an ILLUMINA® GA2 System (Illumina, Inc., San Diego, Calif., USA). The raw reads were assembled at BGI using program SOAPdenovo (Li et al., 2010, *Genome Research* 20(2): 265-72). The assembled sequences were analyzed using standard bioinformatics methods for gene finding and functional prediction. Briefly, geneID (Parra et al., 2000, *Genome Research* 10(4): 511-515) was used for gene prediction. Blastall version 2.2.10 (Altschul et al., 1990, *J. Mol. Biol.* 215 (3): 403-410; National Center for Biotechnology Information (NCBI), Bethesda, Md., USA) and HMMER version 2.1.1 (National Center for Biotechnology Information (NCBI), Bethesda, Md., USA) were used to predict function based on structural homology. The GH61 polypeptides were identified directly by analysis of the Blast results. The Agene program (Munch and Krogh, 2006, *BMC Bioinformatics* 7: 263) and SignalP program (Nielsen et al., 1997, *Protein Engineering* 10: 1-6) were used to identify starting codons. The SignalP program was further used to predict the signal peptides. Pepstats (Rice et al., 2000, *Trends Genet.* 16(6): 276-277) was used to predict the isoelectric points and molecular weights of the deduced amino acid sequences.

Example 3: Cloning of the *Corynascus thermophilus* GH61 Coding Sequences from Genomic DNA Sixteen GH61 polypeptide coding sequences were selected as shown in Table 1 for expression cloning.

TABLE 1

| GH61 coding sequences | | | |
|---|---|---|---|
| Working name | Gene name | DNA sequence | Protein sequence |
| GH61_Mf4023 | Seq8 | SEQ ID NO: 1 | SEQ ID NO: 2 |
| GH61_Mf3054 | Seq9 | SEQ ID NO: 3 | SEQ ID NO: 4 |
| GH61_Mf5285 | Seq10 | SEQ ID NO: 5 | SEQ ID NO: 6 |
| GH61_Mf2129 | Seq11 | SEQ ID NO: 7 | SEQ ID NO: 8 |
| GH61_Mf3200 | Seq25 | SEQ ID NO: 9 | SEQ ID NO: 10 |
| GH61_Mf4155 | Seq13 | SEQ ID NO: 11 | SEQ ID NO: 12 |
| GH61_Mf3225 | Seq15 | SEQ ID NO: 13 | SEQ ID NO: 14 |
| GH61_Mf7296 | Seq16 | SEQ ID NO: 15 | SEQ ID NO: 16 |
| GH61_Mf3002 | Seq17 | SEQ ID NO: 17 | SEQ ID NO: 18 |
| GH61_Mf2415 | Seq18 | SEQ ID NO: 19 | SEQ ID NO: 20 |
| GH61_Mf1314 | Seq19 | SEQ ID NO: 21 | SEQ ID NO: 22 |
| GH61_Mf0062 | Seq20 | SEQ ID NO: 23 | SEQ ID NO: 24 |
| GH61_Mf4718 | Seq21 | SEQ ID NO: 25 | SEQ ID NO: 26 |
| GH61_Mf3928 | Seq22 | SEQ ID NO: 27 | SEQ ID NO: 28 |
| GH61_Mf5739 | Seq23 | SEQ ID NO: 29 | SEQ ID NO: 30 |
| GH61_Mf3001 | Seq24 | SEQ ID NO: 31 | SEQ ID NO: 32 |

Based on the DNA information obtained from genome sequencing, oligonucleotide primers, shown below, were designed to amplify the coding sequences of the GH61 polypeptides from the genomic DNA of *Corynascus thermophilus* CBS 174.70. The primers were synthesized by Invitrogen Beijing, China.

Seq8 forward:
(SEQ ID NO: 33)
ACACAACTGGGGATCCACCatgccccctccacggcta

Seq8 reverse:
(SEQ ID NO: 34)
GTCACCCTCTAGATCTgcaagtacccaggtaaggagcagtg

Seq9 forward:
(SEQ ID NO: 35)
ACACAACTGGGGATCCACCatggctccattaacgtccgca

Seq9 reverse:
(SEQ ID NO: 36)
GTCACCCTCTAGATCTctccacgatgtcgccgttc

Seq10 forward:
(SEQ ID NO: 37)
ACACAACTGGGGATCCACCatgaaatacgccctccagctcg

-continued

Seq10 reverse:
(SEQ ID NO: 38)
GTCACCCTCTAGATCTcatccattctgtcgaaaatcccttg

Seq11 forward:
(SEQ ID NO: 39)
ACACAACTGGGGATCCACCatgaaggccctctctctccttgc

Seq11 reverse:
(SEQ ID NO: 40)
GTCACCCTCTAGATCTactgcgctcaaacgaccaagtc

Seq13 forward:
(SEQ ID NO: 41)
ACACAACTGGGGATCCACCatgaaaacgcttgccgcc

Seq13 reverse:
(SEQ ID NO: 42)
GTCACCCTCTAGATCTcaaatagacggcttcccccttctg

Seq15 forward:
(SEQ ID NO: 43)
ACACAACTGGGGATCCACC atgtaccgcacgctcgg

Seq15 reverse:
(SEQ ID NO: 44)
GTCACCCTCTAGATCTcgttgcccaatagcttgtcaaac

Seq16 forward:
(SEQ ID NO: 45)
ACACAACTGGGGATCCACCatgctggcgacaaccttcg

Seq16 reverse:
(SEQ ID NO: 46)
GTCACCCTCTAGATCTcgaccacctcaacttgtggtg

Seq17 forward:
(SEQ ID NO: 47)
ACACAACTGGGGATCCACCatgaaggttctcgcgccc

Seq17 reverse:
(SEQ ID NO: 48)
GTCACCCTCTAGATCTagagagagagataccgcgacgatgag

Seq18 forward:
(SEQ ID NO: 49)
ACACAACTGGGGATCCACCatgaagctgagcgctgc

Seq18 reverse:
(SEQ ID NO: 50)
GTCACCCTCTAGATCTttgtcgcttctcggctcg

Seq19 forward:
(SEQ ID NO: 51)
ACACAACTGGGGATCCACCatgtcttccttcacctccaaggg

Seq19 reverse:
(SEQ ID NO: 52)
GTCACCCTCTAGATCTgtgaacgatatctacgaataactcggttg

Seq20 forward:
(SEQ ID NO: 53)
ACACAACTGGGGATCCACC atgcatcctccatctttgttcttg

Seq20 reverse:
(SEQ ID NO: 54)
GTCACCCTCTAGATCTatcagccaaaacacccgtcctag

Seq21 forward:
(SEQ ID NO: 55)
ACACAACTGGGGATCCACC atgaagctctctctcttttccgtc

Seq21 reverse:
(SEQ ID NO: 56)
GTCACCCTCTAGATCTactcggaaaggtcggcctagac

Seq22 forward:
(SEQ ID NO: 57)
ACACAACTGGGGATCCACCatgaagtccttcaccctcac

Seq22 reverse:
(SEQ ID NO: 58)
GTCACCCTCTAGATCTagaaagtgccctggctagggac

Seq23 forward:
(SEQ ID NO: 59)
ACACAACTGGGGATCCACCatgaagtcgttcacctcagccttg

Seq23 reverse:
(SEQ ID NO: 60)
GTCACCCTCTAGATCTgggtctggttccagcgacaa

Seq24 forward
(SEQ ID NO: 61)
ACACAACTGGGGATCCACCatgaaggcctttagcctcgtc

Seq24 reverse
(SEQ ID NO: 62)
GTCACCCTCTAGATCTcctctctcggctcgggag

Seq25 forward
(SEQ ID NO: 63)
ACACAACTGGGGATCCACCatggccaagacctctgctctcc

Seq25 reverse
(SEQ ID NO: 64)
GTCACCCTCTAGATCTcgctcaccgacttggcattc

Lowercase characters represent the coding regions of the genes, while capitalized characters represent regions homologous to the insertion sites of plasmid pPFJO355 (WO 2011/005867).

Example 4: Characterization of the Genomic DNAs Encoding GH61 Polypeptides

The genomic DNA sequence and deduced amino acid sequence of a *Corynascus thermophilus* GH61 polypeptide coding sequence are shown in SEQ ID NO: 1 (D1321N) and SEQ ID NO: 2 (P24MRR), respectively. The coding sequence is 975 bp including the stop codon without any introns. The encoded predicted protein is 324 amino acids. Using the SignalP program (Nielsen et al., 1997, supra), a signal peptide of 23 residues was predicted. The predicted mature protein contains 301 amino acids with a predicted molecular mass of 31.95 kDa and a predicted isoelectric point of 5.44.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Corynascus thermophilus* genomic DNA encoding a GH61 polypeptide shares 54.5% identity (excluding gaps) to the deduced amino acid sequence of a GH61 polypeptide from *Thielavia terrestris* (GENESEQP AZI47998).

The genomic DNA sequence and deduced amino acid sequence of another *Corynascus thermophilus* GH61 polypeptide coding sequence are shown in SEQ ID NO: 3 and SEQ ID NO: 4, respectively. The coding sequence is 1115 bp including the stop codon, which is interrupted by 4 introns of 80 bp (nucleotides 213 to 292), 93 bp (nucleotides 356 to 448), 102 bp (nucleotides 500 to 601), and 118 bp (nucleotides 948 to 1065). The encoded predicted protein is 240 amino acids. Using the SignalP program (Nielsen et al., 1997, supra), a signal peptide of 20 residues was predicted. The predicted mature protein contains 220 amino acids with a predicted molecular mass of 23.61 kDa and a predicted isoelectric point of 5.62.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Corynascus thermophilus* genomic DNA encoding a GH61 polypeptide shares 76.6% identity (excluding gaps) to the deduced amino acid sequence of a GH61 polypeptide from *Chaetomium globosum* (GENESEQP AZJ 19523).

The genomic DNA sequence and deduced amino acid sequence of another *Corynascus thermophilus* GH61 polypeptide coding sequence are shown in SEQ ID NO: 5 (D1317F) and SEQ ID NO: 6 (P24MDK), respectively. The coding sequence is 988 bp including the stop codon, which is interrupted by four introns of 120 bp (nucleotides 408 to 527), 65 bp (nucleotides 626 to 690), 65 bp (nucleotides 805 to 869), and 59 bp (nucleotides 918 to 976). The encoded predicted protein is 225 amino acids. Using the SignalP program (Nielsen et al., 1997, supra), a signal peptide of 20 residues was predicted. The predicted mature protein contains 205 amino acids with a predicted molecular mass of 22.36 kDa and a predicted isoelectric point of 5.41.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Corynascus thermophilus* genomic DNA encoding a GH61 polypeptide shares 83.1% identity (excluding gaps) to the deduced amino acid sequence of a GH61 polypeptide from *Myceliophthora thermophila* (GENESEQP AWI36170).

The genomic DNA sequence and deduced amino acid sequence of another *Corynascus thermophilus* GH61 polypeptide coding sequence are shown in SEQ ID NO: 7 (D1317G) and SEQ ID NO: 8 (P24MDM), respectively. The coding sequence is 859 bp including the stop codon, which is interrupted by two introns of 86 bp (nucleotides 441 to 526) and 65 bp (nucleotides 624 to 688). The encoded predicted protein is 235 amino acids. Using the SignalP program (Nielsen et al., 1997, supra), a signal peptide of 15 residues was predicted. The predicted mature protein contains 220 amino acids with a predicted molecular mass of 23.09 kDa and a predicted isoelectric point of 4.51.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Corynascus thermophilus* genomic DNA encoding a GH61 polypeptide shares 85.5% identity (excluding gaps) to the deduced amino acid sequence of a GH61 polypeptide from *Myceliophthora thermophila* (GENESEQP AZI47970).

The genomic DNA sequence and deduced amino acid sequence of another *Corynascus thermophilus* GH61 polypeptide coding sequence are shown in SEQ ID NO: 9 (D1321V) and SEQ ID NO: 10 (P24MRY), respectively. The coding sequence is 1011 bp including the stop codon without any introns. The encoded predicted protein is 336 amino acids. Using the SignalP program (Nielsen et al., 1997, supra), a signal peptide of 19 residues was predicted. The predicted mature protein contains 317 amino acids with a predicted molecular mass of 32.95 kDa and a predicted isoelectric point of 6.04. The GH61 catalytic domain and CBM domain were predicted to be amino acids 20 to 251 and amino acids 304 to 332, respectively, by aligning the amino acid sequence using BLAST to all CAZY-defined subfamily modules (Cantarel et al., 2009, *Nucleic Acids Res.* 37: D233-238), where the single most significant alignment within a subfamily was used to predict the GH61 domain and CBM domain.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Corynascus thermophilus* genomic DNA encoding a GH61 polypeptide shares 78.9% identity (excluding gaps) to the deduced amino acid sequence of a GH61 polypeptide from *Myceliophthora thermophila* (GENESEQP AWI36182).

The genomic DNA sequence and deduced amino acid sequence of another *Corynascus thermophilus* GH61 polypeptide coding sequence are shown in SEQ ID NO: 11 (D1321Q) and SEQ ID NO: 12 (P24MRT), respectively. The coding sequence is 1315 bp including the stop codon, which is interrupted by 5 introns of 73 bp (nucleotides 94 to 166), 187 bp (nucleotides 245 to 431), 96 bp (nucleotides 665 to 760), 91 bp (nucleotides 822 to 912), and 106 bp (nucleotides 1166 to 1271). The encoded predicted protein is 253 amino acids. Using the SignalP program (Nielsen et al., 1997, supra), a signal peptide of 16 residues was predicted. The predicted mature protein contains 237 amino acids with a predicted molecular mass of 25.39 kDa and a predicted isoelectric point of 7.17.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Corynascus thermophilus* genomic DNA encoding a GH61 polypeptide shares 73.1% identity (excluding gaps) to the deduced amino acid sequence of a GH61 polypeptide from *Myceliophthora thermophila* (GENESEQP AWI36236).

The genomic DNA sequence and deduced amino acid sequence of another *Corynascus thermophilus* GH61 polypeptide coding sequence are shown in SEQ ID NO: 13 (D1317K) and SEQ ID NO: 14 (P24MDQ), respectively. The coding sequence is 924 bp including the stop codon, which is interrupted by 2 introns of 87 bp (nucleotides 99 to 185) and 69 bp (nucleotides 754 to 822). The encoded predicted protein is 255 amino acids. Using the SignalP program (Nielsen et al, 1997, supra), a signal peptide of 17 residues was predicted. The predicted mature protein contains 238 amino acids with a predicted molecular mass of 25.58 kDa and a predicted isoelectric point of 5.13.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Corynascus thermophilus* genomic DNA encoding a GH61 polypeptide shares 86.3% identity (excluding gaps) to the deduced amino acid sequence of a GH61 polypeptide from *Myceliophthora thermophila* (GENESEQP AWI36176).

The genomic DNA sequence and deduced amino acid sequence of another *Corynascus thermophilus* GH61 polypeptide coding sequence are shown in SEQ ID NO: 15 (D1317M) and SEQ ID NO: 16 (P24MDR), respectively. The coding sequence is 742 bp including the stop codon, which is interrupted by one intron of 64 bp (nucleotides 395 to 458). The encoded predicted protein is 225 amino acids. Using the SignalP program (Nielsen et al., 1997, *Protein Engineering* 10: 1-6), a signal peptide of 17 residues was predicted. The predicted mature protein contains 208 amino acids with a predicted molecular mass of 22.58 kDa and a predicted isoelectric point of 7.84.

A comparative pairwise global alignment of amino acid sequences was determined using the Needleman and Wunsch algorithm (Needleman and Wunsch, 1970, *J. Mol. Biol.* 48: 443-453) with gap open penalty of 10, gap extension penalty of 0.5, and the EBLOSUM62 matrix. The alignment showed that the deduced amino acid sequence of the *Corynascus thermophilus* genomic DNA encoding a GH61 polypeptide shares 80.4% identity (excluding gaps) to the deduced amino acid sequence of a GH61 polypeptide from *Myceliophthora thermophila* (GENESEQP AWI36197).

The genomic DNA sequence and deduced amino acid sequence of another *Corynascus thermophilus* GH61 polypeptide coding sequence are shown in SEQ ID NO: 17 (D137US) and SEQ ID NO: 18 (P24QE1), respectively. The coding sequence is 901 bp including the stop codon, which is interrupted by 2 introns of 91 bp (nucleotides 569 to 659) and 96 bp (nucleotides 719 to 814). The encoded predicted protein is 237 amino acids. Using the SignalP program (Nielsen et al., 1997, supra), a signal peptide of 15 residues was predicted. The predicted mature protein contains 222 amino acids with a predicted molecular mass of 23.40 kDa and a predicted isoelectric point of 6.56.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Corynascus thermophilus* genomic DNA encoding a GH61 polypeptide shares 86.5% identity (excluding gaps) to the deduced amino acid sequence of a GH61 polypeptide from *Myceliophthora thermophila* (GENESEQP AWI36179).

The genomic DNA sequence and deduced amino acid sequence of another *Corynascus thermophilus* GH61 polypeptide coding sequence are shown in SEQ ID NO: 19 (D1317P) and SEQ ID NO: 20 (P24MDS), respectively. The coding sequence is 944 bp including the stop codon, which is interrupted by three introns of 86 bp (nucleotides 56 to 141), 71 bp (nucleotides 484 to 554), and 103 bp (nucleotides 693 to 795). The encoded predicted protein is 227 amino acids. Using the SignalP program (Nielsen et al., 1997, supra), a signal peptide of 17 residues was predicted. The predicted mature protein contains 210 amino acids with a predicted molecular mass of 22.84 kDa and a predicted isoelectric point of 8.35.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Corynascus thermophilus* genomic DNA encoding a GH61 polypeptide shares 87.2% identity (excluding gaps) to the deduced amino acid sequence of a GH61 polypeptide from *Myceliophthora thermophila* (GENESEQP AWI36200).

The genomic DNA sequence and deduced amino acid sequence of another *Corynascus thermophilus* GH61 polypeptide coding sequence are shown in SEQ ID NO: 21 (D1321R) and SEQ ID NO: 22 (P24GU3), respectively. The coding sequence is 948 bp including the stop codon without any introns. The encoded predicted protein is 315 amino acids. Using the SignalP program (Nielsen et al., 1997, supra), a signal peptide of 21 residues was predicted. The predicted mature protein contains 294 amino acids with a predicted molecular mass of 30.67 kDa and a predicted isoelectric point of 6.37.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Corynascus thermophilus* genomic DNA encoding a GH61 polypeptide shares 74.4% identity (excluding gaps) to the deduced amino acid sequence of a GH61 polypeptide from *Myceliophthora thermophila* (GENESEQP AWI36194).

The genomic DNA sequence and deduced amino acid sequence of another *Corynascus thermophilus* GH61 polypeptide coding sequence are shown in SEQ ID NO: 23 (D1317Q) and SEQ ID NO: 24 (P24MDT), respectively. The coding sequence is 1380 bp including the stop codon, which is interrupted by one intron of 60 bp (nucleotides 194 to 253). The encoded predicted protein is 439 amino acids. Using the SignalP program (Nielsen et al., 1997, supra), a signal peptide of 20 residues was predicted. The predicted mature protein contains 419 amino acids with a predicted molecular mass of 44.97 kDa and a predicted isoelectric point of 5.03. The GH61 catalytic domain and CBM domain were predicted to be amino acids 21 to 244 and amino acids 282 to 337, respectively, by aligning the amino acid sequence using BLAST to all CAZY-defined subfamily modules (Cantarel et al, 2009, supra), where the single most significant alignment within a subfamily was used to predict the GH61 domain and CBM domain.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Corynascus thermophilus* genomic DNA encoding a GH61 polypeptide shares 77.7% identity (excluding gaps) to the deduced amino acid sequence of a GH61 polypeptide from *Myceliophthora thermophila* (GENESEQP AWI36239).

The genomic DNA sequence and deduced amino acid sequence of another *Corynascus thermophilus* GH61 polypeptide coding sequence are shown in SEQ ID NO: 25 (D1317R) and SEQ ID NO: 26 (P24MDU), respectively. The coding sequence is 821 bp including the stop codon, which is interrupted by one intron of 80 bp (nucleotides 372 to 451). The encoded predicted protein is 246 amino acids. Using the SignalP program (Nielsen et al., 1997, supra), a signal peptide of 17 residues was predicted. The predicted mature protein contains 229 amino acids with a predicted molecular mass of 24.12 kDa and a predicted isoelectric point of 4.93.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Corynascus thermophilus* genomic DNA encoding a GH61 polypeptide shares 85% identity (excluding gaps) to the deduced amino acid sequence of a GH61 polypeptide from *Myceliophthora thermophila* (GENESEQP AZI47976).

The genomic DNA sequence and deduced amino acid sequence of another *Corynascus thermophilus* GH61 polypeptide coding sequence are shown in SEQ ID NO: 27 (D137UU) and SEQ ID NO: 28 (P24QE3), respectively. The coding sequence is 1125 bp including the stop codon, which is interrupted by 2 introns of 80 bp (nucleotides 244 to 323) and 70 bp (nucleotides 1002 to 1071). The encoded predicted protein is 324 amino acids. Using the SignalP program (Nielsen et al., 1997, supra), a signal peptide of 18 residues was predicted. The predicted mature protein contains 306 amino acids with a predicted molecular mass of 30.70 kDa and a predicted isoelectric point of 5.62. The GH61 catalytic domain and CBM domain were predicted to be amino acids 19 to 241 and amino acids 291 to 319, respectively, by aligning the amino acid sequence using BLAST to all CAZY-defined subfamily modules (Cantarel et al., 2009, supra), where the single most significant alignment within a subfamily was used to predict the GH61 domain and CBM domain.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Corynascus thermophilus* genomic DNA encoding a GH61 polypeptide shares 81.2% identity (excluding gaps) to the deduced amino acid sequence of a GH61 polypeptide from *Myceliophthora thermophila* (GENESEQP AWI36191).

The genomic DNA sequence and deduced amino acid sequence of another *Corynascus thermophilus* GH61 polypeptide coding sequence are shown in SEQ ID NO: 29 (D1321T) and SEQ ID NO: 30 (P24MRW), respectively. The coding sequence is 1037 bp including the stop codon, which is interrupted by three introns of 83 bp (nucleotides 127 to 209), 89 bp (nucleotides 304 to 392), and 136 bp (nucleotides 737 to 872). The encoded predicted protein is 242 amino acids. Using the SignalP program (Nielsen et al., 1997, supra), a signal peptide of 20 residues was predicted. The predicted mature protein contains 222 amino acids with a predicted molecular mass of 23.62 kDa and a predicted isoelectric point of 4.46.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Corynascus thermophilus* genomic DNA encoding a GH61 polypeptide shares 86.4% identity (excluding gaps) to the deduced amino acid sequence of a GH61 polypeptide from *Myceliophthora thermophila* (GENESEQP AWI36173).

The genomic DNA sequence and deduced amino acid sequence of another *Corynascus thermophilus* GH61 polypeptide coding sequence are shown in SEQ ID NO: 31 (D1321U) and SEQ ID NO: 32 (P24MRX), respectively. The coding sequence is 1200 bp including the stop codon, which is interrupted by 2 introns of 83 bp (nucleotides 302 to 384) and 196 bp (nucleotides 652 to 847). The encoded predicted protein is 306 amino acids. Using the SignalP program (Nielsen et al., 1997, supra), a signal peptide of 15 residues was predicted. The predicted mature protein contains 291 amino acids with a predicted molecular mass of 30.08 kDa and a predicted isoelectric point of 5.82. The GH61 catalytic domain and CBM domain were predicted to be amino acids 16 to 243 and amino acids 274 to 301, respectively, by aligning the amino acid sequence using BLAST to all CAZY-defined subfamily modules (Cantarel et al., 2009, supra), where the single most significant alignment within a subfamily was used to predict the GH61 domain and CBM domain.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Corynascus thermophilus* genomic DNA encoding a GH61 polypeptide shares 85.2% identity (excluding gaps) to the deduced amino acid sequence of a GH61 polypeptide from *Myceliophthora thermophila* (GENESEQP AZH97010).

Example 5: Expression of *Corynascus thermophiles* GH61 Genes in *Aspergillus oryzae*

Figure 2:
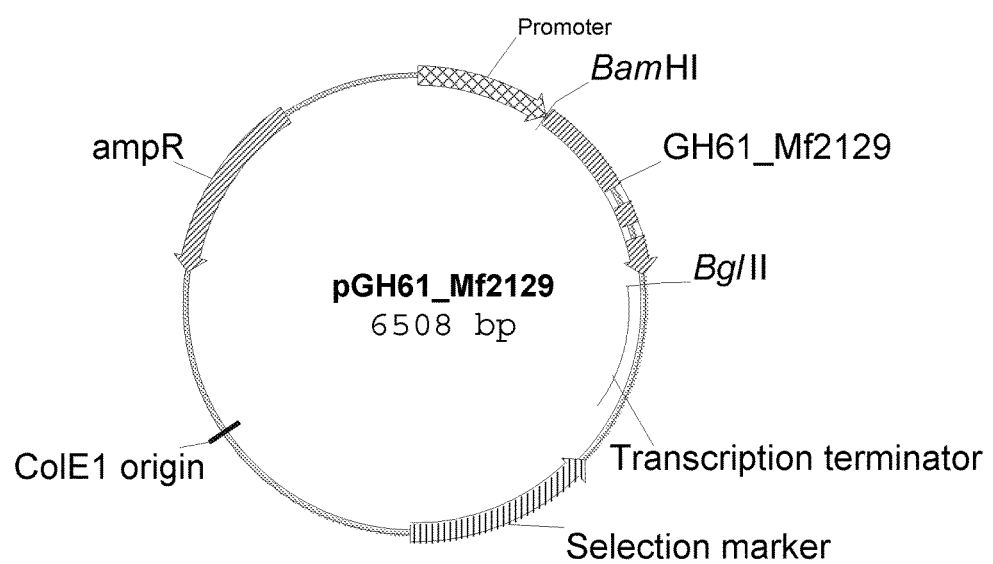
FIG. 2 shows a restriction map of plasmid of pGH61_Mf2129.
Figure 3:
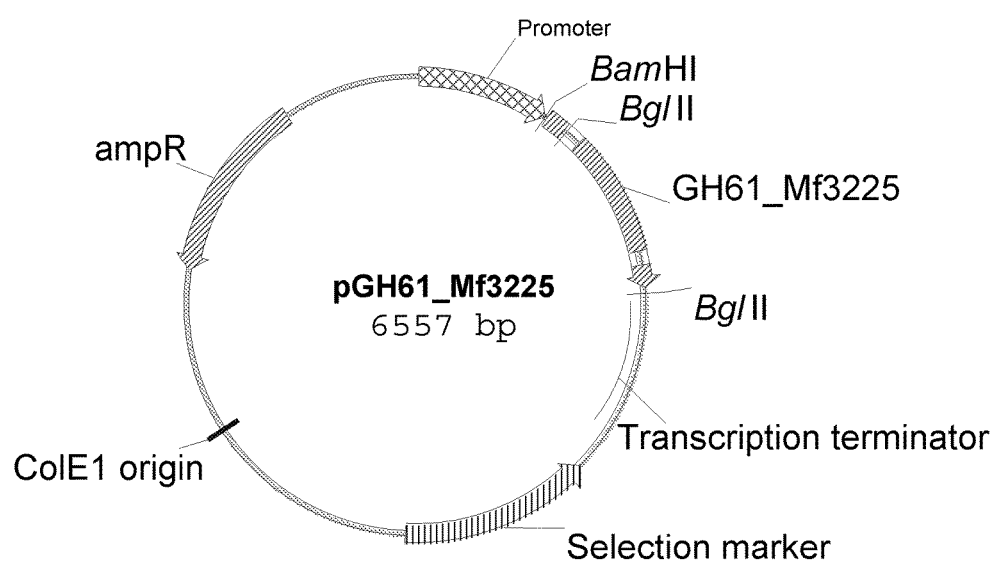
FIG. 3 shows a restriction map of plasmid of pGH61_Mf3225.
Figure 4:
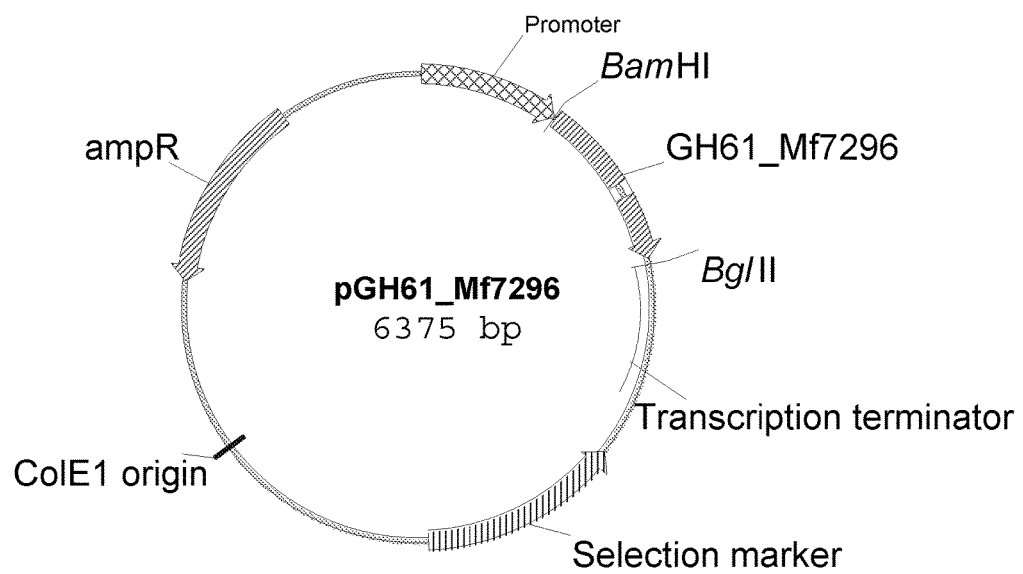
FIG. 4 shows a restriction map of plasmid of pGH61_Mf7296.
Figure 5:
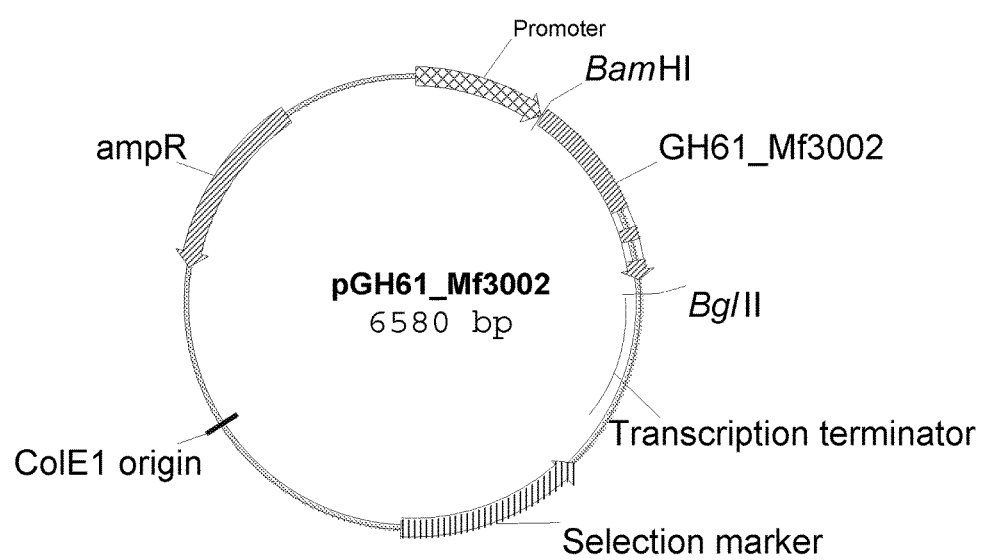
FIG. 5 shows a restriction map of plasmid of pGH61_Mf3002.
Figure 6:
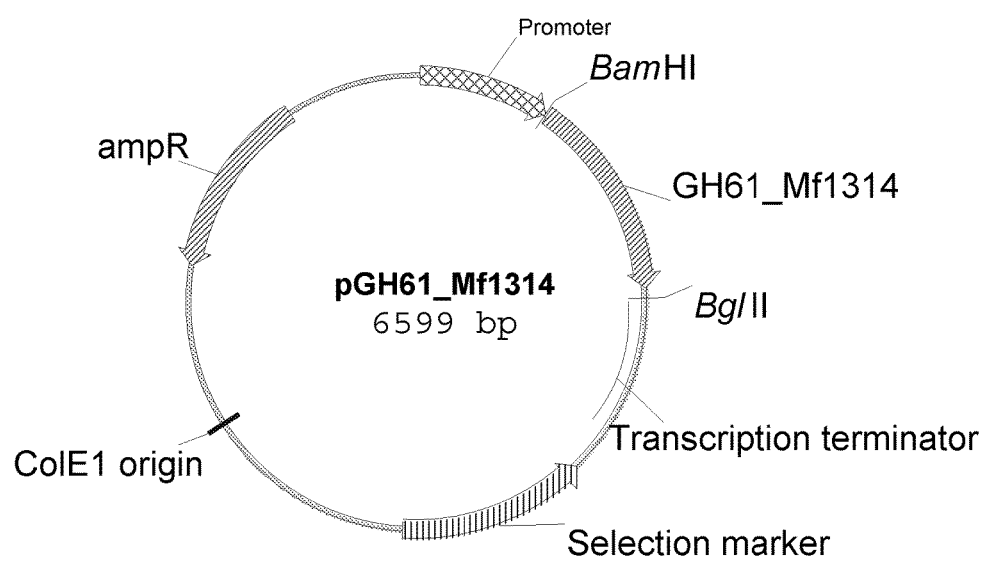
FIG. 6 shows a restriction map of plasmid of pGH61_Mf1314.
Figure 7:
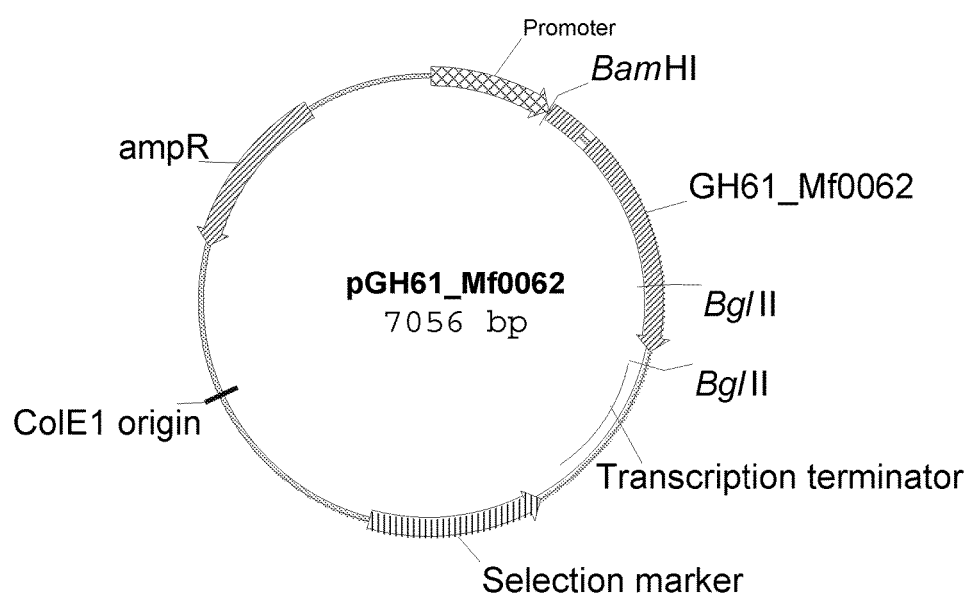
FIG. 7 shows a restriction map of plasmid of pGH61_Mf0062.
Figure 8:
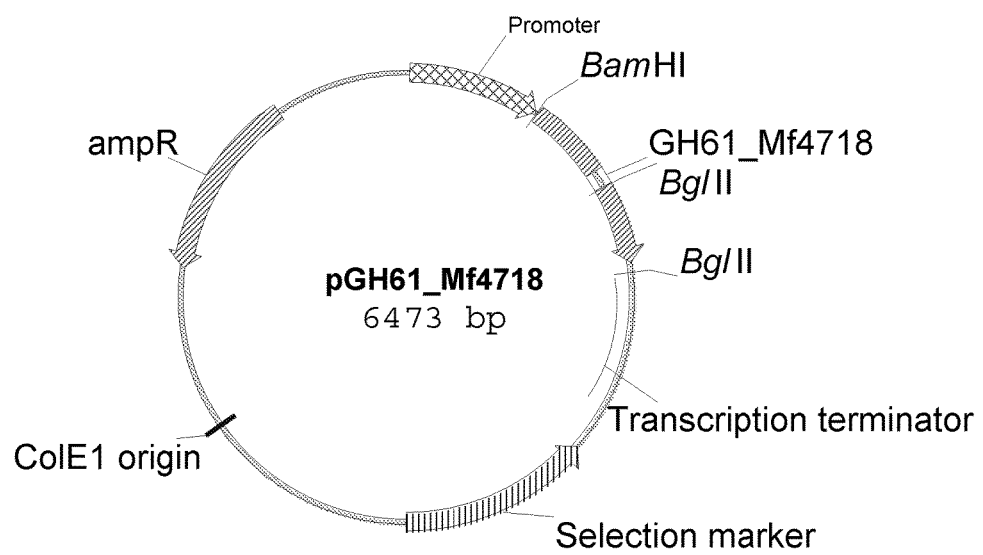
FIG. 8 shows a restriction map of plasmid of pGH61_Mf4718.
Figure 9:
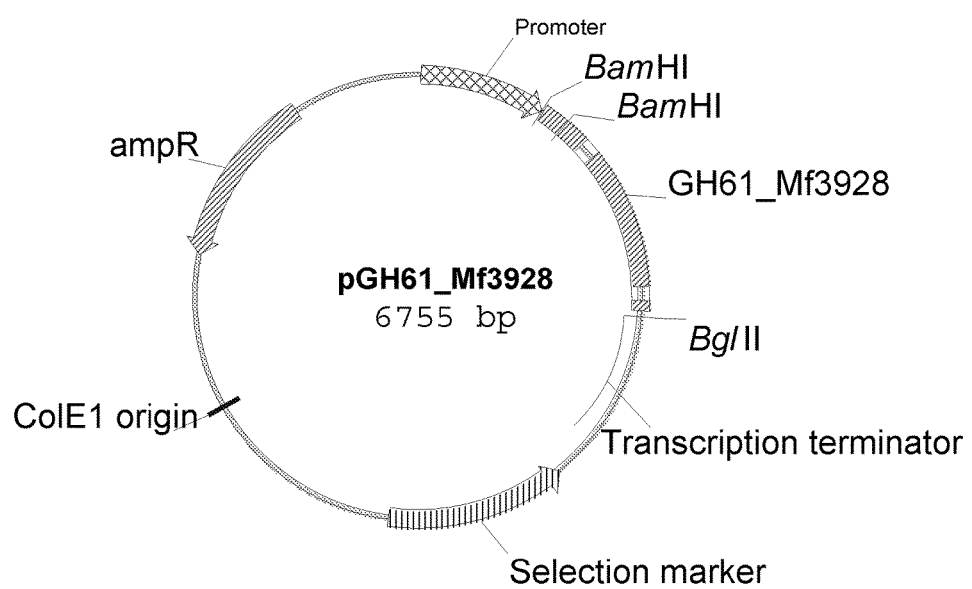
FIG. 9 shows a restriction map of plasmid of pGH61_Mf3928.
Figure 10:
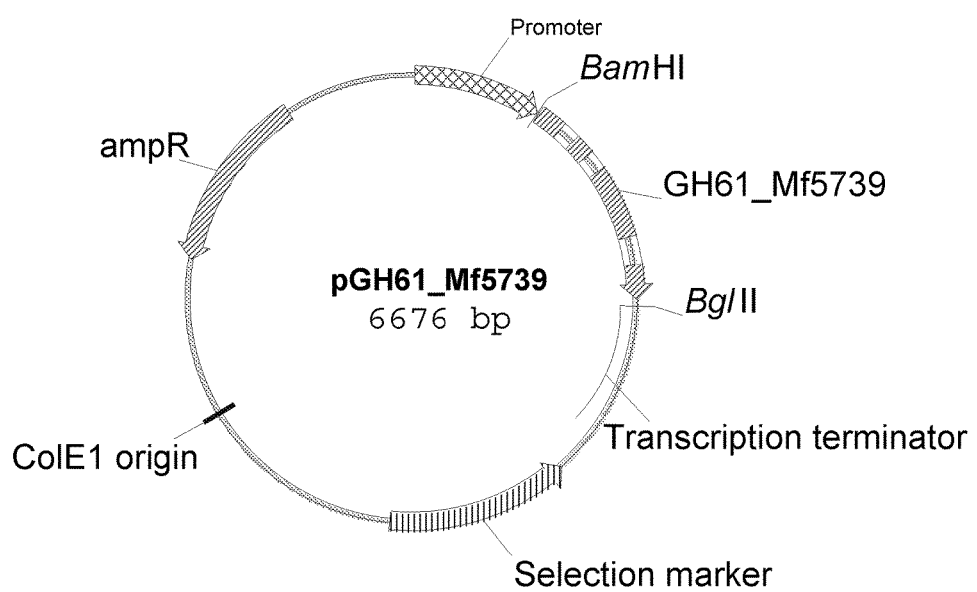
FIG. 10 shows a restriction map of plasmid of pGH61_Mf5739.
Figure 11:
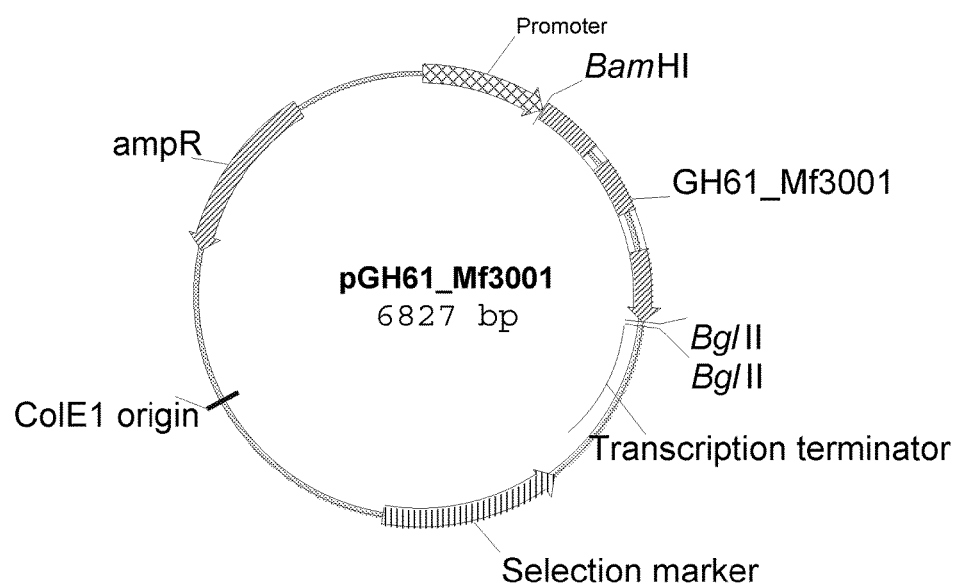
FIG. 11 shows a restriction map of plasmid of pGH61_Mf3001.
Figure 12:
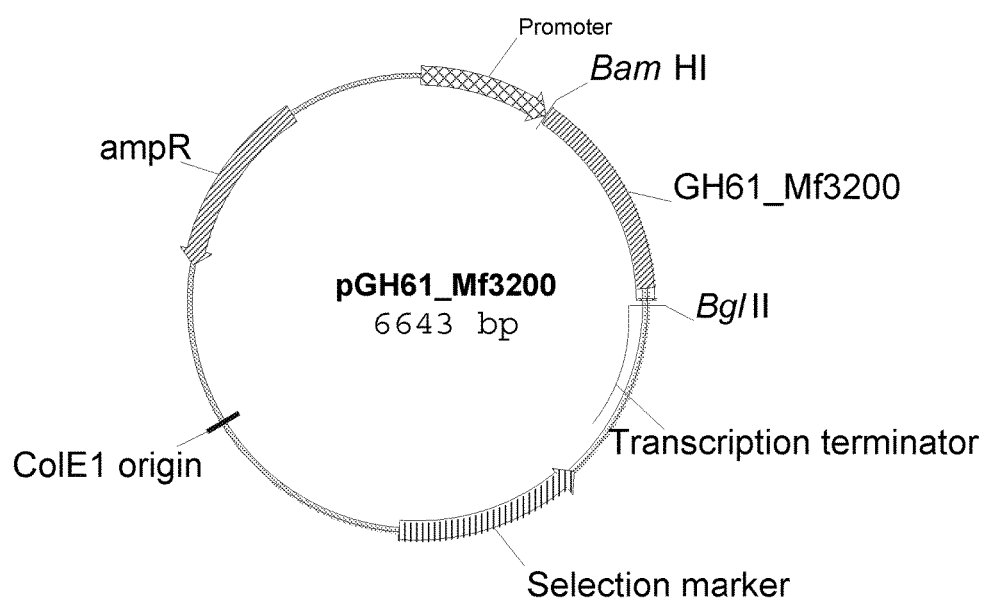
FIG. 12 shows a restriction map of plasmid of pGH61_Mf3200.
Figure 13:
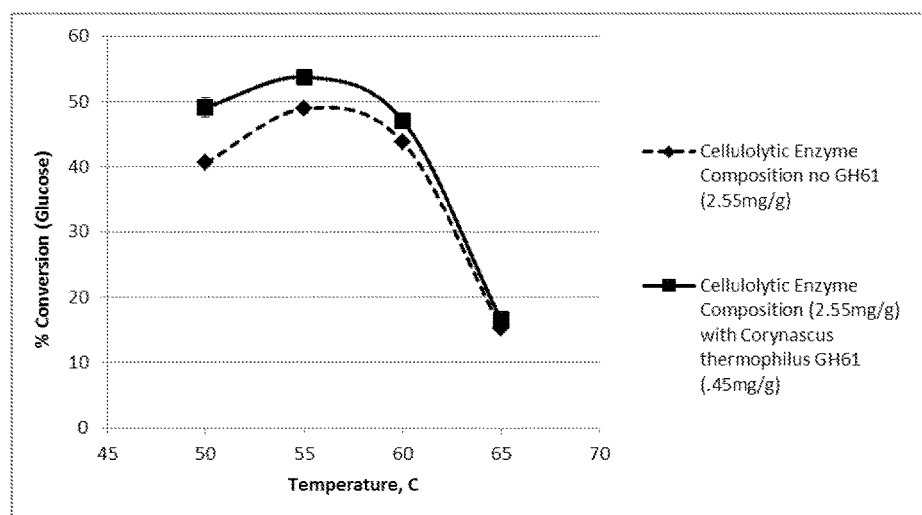
FIG. 13 shows the effect of the *Corynascus thermophilus* P24MRY GH61 polypeptide on the hydrolysis of milled unwashed PCS by a cellulolytic enzyme composition.

*Aspergillus oryzae* HowB101 (WO 95/035385 Example 1) protoplasts were prepared according to the method of Christensen et al., 1988, Bio/Technology 6: 1419-1422. Three μg of pGH61_Mf5285, pGH61_Mf2129, pGH61_Mf3225, pGH61_Mf7296, pGH61_Mf3002, pGH61_Mf1314, pGH61_Mf0062, pGH61_Mf4718, pGH61_Mf3928, pGH61_Mf5739, pGH61_Mf3001, and pGH61_Mf3200 (FIGS. 1-12, respectively) were each used to transform *Aspergillus oryzae* HowB101 separately.

The transformation of *Aspergillus oryzae* HowB101 with pGH61_Mf5285, pGH61_Mf2129, pGH61_Mf3225, pGH61_Mf7296, pGH61_Mf3002, pGH61_Mf1314, pGH61_Mf0062, pGH61_Mf4718, pGH61_Mf3928, pGH61_Mf5739, pGH61_Mf3001, or pGH61_Mf3200 yielded about 50 transformants for each transformation. Eight transformants from each transformation were isolated to individual selection plates.

Four transformants for each transformation were inoculated separately into 3 ml of YPM medium in a 24-well plate and incubated at 30° C., 150 rpm. After 3 days incubation, 20 μl of supernatant from each culture were analyzed by SDS-PAGE using a NUPAGE® NOVEX® 4-12% Bis-Tris Gel with MES (Invitrogen Corporation, Carlsbad, Calif., USA) according to the manufacturer's instructions. The resulting gel was stained with INSTANTBLUE™ (Expedeon Ltd., Babraham Cambridge, UK). The SDS-PAGE profiles of the cultures demonstrated the expression of the GH61 polypeptides. The sizes of major bands of the GH61 polypeptides are shown below in Table 5. The expression strains were designated as shown in the second column.

TABLE 5

| Expression | | |
|---|---|---|
| Plasmid | Expression strain | Size of recombinant protein (kDa) |
| pGH61_Mf5285 | O7R4B | smear 35 kDa |
| pGH61_Mf2129 | O7R4F | 2 bands at 25 kDa |
| pGH61_Mf3225 | O7R4H | 28 KDa |
| pGH61_Mf7296 | O7R4M | 2 bands around 25 kDa |
| pGH61_Mf3002 | O8KM4 | 30 kDa |
| pGH61_Mf1314 | O7SPT | 45 kDa |
| pGH61_Mf0062 | O7R4W | Smear at 45 kDa |
| pGH61_Mf4718 | O7R52 | Smear at 28 kDa |
| pGH61_Mf3928 | O8KM2 | 45 kDa |
| pGH61_Mf5739 | O7SPY | 24 kDa |
| pGH61_Mf3001 | O7SQ4 | 30 kDa |
| pGH61_Mf3200 | O7SQ5 | about 45 kDa |

Example 6: Fermentation of Expression Strains

A slant of each expression strain (Table 5) was inoculated into 4-6 two liter flasks containing 400 ml of YPM medium. The total culture volume of each expression strain is shown in Table 6. The shaking flasks were incubated at 30° C. for 3 days at 80 rpm. The cultures were harvested on day 3 and filtered using a 0.45 μm DURAPORE® Membrane (Millipore, Bedford, Mass., USA).

TABLE 6

Fermentation

| Expression strain | Culture volume (ml) |
|---|---|
| O7R4B | 3200 |
| O7R4F | 3200 |
| O7R4H | 3200 |
| O7R4M | 2400 |
| O8KM4 | 2400 |
| O7SPT | 3200 |
| O7R4W | 3200 |
| O7R52 | 3200 |
| O8KM2 | 3200 |
| O7SPY | 2400 |
| O7SQ4 | 4000 |
| O7SQ5 | 3200 |

Example 7: Purification of *Corynascus thermophilus* GH61 Proteins from *Aspergillus oryzae*

A 3200 ml volume of the *Aspergillus oryzae* O7R4F supernatant was precipitated with ammonium sulfate (80% saturation), re-dissolved in 50 ml of 20 mM Bis-Tris pH 6.0, dialyzed against the same buffer, and filtered through a 0.45 μm filter. The final volume was 80 ml. The solution was applied to a 40 ml Q SEPHAROSE® Fast Flow column (GE Heathcare Life Sciences, Piscataway, N.J., USA) equilibrated with 20 mM Bis-Tris pH 6.0, and the proteins were eluted with a linear 0-0.5 M NaCl gradient. Fractions eluted with 0-0.1 M NaCl were pooled. The pooled fractions were further purified using a 40 ml Phenyl SEPHAROSE® 6 Fast Flow column (GE Heathcare Life Sciences, Piscataway, N.J., USA) with a linear 1.2-0 M $(NH_4)_2SO_4$ gradient. Fractions were collected and analyzed by SDS-PAGE using a NUPAGE® NOVEX® 4-12% Bis-Tris Gel with MES. Fractions containing a band at approximately 25 kDa were pooled and concentrated by ultrafiltration.

A 3200 ml volume of the *Aspergillus oryzae* O7R4H supernatant was precipitated with ammonium sulfate (80% saturation), re-dissolved in 50 ml of 20 mM Bis-Tris pH 6.0, dialyzed against the same buffer, and filtered through a 0.45 μm filter. The final volume was 100 ml. The solution was applied to a 40 ml Q SEPHAROSE® Fast Flow column equilibrated with 20 mM Bis-Tris pH 6.5, and the proteins were eluted with a linear 0-0.5 M NaCl gradient. Fractions eluted with 0-0.1 M NaCl were pooled. The pooled fractions was further purified using a 40 ml Phenyl SEPHAROSE® 6 Fast Flow column (GE Heathcare Life Sciences, Piscataway, N.J., USA) with a linear 1.2-0 M $(NH_4)_2SO_4$ gradient. Fractions were collected and analyzed by SDS-PAGE using a NUPAGE® NOVEX® 4-12% Bis-Tris Gel with MES. Fractions containing a band at approximately 28 kDa were pooled and concentrated by ultrafiltration.

A 2400 ml volume of the *Aspergillus oryzae* O7R4M supernatant was precipitated with ammonium sulfate (80% saturation), re-dissolved in 50 ml of 20 mM Bis-Tris pH 6.0, dialyzed against the same buffer, and filtered through a 0.45 μm filter. The final volume was 80 ml. The solution was applied to a 40 ml Q SEPHAROSE® Fast Flow column equilibrated with 20 mM Bis-Tris pH 6.0, and the proteins were eluted with a linear 0-0.5 M NaCl gradient. Fractions containing protein that did not bind to the column were pooled and dialyzed against 20 mM Bis-Tris pH 6.5. The pooled dialyzed fractions were further purified on the same Q SEPHAROSE® Fast Flow column with a 0-0.25 M NaCl gradient. Fractions were collected and analyzed by SDS-PAGE using a NUPAGE® NOVEX® 4-12% Bis-Tris Gel with MES. Fractions containing a band at approximately 22 kDa were pooled and concentrated by ultrafiltration.

A 2400 ml volume of the *Aspergillus oryzae* O8KM4 supernatant was precipitated with ammonium sulfate (80% saturation), re-dissolved in 50 ml of 20 mM sodium acetate pH 5.5, dialyzed against the same buffer, and filtered through a 0.45 μm filter. The final volume was 80 ml. The solution was applied to a 40 ml Q SEPHAROSE® Fast Flow column equilibrated in 20 mM sodium acetate pH 5.5, and the proteins were eluted with a linear 0-0.5 M NaCl gradient. Fractions eluted with 0-0.1 M NaCl were pooled. The pooled fractions were further purified using a 40 ml Phenyl SEPHAROSE® 6 Fast Flow column with a linear 1.2-0 M $(NH_4)_2SO_4$ gradient. Fractions were collected and analyzed by SDS-PAGE using a NUPAGE® NOVEX® 4-12% Bis-Tris Gel with MES. Fractions containing a band at approximately 30 kDa were pooled and concentrated by ultrafiltration.

A 3200 ml volume of the *Aspergillus oryzae* O7SPT supernatant was precipitated with ammonium sulfate (80% saturation), re-dissolved in 50 ml of 20 mM sodium acetate pH 5.5, dialyzed against the same buffer, and filtered through a 0.45 μm filter. The final volume was 100 ml. The solution was applied to a 40 ml Q SEPHAROSE® Fast Flow column equilibrated with 20 mM sodium acetate pH 5.5, and the proteins were eluted with a linear 0-0.15 M NaCl gradient. Fractions were collected and analyzed by SDS-PAGE using a NUPAGE® NOVEX® 4-12% Bis-Tris Gel with MES. Fractions containing a band at approximately 45 kDa were pooled and concentrated by ultrafiltration.

A 3200 ml volume of the *Aspergillus oryzae* 07R4W supernatant was precipitated with ammonium sulfate (80% saturation), re-dissolved in 50 ml of 20 mM Tris-HCl pH 6.5, then dialyzed against the same buffer, and filtered through a 0.45 μm filter. The final volume was 105 ml. The solution was applied to a 40 ml Q SEPHAROSE® Fast Flow column equilibrated with 20 mM Tris-HCl pH 6.5, and the proteins was eluted with a linear 0-0.25 M NaCl gradient. Fractions were collected and analyzed by SDS-PAGE using a NUPAGE® NOVEX® 4-12% Bis-Tris Gel with MES. Fractions containing a band at approximately 45 kDa were pooled and concentrated by ultrafiltration.

A 3200 ml volume of the *Aspergillus oryzae* 07R52 supernatant was precipitated with ammonium sulfate (80% saturation), re-dissolved in 50 ml of 20 mM sodium acetate pH 5.5, dialyzed against the same buffer, and filtered through a 0.45 μm filter. The final volume was 80 ml. The solution was applied to a 40 ml Q SEPHAROSE® Fast Flow column equilibrated in 20 mM sodium acetate pH 5.5, and the proteins was eluted with a linear 0-0.5 M NaCl gradient. Fractions eluted with 0-0.1 M NaCl were pooled and dialyzed against the same equilibration buffer. The pooled dialyzed fractions were further purified on the SP SEPHAROSE® Fast Flow column (GE Heathcare Life Sciences, Piscataway, N.J., USA) with 0-0.5M NaCl gradient. Fractions were collected and analyzed by SDS-PAGE using a NUPAGE® NOVEX® 4-12% Bis-Tris Gel with MES. Fractions containing a band at approximately 28 kDa were pooled and concentrated by ultrafiltration.

A 3200 ml volume of the *Aspergillus oryzae* O8KM2 supernatant was precipitated with ammonium sulfate (80% saturation), re-dissolved in 50 ml of 20 mM Tris-HCl pH 7.5, dialyzed against the same buffer, and filtered through a 0.45 µm filter. The final volume was 110 ml. The solution was applied to a 40 ml Q SEPHAROSE® Fast Flow column equilibrated with 20 mM Tris-HCl pH 7.5, and the proteins were eluted with a linear 0-0.25 M NaCl gradient. Fractions were collected and analyzed by SDS-PAGE using a NUPAGE® NOVEX® 4-12% Bis-Tris Gel with MES. Fractions containing a band at approximately 45 kDa were pooled and concentrated by ultrafiltration.

A 2400 ml volume of the *Aspergillus oryzae* O7SPY supernatant was precipitated with ammonium sulfate (80% saturation), re-dissolved in 50 ml of 20 mM Bis-Tris pH 6.0, dialyzed against the same buffer, and filtered through a 0.45 µm filter. The final volume was 120 ml. The solution was applied to a 40 ml Q SEPHAROSE® Fast Flow column equilibrated with 20 mM Bis-Tris pH 6.0, and the proteins were eluted with a linear 0-0.5 M NaCl gradient. Fractions eluted with 0.1-0.2 M NaCl were pooled. The pooled fractions were further purified using a 40 ml Phenyl SEPHAROSE® 6 Fast Flow column with a linear 1.2-0 M $(NH_4)_2SO_4$ gradient. Fractions eluted with 1.2-0.8 M NaCl were pooled and further purified using a SUPERDEX® 75 column (GE Heathcare Life Sciences, Piscataway, N.J., USA). Fractions were evaluated by SDS-PAGE using a NUPAGE® NOVEX® 4-12% Bis-Tris Gel with MES. Fractions containing a band of approximately 24 kDa were pooled and further purified on MONO Q™ 16/10 column (GE Heathcare Life Sciences, Piscataway, N.J., USA) with 0-0.3 M NaCl gradient. Fractions were collected and analyzed by SDS-PAGE using a NUPAGE® NOVEX® 4-12% Bis-Tris Gel with MES. Fractions containing a band at approximately 24 kDa were pooled and concentrated by ultrafiltration.

A 4000 ml volume of the *Aspergillus oryzae* 075Q4 supernatant was precipitated with ammonium sulfate (80% saturation), re-dissolved in 50 ml of 20 mM Tris-HCl pH 7.5, dialyzed against the same buffer, and filtered through a 0.45 µm filter. The final volume was 75 ml. The solution was applied to a 40 ml Q SEPHAROSE® Fast Flow column equilibrated with 20 mM Tris-HCl pH 7.5, and the proteins were eluted with a linear 0-0.25 M NaCl gradient. Fractions eluted with 0.1-0.22 M NaCl were pooled and further purified using a 40 ml Q SEPHAROSE® Fast Flow column with a linear 0.07-0.2 M NaCl gradient. Fractions were collected and analyzed by SDS-PAGE using a NUPAGE® NOVEX® 4-12% Bis-Tris Gel with MES. Fractions containing a band at approximately 30 kDa were pooled and concentrated by ultrafiltration.

A 3200 ml volume of the *Aspergillus oryzae* 075Q5 supernatant was precipitated with ammonium sulfate (80% saturation), re-dissolved in 50 ml 20 mM sodium acetate pH 5.0, dialyzed against the same buffer, and filtered through a 0.45 mm filter, the final volume was 80 ml. The solution was applied to a 40 ml Q SEPHAROSE® Fast Flow equilibrated with 20 mM sodium acetate pH 5.0, and the proteins were eluted with a linear 0-0.25 M NaCl gradient. Fractions eluted with 0.1-0.2 M NaCl were pooled. The pooled fractions were further purified using a 40 ml Phenyl SEPHAROSE® 6 Fast Flow column (GE Heathcare Life Sciences, Piscataway, N.J., USA) with a linear 1.2-0 M $(NH_4)_2SO_4$ gradient. Fractions were collected and analyzed by SDS-PAGE using a NUPAGE® NOVEX® 4-12% Bis-Tris Gel with MES. Fractions containing a band at approximately 45 kDa were pooled and concentrated by ultrafiltration.

Example 5: Pretreated Corn Stover Hydrolysis Assay

Corn stover was pretreated at the U.S. Department of Energy National Renewable Energy Laboratory (NREL) using 1.4 wt % sulfuric acid at 165° C. and 107 psi for 8 minutes. The water-insoluble solids in the pretreated corn stover (PCS) contained 56.5% cellulose, 4.6% hemicellulose and 28.4% lignin. Cellulose and hemicellulose were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003.

Unmilled, unwashed PCS (whole slurry PCS) was prepared by adjusting the pH of the PCS to 5.0 by addition of 10 M NaOH with extensive mixing, and then autoclaving for 20 minutes at 120° C. The dry weight of the whole slurry PCS was 29%. Milled unwashed PCS (dry weight 32.35%) was prepared by milling whole slurry PCS in a Cosmos ICMG 40 wet multi-utility grinder (EssEmm Corporation, Tamil Nadu, India).

The hydrolysis of PCS was conducted using 2.2 ml deep-well plates (Axygen, Union City, Calif., USA) in a total reaction volume of 1.0 ml. The hydrolysis was performed with 50 mg of insoluble PCS solids per ml of 50 mM sodium acetate pH 5.0 buffer containing 1 mM manganese sulfate and various protein loadings of various enzyme compositions (expressed as mg protein per gram of cellulose). Enzyme compositions were prepared and then added simultaneously to all wells in a volume ranging from 50 µl to 200 µl, for a final volume of 1 ml in each reaction. The plate was then sealed using an ALPS300™ plate heat sealer, mixed thoroughly, and incubated at a specific temperature for 72 hours. All experiments reported were performed in triplicate.

Following hydrolysis, samples were filtered using a 0.45 µm MULTISCREEN® 96-well filter plate and the filtrates were analyzed for glucose content as described below. When not used immediately, filtered aliquots were frozen at −20° C. The glucose concentration of samples diluted in 0.005 M $H_2SO_4$ were measured using a 4.6×250 mm AMINEX® HPX-87H column by elution with 0.05% w/w benzoic acid-0.005 M $H_2SO_4$ at 65° C. at a flow rate of 0.6 ml per minute, and quantitation by integration of the glucose signal from refractive index detection (CHEMSTATION®, AGILENT® 1100 HPLC) calibrated by pure glucose samples. The resultant glucose equivalents were used to calculate the percentage of cellulose conversion for each reaction.

Measured glucose concentration was adjusted for the appropriate dilution factor. The net concentration of enzymatically-produced glucose from the milled unwashed PCS was determined by adjusting the measured glucose concentration for corresponding background glucose concentration in unwashed PCS at zero time point. All HPLC data processing was performed using MICROSOFT EXCEL™ software.

The degree of cellulose conversion to glucose was calculated using the following equation: % conversion=(glucose concentration/glucose concentration in a limit digest)×100. In order to calculate % conversion, a 100% conversion point was set based on a cellulase control (100 mg of Trichoderma reesei cellulase per gram cellulose), and all values were divided by this number and then multiplied by 100. Triplicate data points were averaged and standard deviation was calculated.

Example 6: Preparation of an Enzyme Composition

The *Aspergillus fumigatus* GH7A cellobiohydrolase I (SEQ ID NO: 65 [DNA sequence] and SEQ ID NO: 66 [deduced amino acid sequence]) was prepared recombinantly in *Aspergillus oryzae* as described in WO 2011/057140. The filtered broth of the *A. fumigatus* cellobiohydrolase I was concentrated and buffer exchanged using a tangential flow concentrator (Pall Filtron, Northborough, Mass., USA) equipped with a 10 kDa polyethersulfone membrane (Pall Filtron, Northborough, Mass., USA) with 20 mM Tris-HCl pH 8.0. The desalted broth of the *A. fumigatus* cellobiohydrolase I was loaded onto a Q SEPHAROSE® ion exchange column (GE Healthcare, Piscataway, N.J., USA) equilibrated in 20 mM Tris-HCl pH 8 and eluted using a linear 0 to 1 M NaCl gradient. Fractions were collected and fractions containing the cellobiohydrolase I were pooled based on SDS-PAGE analysis using 8-16% CRITERION® Stain-free SDS-PAGE gels (Bio-Rad Laboratories, Inc., Hercules, Calif., USA).

The *Aspergillus fumigatus* GH6A cellobiohydrolase II (SEQ ID NO: 67 [DNA sequence] and SEQ ID NO: 68 [deduced amino acid sequence]) was prepared recombinantly in *Aspergillus oryzae* as described in WO 2011/057140. The filtered broth of the *A. fumigatus* cellobiohydrolase II was buffer exchanged into 20 mM Tris pH 8.0 using a 400 ml SEPHADEX™ G-25 column (GE Healthcare, United Kingdom). The fractions were pooled and adjusted to 1.2 M ammonium sulphate-20 mM Tris pH 8.0. The equilibrated protein was loaded onto a PHENYL SEPHAROSE™ 6 Fast Flow column (high sub) (GE Healthcare, Piscataway, N.J., USA) equilibrated in 20 mM Tris pH 8.0 with 1.2 M ammonium sulphate, and bound proteins were eluted with 20 mM Tris pH 8.0 with no ammonium sulphate. The fractions were pooled.

The *Trichoderma reesei* GH5 endoglucanase II (SEQ ID NO: 69 [DNA sequence] and SEQ ID NO: 70 [deduced amino acid sequence]) was prepared recombinantly according to WO 2011/057140 using *Aspergillus oryzae* as a host. The filtered broth of the *T. reesei* endoglucanase II was desalted and buffer-exchanged into 20 mM Tris pH 8.0 using a tangential flow concentrator equipped with a 10 kDa polyethersulfone membrane.

The *Aspergillus fumigatus* GH10 xylanase (xyn3) (SEQ ID NO: 71 [DNA sequence] and SEQ ID NO: 72 [deduced amino acid sequence]) was prepared recombinantly according to WO 2006/078256 using *Aspergillus oryzae* BECh2 (WO 2000/39322) as a host. The filtered broth of the *A. fumigatus* xylanase was desalted and buffer-exchanged into 50 mM sodium acetate pH 5.0 using a HIPREP® 26/10 Desalting Column (GE Healthcare, Piscataway, N.J., USA).

The *Aspergillus fumigatus* Cel3A beta-glucosidase (SEQ ID NO: 73 [DNA sequence] and SEQ ID NO: 74 [deduced amino acid sequence]) was recombinantly prepared according to WO 2005/047499 using *Aspergillus oryzae* as a host. The filtered broth of *Aspergillus fumigatus* Cel3A beta-glucosidase was concentrated and buffer exchanged using a tangential flow concentrator equipped with a 10 kDa polyethersulfone membrane with 20 mM Tris-HCl pH 8.5. The sample was loaded onto a Q SEPHAROSE® High Performance column (GE Healthcare, Piscataway, N.J., USA) equilibrated in 20 mM Tris pH 8.5, and bound proteins were eluted with a linear gradient from 0-600 mM sodium chloride. Fractions were collected and fractions containing the *Aspergillus fumigatus* Cel3A beta-glucosidase were pooled based on SDS-PAGE analysis using 8-16% CRITERION® Stain-free SDS-PAGE gels. The fractions were concentrated and loaded onto a SUPERDEX® 75 HR 26/60 column equilibrated with 20 mM Tris-150 mM sodium chloride pH 8.5. Fractions were collected and fractions containing the *Aspergillus fumigatus* Cel3A beta-glucosidase were pooled based on SDS-PAGE analysis using 8-16% CRITERION® Stain-free SDS-PAGE gels.

The *Talaromyces emersonii* GH3 beta-xylosidase (SEQ ID NO: 75 [DNA sequence] and SEQ ID NO: 76 [deduced amino acid sequence]) was prepared recombinantly in *Aspergillus oryzae* as described in WO 2011/057140. The *Talaromyces emersonii* GH3 beta-xylosidase was desalted and buffer-exchanged into 50 mM sodium acetate pH 5.0 using a tangential flow concentrator equipped with a 10 kDa polyethersulfone membrane.

The protein concentration for each of the monocomponents described above was determined using a Microplate BCA™ Protein Assay Kit (Thermo Fischer Scientific, Waltham, Mass., USA) in which bovine serum albumin was used as a protein standard. An enzyme composition was prepared composed of each monocomponent as follows: 37% *Aspergillus fumigatus* Cel7A cellobiohydrolase I, 25% *Aspergillus fumigatus* Cel6A cellobiohydrolase II, 10% *Trichoderma reesei* GH5 endoglucanase II, 5% *Aspergillus fumigatus* GH10 xylanase, 5% *Aspergillus fumigatus* beta-glucosidase mutant, and 3% *Talaromyces emersonii* beta-xylosidase. The enzyme composition is designated herein as "cellulolytic enzyme composition".

Example 7: Effect of the *Corynascus thermophilus* P24MRY GH61 Polypeptide on the Hydrolysis of Milled Unwashed PCS by a Cellulolytic Enzyme Composition The *Corynascus thermophilus* P24MRY GH61 polypeptide was evaluated for the ability to enhance the hydrolysis of milled unwashed PCS (Example 6) by the cellulolytic enzyme composition (Example B) at 2.55 mg total protein per g cellulose at 50° C., 55° C., 60° C., and 65° C. The *Corynascus thermophilus* GH61 polypeptide was added at 0.45 mg protein per g cellulose.

The assay was performed as described in Example 5. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

As shown in FIG. 14, the cellulolytic enzyme composition that included the *Corynascus thermophilus* GH61 polypeptide significantly outperformed the cellulolytic enzyme composition (2.55 mg protein per g cellulose) without GH61 polypeptide. The degree of cellulose conversion to glucose for the *Corynascus thermophilus* GH61 polypeptide added to the cellulolytic enzyme composition was significantly higher than the cellulolytic enzyme composition without added GH61 at 50° C., 55° C., and 60° C.

The present invention is further described by the following numbered paragraphs:

[1] An isolated polypeptide having cellulolytic enhancing activity, selected from the group consisting of: (a) a polypeptide having at least 60% sequence identity to the mature polypeptide of SEQ ID NO: 2; at least 75% sequence identity to the mature polypeptide of SEQ ID NO: 12 or SEQ ID NO: 22; at least 80% sequence identity to the mature polypeptide of SEQ ID NO: 4, SEQ ID NO: 10, or SEQ ID NO: 24; at least 85% sequence identity to the mature polypeptide of SEQ ID NO: 6, SEQ ID NO: 16, or SEQ ID NO: 28; or at least 90% sequence identity to the mature polypeptide of SEQ ID NO: 8, SEQ ID NO: 14, SEQ ID NO: 18, SEQ ID NO: 20, SEQ ID NO: 26, SEQ ID NO: 30, or SEQ ID NO: 32; (b) a polypeptide encoded by a polynucleotide that hybridizes under at least medium-high stringency conditions with (i) the mature polypeptide coding sequence of SEQ ID NO: 1, or (ii) the full-length complement of (i); or at least high stringency conditions with (i) the mature polypeptide coding sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, or SEQ ID NO: 31, (ii) the cDNA sequence of SEQ ID NO: 3, SEQ ID NO: 5, SEQ ID NO: 7, SEQ ID NO: 11, SEQ ID NO: 13, SEQ ID NO: 15, SEQ ID NO: 17, SEQ ID NO: 19, SEQ ID NO: 23, SEQ ID NO: 25, SEQ ID NO: 27, SEQ ID NO: 29, or SEQ ID NO: 31, or (iii) the full-length complement of (i) or (ii); (c) a polypeptide encoded by a polynucleotide having at least 60% sequence identity to the mature polypeptide coding sequence of SEQ ID NO: 1; at least 75% sequence identity to the mature polypeptide coding sequence of SEQ ID NO: 11 or the cDNA sequence thereof, or SEQ ID NO: 21; at least 80% sequence identity to the mature polypeptide coding sequence of SEQ ID NO: 3 or the cDNA sequence thereof, SEQ ID NO: 9, or SEQ ID NO: 23 or the cDNA sequence thereof; at least 85% sequence identity to the mature polypeptide coding sequence of SEQ ID NO: 5, SEQ ID NO: 15, or SEQ ID NO: 27, or the cDNA sequences thereof; or at least 90% sequence identity to the mature polypeptide coding sequence of SEQ ID NO: 7, SEQ ID NO: 13, SEQ ID NO: 17, SEQ ID NO: 19, SEQ ID NO: 25, SEQ ID NO: 29, or SEQ ID NO: 31, or the cDNA sequences thereof; (d) a variant of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, or SEQ ID NO: 32 comprising a substitution, deletion, and/or insertion at one or more (e.g., several) positions; and (e) a fragment of the polypeptide of (a), (b), (c), or (d) that has cellulolytic enhancing activity.

[2] The polypeptide of paragraph 1, having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2; at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 12 or SEQ ID NO: 22; at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 4, SEQ ID NO: 10, or SEQ ID NO: 24; at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to mature polypeptide of SEQ ID NO: 6, SEQ ID NO: 16, or SEQ ID NO: 28; or at least 90%, at least 91%, at least 92%, at least 93%, at least 94%, at least 95%, at least 96%, or at least 97%, at least 98%, at least 99%, or 100% sequence identity to the mature polypeptide of SEQ ID NO: 8, SEQ ID NO: 14, SEQ ID NO: 18, SEQ ID NO: 20, SEQ ID NO: 26, SEQ ID NO: 30, or SEQ ID NO: 32.

[3] The polypeptide of paragraph 1 or 2, which is encoded by a polynucleotide that hybridizes under medium-high, high, or very high stringency conditions with (i) the mature polypeptide coding sequence of SEQ ID NO: 1, or (ii) the full-length complement of (i); or high or very high stringency conditions with (i) the mature polypeptide coding sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, or SEQ ID NO: 31, (ii) the cDNA sequence of SEQ ID NO: 3, SEQ ID NO: 5, SEQ ID NO: 7, SEQ ID NO: 11, SEQ ID NO: 13, SEQ ID NO: 15, SEQ ID NO: 17, SEQ ID NO: 19, SEQ ID NO: 23, SEQ ID NO: 25, SEQ ID NO: 27, SEQ ID NO: 29, or SEQ ID NO: 31, or (iii) the full-length complement of (i) or (ii).

[4] The polypeptide of any of paragraphs 1-3, which is encoded by a polynucleotide having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1; at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 11 or the cDNA sequence thereof or SEQ ID NO: 21; at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 3 or the cDNA sequence thereof, SEQ ID NO: 9, or SEQ ID NO: 23 or the cDNA sequence thereof; at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to mature polypeptide coding sequence of SEQ ID NO: 5, SEQ ID NO: 15, or SEQ ID NO: 27, or the cDNA sequences thereof; or at least 90%, at least 91%, at least 92%, at least 93%, at least 94%, at least 95%, at least 96%, or at least 97%, at least 98%, at least 99%, or 100% sequence identity to the mature polypeptide coding sequence of SEQ ID NO: 7, SEQ ID NO: 13, SEQ ID NO: 17, SEQ ID NO: 19, SEQ ID NO: 25, SEQ ID NO: 29, or SEQ ID NO: 31, or the cDNA sequences thereof.

[5] The polypeptide of any of paragraphs 1-4, comprising or consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, or SEQ ID NO: 32 or the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, or SEQ ID NO: 32.

[6] The polypeptide of paragraph 5, wherein the mature polypeptide is amino acids 24 to 324 of SEQ ID NO: 2, amino acids 21 to 240 of SEQ ID NO: 4, amino acids 21 to 225 of SEQ ID NO: 6, amino acids 16 to 235 of SEQ ID NO: 8, amino acids 20 to 336 of SEQ ID NO: 10, amino acids 17 to 253 of SEQ ID NO: 12, amino acids 18 to 255 of SEQ ID NO: 14, amino acids 18 to 225 of SEQ ID NO: 16, amino acids 16 to 237 of SEQ ID NO: 18, amino acids 18 to 227 of SEQ ID NO: 20, amino acids 22 to 315 of SEQ ID NO: 22, amino acids 21 to 439 of SEQ ID NO: 24, amino acids 18 to 246 of SEQ ID NO: 26, amino acids 19 to 324 of SEQ ID NO: 28, amino acids 21 to 242 of SEQ ID NO: 30, or amino acids 16 to 306 of SEQ ID NO: 32.

[7] The polypeptide of any of paragraphs 1-4, which is a variant of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, or SEQ ID NO: 32 comprising a substitution, deletion, and/or insertion at one or more positions (e.g., several).

[8] The polypeptide of paragraph 1, which is a fragment of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, or SEQ ID NO: 32, wherein the fragment has cellulolytic enhancing activity.

[9] The polypeptide of any of paragraphs 1-8, which is encoded by the polynucleotide contained in Corynascus thermophilus CBS 174.70.

[10] An isolated polypeptide comprising a catalytic domain selected from the group consisting of: (a) a catalytic domain having at least 80% sequence identity to amino acids 20 to 251 of SEQ ID NO: 10 or amino acids 21 to 244 of SEQ ID NO: 24; at least 85% sequence identity to amino acids 19 to 241 of SEQ ID NO: 28, or at least 90% sequence identity to amino acids 16 to 243 of SEQ ID NO: 32; (b) a catalytic domain encoded by a polynucleotide that hybridizes under at least high stringency conditions with (i) nucleotides 58 to 753 of SEQ ID NO: 9, nucleotides 61 to 792 of SEQ ID NO: 23 or the cDNA sequence thereof, nucleotides 55 to 803 of SEQ ID NO: 27 or the cDNA sequence thereof, or nucleotides 46 to 1008 of SEQ ID NO: 31 or the cDNA sequence thereof, or (ii) the full-length complement of (i); (c) a catalytic domain encoded by a polynucleotide having at least 80% sequence identity to nucleotides 58 to 753 of SEQ ID NO: 9, or nucleotides 61 to 792 of SEQ ID NO: 23 or the cDNA sequence thereof, at least 85% sequence identity to nucleotides 55 to 803 of SEQ ID NO: 27 or the cDNA sequence thereof, or at least 90% sequence identity to nucleotides 46 to 1008 of SEQ ID NO: 31 or the cDNA sequence thereof; (d) a variant of amino acids 20 to 251 of SEQ ID NO: 10, amino acids 21 to 244 of SEQ ID NO: 24, amino acids 19 to 241 of SEQ ID NO: 28, or amino acids 16 to 243 of SEQ ID NO: 32 comprising a substitution, deletion, and/or insertion at one or more (e.g., several) positions; and (e) a fragment of the catalytic domain of (a), (b), (c), or (d) that has cellulolytic enhancing activity.

[11] The polypeptide of paragraph 10, further comprising a cellulose binding domain.

[12] An isolated polypeptide comprising a cellulose binding domain operably linked to a catalytic domain, wherein the binding domain is selected from the group consisting of: (a) a cellulose binding domain having at least 80% sequence identity to amino acids 304 to 332 of SEQ ID NO: 10 or amino acids 282 to 337 of SEQ ID NO: 24, at least 85% sequence identity to amino acids 291 to 319 of SEQ ID NO: 28, or at least 90% sequence identity to amino acids 274 to 301 of SEQ ID NO: 32; (b) a cellulose binding domain encoded by a polynucleotide that hybridizes under at least high stringency conditions with (i) nucleotides 910 to 996 of SEQ ID NO: 9, nucleotides 904 to 1071 of SEQ ID NO: 23, nucleotides 951 to 1107 of SEQ ID NO: 27 or the cDNA sequence thereof, or nucleotides 1099 to 1182 of SEQ ID NO: 31, or (ii) the full-length complement of (i); (c) a cellulose binding domain encoded by a polynucleotide having at least 80% sequence identity to nucleotides 910 to 996 of SEQ ID NO: 9 or nucleotides 904 to 1071 of SEQ ID NO: 23, at least 85% sequence identity to nucleotides 951 to 1107 of SEQ ID NO: 27 the cDNA sequence thereof, or at least 90% sequence identity to nucleotides 1099 to 1182 of SEQ ID NO: 31; (d) a variant of amino acids 304 to 332 of SEQ ID NO: 10, amino acids 282 to 337 of SEQ ID NO: 24, amino acids 291 to 319 of SEQ ID NO: 28, or amino acids 274 to 301 of SEQ ID NO: 32 comprising a substitution, deletion, and/or insertion at one or more (e.g., several) positions; and (e) a fragment of the cellulose binding domain of (a), (b), (c), or (d) that has binding activity.

[13] The polypeptide of paragraph 12, wherein the catalytic domain is obtained from a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

[14] A composition comprising the polypeptide of any of paragraphs 1-13.

[15] An isolated polynucleotide encoding the polypeptide of any of paragraphs 1-13.

[16] A nucleic acid construct or expression vector comprising the polynucleotide of paragraph 15 operably linked to one or more control sequences that direct the production of the polypeptide in an expression host.

[17] A recombinant host cell comprising the polynucleotide of paragraph 15 operably linked to one or more control sequences that direct the production of the polypeptide.

[18] A method of producing the polypeptide of any of paragraphs 1-13, comprising: cultivating a cell, which in its wild-type form produces the polypeptide, under conditions conducive for production of the polypeptide.

[19] The method of paragraph 18, further comprising recovering the polypeptide.

[22] A method of producing a polypeptide having cellulolytic enhancing activity, comprising: cultivating the host cell of paragraph 17 under conditions conducive for production of the polypeptide.

[21] The method of paragraph 20, further comprising recovering the polypeptide.

[22] A transgenic plant, plant part or plant cell transformed with a polynucleotide encoding the polypeptide of any of paragraphs 1-13.

[23] A method of producing a polypeptide having cellulolytic enhancing activity, comprising: cultivating the transgenic plant or plant cell of paragraph 22 under conditions conducive for production of the polypeptide.

[24] The method of paragraph 23, further comprising recovering the polypeptide.

[25] A method of producing a mutant of a parent cell, comprising inactivating a polynucleotide encoding the polypeptide of any of paragraphs 1-13, which results in the mutant producing less of the polypeptide than the parent cell.

[26] A mutant cell produced by the method of paragraph 25.

[27] The mutant cell of paragraph 26, further comprising a gene encoding a native or heterologous protein.

[28] A method of producing a protein, comprising: cultivating the mutant cell of paragraph 25 or 26 under conditions conducive for production of the protein.

[29] The method of paragraph 28, further comprising recovering the protein.

[30] A double-stranded inhibitory RNA (dsRNA) molecule comprising a subsequence of the polynucleotide of paragraph 15, wherein optionally the dsRNA is an siRNA or an miRNA molecule.

[31] The double-stranded inhibitory RNA (dsRNA) molecule of paragraph 30, which is about 15, 16, 17, 18, 19, 20, 21, 22, 23, 24, 25 or more duplex nucleotides in length.

[32] A method of inhibiting the expression of a polypeptide having cellulolytic enhancing activity in a cell, comprising administering to the cell or expressing in the cell the double-stranded inhibitory RNA (dsRNA) molecule of paragraph 30 or 31.

[33] A cell produced by the method of paragraph 32.

[34] The cell of paragraph 33, further comprising a gene encoding a native or heterologous protein.

[35] A method of producing a protein, comprising: cultivating the cell of paragraph 33 or 34 under conditions conducive for production of the protein.

[36] The method of paragraph 35, further comprising recovering the protein.

[37] An isolated polynucleotide encoding a signal peptide comprising or consisting of amino acids 1 to 23 of SEQ ID NO: 2, amino acids 1 to 20 of SEQ ID NO: 4, amino acids 1 to 20 of SEQ ID NO: 6, amino acids 1 to 15 of SEQ ID NO: 8, amino acids 1 to 19 of SEQ ID NO: 10, amino acids 1 to 16 of SEQ ID NO: 12, amino acids 1 to 17 of SEQ ID NO: 14, amino acids 1 to 17 of SEQ ID NO: 16, amino acids 1 to 15 of SEQ ID NO: 18, amino acids 1 to 17 of SEQ ID NO: 20, amino acids 1 to 21 of SEQ ID NO: 22, amino acids 1 to 20 of SEQ ID NO: 24, amino acids 1 to 17 of SEQ ID NO: 26, amino acids 1 to 18 of SEQ ID NO: 28, amino acids 1 to 20 of SEQ ID NO: 30, or amino acids 1 to 15 of SEQ ID NO: 36.

[38] A nucleic acid construct or expression vector comprising a gene encoding a protein operably linked to the polynucleotide of paragraph 36, wherein the gene is foreign to the polynucleotide encoding the signal peptide.

[39] A recombinant host cell comprising a gene encoding a protein operably linked to the polynucleotide of paragraph 36, wherein the gene is foreign to the polynucleotide encoding the signal peptide.

[40] A method of producing a protein, comprising: cultivating a recombinant host cell comprising a gene encoding a protein operably linked to the polynucleotide of paragraph 32, wherein the gene is foreign to the polynucleotide encoding the signal peptide, under conditions conducive for production of the protein.

[41] The method of paragraph 40, further comprising recovering the polypeptide.

[42] A process for degrading a cellulosic material, comprising: treating the cellulosic material with an enzyme composition in the presence of the polypeptide having cellulolytic enhancing activity of any of paragraphs 1-13.

[43] The process of paragraph 42, wherein the cellulosic material is pretreated.

[44] The process of paragraph 42 or 43, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[45] The process of paragraph 44, wherein the cellulase is one or more enzymes selected from the group consisting of an endoglucanase, a cellobiohydrolase, and a beta-glucosidase.

[46] The process of paragraph 44, wherein the hemicellulase is one or more enzymes selected from the group consisting of a xylanase, an acetylxylan esterase, a feruloyl esterase, an arabinofuranosidase, a xylosidase, and a glucuronidase.

[47] The process of any of paragraphs 42-46, further comprising recovering the degraded cellulosic material.

[48] The process of paragraph 47, wherein the degraded cellulosic material is a sugar.

[49] The process of paragraph 48, wherein the sugar is selected from the group consisting of glucose, xylose, mannose, galactose, and arabinose.

[50] A process for producing a fermentation product, comprising: (a) saccharifying a cellulosic material with an enzyme composition in the presence of the polypeptide having cellulolytic enhancing activity of any of paragraphs 1-13; (b) fermenting the saccharified cellulosic material with one or more fermenting microorganisms to produce the fermentation product; and (c) recovering the fermentation product from the fermentation.

[51] The process of paragraph 50, wherein the cellulosic material is pretreated.

[52] The process of paragraph 50 or 51, wherein the enzyme composition comprises the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[53] The process of paragraph 52, wherein the cellulase is one or more enzymes selected from the group consisting of an endoglucanase, a cellobiohydrolase, and a beta-glucosidase.

[54] The process of paragraph 52, wherein the hemicellulase is one or more enzymes selected from the group consisting of a xylanase, an acetylxylan esterase, a feruloyl esterase, an arabinofuranosidase, a xylosidase, and a glucuronidase.

[55] The process of any of paragraphs 50-54, wherein steps (a) and (b) are performed simultaneously in a simultaneous saccharification and fermentation.

[56] The process of any of paragraphs 50-55, wherein the fermentation product is an alcohol, an alkane, a cycloalkane, an alkene, an amino acid, a gas, isoprene, a ketone, an organic acid, or polyketide.

[57] A process of fermenting a cellulosic material, comprising: fermenting the cellulosic material with one or more fermenting microorganisms, wherein the cellulosic material is saccharified with an enzyme composition in the presence of the polypeptide having cellulolytic enhancing activity of any of paragraphs 1-13.

[58] The process of paragraph 57, wherein the fermenting of the cellulosic material produces a fermentation product.

[59] The process of paragraph 58, further comprising recovering the fermentation product from the fermentation.

[60] The process of paragraph 58 or 59, wherein the fermentation product is an alcohol, an alkane, a cycloalkane, an alkene, an amino acid, a gas, isoprene, a ketone, an organic acid, or polyketide.

[61] The process of any of paragraphs 57-60, wherein the cellulosic material is pretreated before saccharification.

[62] The process of any of paragraphs 57-61, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[63] The process of paragraph 62, wherein the cellulase is one or more enzymes selected from the group consisting of an endoglucanase, a cellobiohydrolase, and a beta-glucosidase.

[64] The process of paragraph 62, wherein the hemicellulase is one or more enzymes selected from the group consisting of a xylanase, an acetylxylan esterase, a feruloyl esterase, an arabinofuranosidase, a xylosidase, and a glucuronidase.

[65] A whole broth formulation or cell culture composition comprising the polypeptide of any of paragraphs 1-13.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A nucleic acid construct comprising a polynucleotide encoding a GH61 polypeptide having cellulolytic enhancing activity operably linked to one or more heterologous control sequences that direct the production of the GH61 polypeptide, wherein the GH61 polypeptide having cellulolytic enhancing activity is selected from the group consisting of:
   (a) a GH61 polypeptide comprising an amino acid sequence having at least 95% sequence identity to the amino acid sequence of amino acids 20 to 336 of SEQ ID NO: 10;
   (b) a GH61 polypeptide encoded by a polynucleotide comprising a nucleotide sequence having at least 95% sequence identity to the nucleotide sequence of nucleotides 58 to 1008 of SEQ ID NO: 9;
   (c) a GH61 polypeptide comprising an amino acid sequence having the amino acid sequence of amino acids 20 to 251 of SEQ ID NO: 10; and
   (d) a GH61 polypeptide encoded by a polynucleotide comprising a nucleotide sequence having at least 95% sequence identity to the nucleotide sequence of nucleotides 58 to 753 of SEQ ID NO: 9.

2. A recombinant host cell comprising the nucleic acid construct of claim 1.

3. A method of producing a GH61 polypeptide having cellulolytic enhancing activity, comprising:
   (a) cultivating the recombinant host cell of claim 2 under conditions conducive for production of the polypeptide; and optionally
   (b) recovering the GH61 polypeptide.

4. A transgenic plant or plant cell transformed with the nucleic acid construct of claim 1.

5. A method of producing a GH61 polypeptide having cellulolytic enhancing activity, comprising:
   (a) cultivating the transgenic plant or plant cell of claim 4 under conditions conducive for production of the polypeptide; and optionally
   (b) recovering the GH61 polypeptide.

6. A process for degrading a cellulosic material, comprising: treating the cellulosic material with an enzyme composition comprising a GH61 polypeptide having cellulolytic enhancing activity, wherein the GH61 polypeptide having cellulolytic enhancing activity is selected from the group consisting of:
   (a) a GH61 polypeptide comprising an amino acid sequence having at least 95% sequence identity to the amino acid sequence of amino acids 20 to 336 of SEQ ID NO: 10;
   (b) a GH61 polypeptide encoded by a polynucleotide comprising a nucleotide sequence having at least 95% sequence identity to the nucleotide sequence of nucleotides 58 to 1008 of SEQ ID NO: 9;
   (c) a GH61 polypeptide comprising an amino acid sequence having the amino acid sequence of amino acids 20 to 251 of SEQ ID NO: 10; and
   (d) a GH61 polypeptide encoded by a polynucleotide comprising a nucleotide sequence having at least 95% sequence identity to] the nucleotide sequence of nucleotides 58 to 753 of SEQ ID NO: 9.

7. A process for producing a fermentation product, comprising:
   (a) saccharifying a cellulosic material with an enzyme composition comprising a polypeptide having cellulolytic enhancing activity, wherein the polypeptide having cellulolytic enhancing activity is selected from the group consisting of:
      i) a GH61 polypeptide comprising an amino acid sequence having at least 95% sequence identity to the amino acid sequence of amino acids 20 to 336 of SEQ ID NO: 10;
      (ii) a GH61 polypeptide encoded by a polynucleotide comprising a nucleotide sequence having at least 95% sequence identity to the nucleotide sequence of nucleotides 58 to 1008 of SEQ ID NO: 9;
      (iii) a GH61 polypeptide comprising an amino acid sequence having the amino acid sequence of amino acids 20 to 251 of SEQ ID NO: 10; and
      (iv) a GH61 polypeptide encoded by a polynucleotide comprising a nucleotide sequence having at least 95% sequence identity to the nucleotide sequence of nucleotides 58 to 753 of SEQ ID NO: 9;
   (b) fermenting the saccharified cellulosic material with one or more fermenting microorganisms to produce the fermentation product; and
   (c) recovering the fermentation product from the fermentation.

8. A process of fermenting a cellulosic material, comprising: fermenting the cellulosic material with one or more fermenting microorganisms, wherein the cellulosic material is saccharified with an enzyme composition comprising a GH61 polypeptide having cellulolytic enhancing activity, wherein the GH61 polypeptide having cellulolytic enhancing activity is selected from the group consisting of:
   (a) a GH61 polypeptide comprising an amino acid sequence having at least 95% sequence identity to the amino acid sequence of amino acids 20 to 336 of SEQ ID NO: 10;
   (b) a GH61 polypeptide encoded by a polynucleotide comprising a nucleotide sequence having at least 95% sequence identity to the nucleotide sequence of nucleotides 58 to 1008 of SEQ ID NO: 9;
   (c) a GH61 polypeptide comprising an amino acid sequence having the amino acid sequence of amino acids 20 to 251 of SEQ ID NO: 10; and
   (d) a GH61 polypeptide encoded by a polynucleotide comprising a nucleotide sequence having at least 95% sequence identity to the nucleotide sequence of nucleotides 58 to 753 of SEQ ID NO: 9.

9. The nucleic acid construct of claim 1, wherein the GH61 polypeptide having cellulolytic enhancing activity comprises an amino acid sequence having at least 96% sequence identity to the amino acid sequence of amino acids 20 to 336 of SEQ ID NO: 10.

10. The nucleic acid construct of claim 1, wherein the GH61 polypeptide having cellulolytic enhancing activity comprises an amino acid sequence having at least 97% sequence identity to the amino acid sequence of amino acids 20 to 336 of SEQ ID NO: 10.

11. The nucleic acid construct of claim 1, wherein the GH61 polypeptide having cellulolytic enhancing activity comprises the amino acid sequence of SEQ ID NO: 10, or the amino acid sequence of amino acids 20 to 336 of SEQ ID NO: 10.

12. The process of claim 6, wherein the cellulosic material is pretreated by steam pretreatment with explosion, steam pretreatment without explosion, dilute acid pretreatment, hot water pretreatment, alkaline pretreatment, lime pretreatment, wet oxidation pretreatment, wet explosion pretreatment, ammonia fiber explosion pretreatment, organosolv pretreatment, biological pretreatment, ammonia percolation pretreatment, ultrasound pretreatment, electroporation pretreatment, microwave pretreatment, supercritical $CO_2$ pretreatment, supercritical $H_2O$ pretreatment, ozone pretreatment, ionic liquid pretreatment, or gamma irradiation pretreatment.

13. The process of claim 6, wherein the enzyme composition further comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

14. The process of claim 13, wherein the enzyme is a cellulase, wherein the cellulase is one or more enzymes selected from the group consisting of an endoglucanase, a cellobiohydrolase, and a beta-glucosidase.

15. The process of claim 13, wherein the enzyme is a hemicellulase, wherein the hemicellulase is one or more enzymes selected from the group consisting of a xylanase, an acetylxylan esterase, a feruloyl esterase, an arabinofuranosidase, a xylosidase, and a glucuronidase.

16. The process of claim 6, further comprising recovering the degraded cellulosic material.

17. The process of claim 16, wherein the degraded cellulosic material is a sugar.

18. The process of claim 17, wherein the sugar is selected from the group consisting of glucose, xylose, mannose, galactose, and arabinose.

19. The process of claim 6, wherein the GH61 polypeptide having cellulolytic enhancing activity comprises the amino acid sequence of SEQ ID NO: 10, or the amino acid sequence of amino acids 20 to 336 of SEQ ID NO: 10.

20. The process of claim 7, wherein the cellulosic material is pretreated by steam pretreatment with explosion, steam pretreatment without explosion, dilute acid pretreatment, hot water pretreatment, alkaline pretreatment, lime pretreatment, wet oxidation pretreatment, wet explosion pretreatment, ammonia fiber explosion pretreatment, organosolv pretreatment, biological pretreatment, ammonia percolation pretreatment, ultrasound pretreatment, electroporation pretreatment, microwave pretreatment, supercritical $CO_2$ pretreatment, supercritical $H_2O$ pretreatment, ozone pretreatment, ionic liquid pretreatment, or gamma irradiation pretreatment.

21. The process of claim 7, wherein the enzyme composition further comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

22. The process of claim 21, wherein the enzyme is a cellulase, wherein the cellulase is one or more enzymes selected from the group consisting of an endoglucanase, a cellobiohydrolase, and a beta-glucosidase.

23. The process of claim 21, wherein the enzyme is a hemicellulase, wherein the hemicellulase is one or more enzymes selected from the group consisting of a xylanase, an acetylxylan esterase, a feruloyl esterase, an arabinofuranosidase, a xylosidase, and a glucuronidase.

24. The process of claim 7, wherein steps (a) and (b) are performed simultaneously in a simultaneous saccharification and fermentation.

25. The process of claim 7, wherein the fermentation product is an alcohol, an alkane, a cycloalkane, an alkene, an amino acid, a gas, isoprene, a ketone, an organic acid, or polyketide.

26. The process of claim 7, wherein the GH61 polypeptide having cellulolytic enhancing activity comprises the amino acid sequence of SEQ ID NO: 10, or the amino acid sequence of amino acids 20 to 336 of SEQ ID NO: 10.

27. The process of claim 8, wherein the cellulosic material is pretreated by steam pretreatment with explosion, steam pretreatment without explosion, dilute acid pretreatment, hot water pretreatment, alkaline pretreatment, lime pretreatment, wet oxidation pretreatment, wet explosion pretreatment, ammonia fiber explosion pretreatment, organosolv pretreatment, biological pretreatment, ammonia percolation pretreatment, ultrasound pretreatment, electroporation pretreatment, microwave pretreatment, supercritical $CO_2$ pretreatment, supercritical $H_2O$ pretreatment, ozone pretreatment, ionic liquid pretreatment, or gamma irradiation pretreatment.

28. The process of claim 8, wherein the enzyme composition further comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

29. The process of claim 28, wherein the enzyme is a cellulase, wherein the cellulase is one or more enzymes selected from the group consisting of an endoglucanase, a cellobiohydrolase, and a beta-glucosidase.

30. The process of claim 28, wherein the enzyme is a hemicellulase, wherein the hemicellulase is one or more enzymes selected from the group consisting of a xylanase, an acetylxylan esterase, a feruloyl esterase, an arabinofuranosidase, a xylosidase, and a glucuronidase.

31. The process of claim 8, wherein the fermenting of the cellulosic material produces a fermentation product.

32. The process of claim 31, further comprising recovering the fermentation product from the fermentation.

33. The process of claim 32, wherein the fermentation product is an alcohol, an alkane, a cycloalkane, an alkene, an amino acid, a gas, isoprene, a ketone, an organic acid, or polyketide.

34. The process of claim 8, wherein the GH61 polypeptide having cellulolytic enhancing activity comprises the amino acid sequence of SEQ ID NO: 10, or the amino acid sequence of amino acids 20 to 336 of SEQ ID NO: 10.

35. The nucleic acid construct of claim 1, wherein the GH61 polypeptide having cellulolytic enhancing activity comprises an amino acid sequence having at least 98% sequence identity to the amino acid sequence of amino acids 20 to 336 of SEQ ID NO: 10.

36. The nucleic acid construct of claim 1, wherein the GH61 polypeptide having cellulolytic enhancing activity comprises an amino acid sequence having at least 99% sequence identity to the amino acid sequence of amino acids 20 to 336 of SEQ ID NO: 10.

37. The process of claim 6, wherein the GH61 polypeptide having cellulolytic enhancing activity comprises an amino acid sequence having at least 96% sequence identity to the amino acid sequence of amino acids 20 to 336 of SEQ ID NO: 10.

38. The process of claim 6, wherein the GH61 polypeptide having cellulolytic enhancing activity comprises an amino acid sequence having as at least 97% sequence identity to the amino acid sequence of amino acids 20 to 336 of SEQ ID NO: 10.

39. The process of claim 6, wherein the GH61 polypeptide having cellulolytic enhancing activity comprises an amino acid sequence having at least 98% sequence identity to the amino acid sequence of amino acids 20 to 336 of SEQ ID NO: 10.

40. The process of claim 6, wherein the GH61 polypeptide having cellulolytic enhancing activity comprises an amino acid sequence having at least 99% sequence identity to the amino acid sequence of amino acids 20 to 336 of SEQ ID NO: 10.

41. The process of claim 7, wherein the GH61 polypeptide having cellulolytic enhancing activity comprises an amino acid sequence having as at least 96% sequence identity to the amino acid sequence of amino acids 20 to 336 of SEQ ID NO: 10.

42. The process of claim 7, wherein the GH61 polypeptide having cellulolytic enhancing activity comprises an amino acid sequence having at least 97% sequence identity to the amino acid sequence of amino acids 20 to 336 of SEQ ID NO: 10.

43. The process of claim 7, wherein the GH61 polypeptide having cellulolytic enhancing activity comprises an amino acid sequence having at least 98% sequence identity to the amino acid sequence of amino acids 20 to 336 of SEQ ID NO: 10.

44. The process of claim 7, wherein the GH61 polypeptide having cellulolytic enhancing activity comprises an amino acid sequence having at least 99% sequence identity to the amino acid sequence of amino acids 20 to 336 of SEQ ID NO: 10.

45. The process of claim 8, wherein the GH61 polypeptide having cellulolytic enhancing activity comprises an amino acid sequence having as at least 96% sequence identity to the amino acid sequence of amino acids 20 to 336 of SEQ ID NO: 10.

46. The process of claim 8, wherein the GH61 polypeptide having cellulolytic enhancing activity comprises an amino acid sequence having at least 97% sequence identity to the amino acid sequence of amino acids 20 to 336 of SEQ ID NO: 10.

47. The process of claim 8, wherein the GH61 polypeptide having cellulolytic enhancing activity comprises an amino acid sequence having at least 98% sequence identity to the amino acid sequence of amino acids 20 to 336 of SEQ ID NO: 10.

48. The process of claim 8, wherein the GH61 polypeptide having cellulolytic enhancing activity comprises an amino acid sequence having as at least 99% sequence identity to the amino acid sequence of amino acids 20 to 336 of SEQ ID NO: 10.

* * * * *